(12) United States Patent
Eickmeier et al.

(10) Patent No.: US 8,865,716 B2
(45) Date of Patent: Oct. 21, 2014

(54) DIHYDROPTERIDINONES II

(71) Applicants: Christian Eickmeier, Mittelbiberach (DE); Kai Gerlach, Mittelbiberach (DE); Niklas Heine, Biberach an der Riss (DE); Alexander Weber, Biberach an der Riss (DE); Ulrike Gross, Biberach an der Riss (DE)

(72) Inventors: Christian Eickmeier, Mittelbiberach (DE); Kai Gerlach, Mittelbiberach (DE); Niklas Heine, Biberach an der Riss (DE); Alexander Weber, Biberach an der Riss (DE); Ulrike Gross, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 60 days.

(21) Appl. No.: 13/767,602

(22) Filed: Feb. 14, 2013

(65) Prior Publication Data

US 2013/0225593 A1 Aug. 29, 2013

(51) Int. Cl.
| | | |
|---|---|---|
| *A01N 43/58* | (2006.01) | |
| *A01N 43/60* | (2006.01) | |
| *A61K 31/50* | (2006.01) | |
| *A61K 31/495* | (2006.01) | |
| *C07D 475/00* | (2006.01) | |
| *A61K 31/519* | (2006.01) | |
| *C07D 491/20* | (2006.01) | |
| *C07D 475/12* | (2006.01) | |

(52) U.S. Cl.
CPC ............ *C07D 491/20* (2013.01); *A61K 31/519* (2013.01); *C07D 475/00* (2013.01); *C07D 475/12* (2013.01)
USPC .......................................... 514/250; 544/258

(58) Field of Classification Search
None
See application file for complete search history.

(56) References Cited

U.S. PATENT DOCUMENTS

| | | | |
|---|---|---|---|
| 6,806,272 B2 | 10/2004 | Bauer et al. | |
| 6,861,422 B2 | 3/2005 | Hoffmann et al. | |
| 7,371,753 B2 | 5/2008 | Stadtmueller et al. | |
| 2004/0029885 A1 | 2/2004 | Bauer et al. | |
| 2004/0176380 A1 | 9/2004 | Hoffmann et al. | |
| 2006/0046990 A1 | 3/2006 | Stadtmueller et al. | |

FOREIGN PATENT DOCUMENTS

| | | |
|---|---|---|
| WO | 03020722 A1 | 3/2003 |
| WO | 2004076454 A1 | 9/2004 |
| WO | 2006021548 A1 | 3/2006 |
| WO | 2006091737 A1 | 8/2006 |
| WO | 2010053438 A1 | 5/2010 |
| WO | 2010132015 A1 | 11/2010 |

OTHER PUBLICATIONS

International Search Report, form PCT/ISA/210, and Written Opinion, form PCT/ISA/237, for corresponding application PCT/EP2013/053404, date of mailing Jun. 4, 2013.

*Primary Examiner* — Jeffrey H Murray
(74) *Attorney, Agent, or Firm* — Michael P. Morris; Alan R. Stempel

(57) ABSTRACT

The present invention relates to spiroheterocycl-dihydropyrimidines, their use as modulators of γ-secretase and to pharmaceutical compositions containing said compounds. In particular, the present invention relates to compounds which interfere with γ-secretase and/or its substrate and therefore modulate the formation of Aβ peptides.

16 Claims, No Drawings

DIHYDROPTERIDINONES II

FIELD OF THE INVENTION

The present invention relates to dihydropteridinones, their use as modulators of γ-secretase and to pharmaceutical compositions containing said compounds. In particular, the present invention relates to compounds which interfere with γ-secretase and/or its substrate and therefore modulate the formation of Aβ peptides. Accordingly these compounds can be used for the treatment of Aβ-related pathologies.

In addition, the invention relates to processes for preparing pharmaceutical compositions as well as compounds according to the invention.

BACKGROUND OF THE INVENTION

Alzheimer's disease (AD) is the most prevalent form of dementia. This neurodegenerative disorder is characterized by two major pathologies, β-amyloid deposits and neurofibrillary tangles. Clinically, AD is characterized by the loss of memory, cognition, reasoning, judgement as well as orientation. As the disease progresses, further abilities are lost until a global impairment of multiple cognitive functions occur. These cognitive losses take place gradually, but typically lead to severe impairment and eventual death in 4-12 years.

β-amyloid deposits are predominantly formed from aggregated Aβ peptide. The Aβ peptide is formed from amyloid precursor protein (APP) through two independent proteolytic events involving β-secretase followed by γ-secretase. Variability in the site of proteolysis via γ-secretase results in Aβ species of variable length, the most predominant forms of which are Aβ38, Aβ40 and Aβ42. The secreted Aβ then aggregates into oligomeric species, which further aggregate to ultimately form the Aβ deposits detected in the brains of AD patients. The aggregated oligomeric species are widely believed to be the key neurotoxic agent responsible for the neurodegeneration detected in the brains of AD patients. Of the various Aβ species generated by γ-secretase, Aβ42 has been demonstrated to be the most aggregation prone as well as the most neurotoxic Aβ species. Furthermore, human genetics strongly supports a key role of Aβ42 as a key mediator of AD pathogenesis. More than 150 different mutations causing familial AD are known which result from either an increase in the ratio of Aβ42/Aβ40 peptides produced or increase the intrinsic aggregation propensity of Aβ. Based on this knowledge, therapeutic approaches aimed at lowering levels of Aβ42 are considered promising.

β-amyloid deposits and vascular amyloid angiopathy have also been characterized in the brains of patients with Trisomy 21 (Down's Syndrome), Hereditary Cerebral Hemorrhage with Amyloidosis of the Dutch-type (HCHWA-D), and other neurodegenerative disorders.

γ-Secretase inhibitors completely inhibit the cleavage of APP as well as all other substrates of γ-secretase. This inhibition leads to a simultaneous inhibition of the production of all Aβ species. As opposed to γ-secretase inhibitors, γ-secretase modulators preferentially block the production of the neurotoxic Aβ42 species while not inhibiting APP cleavage and thereby the generation of all Aβ species. Furthermore, γ-Secretase modulators do not inhibit the cleavage of other γ-secretase substrates, thereby diminishing the possibility of side effects.

WO 2010/053438 discloses compounds of the following core structure

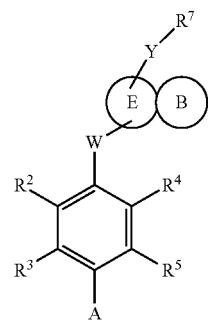

and their use as medicaments in the treatment of diseases like Alzheimer's disease. WO 2010/132015 discloses compounds of the following core structures,

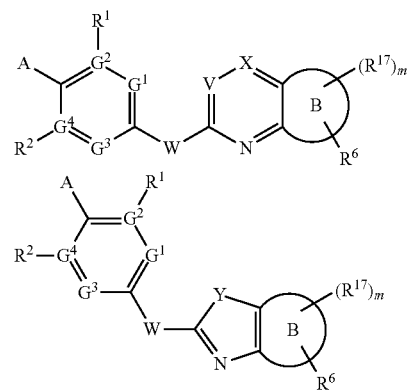

which interfere with gamma-secretase and/or its substrates and modulate β-amyloid peptide production.

Aim of the Invention

It has now been found that compounds of the present invention according to general formula I are effective modulators of γ-secretase.

Accordingly, one aspect of the present invention relates to compounds according to formula I and salts thereof as modulators of γ-secretase.

A further aspect of the invention relates to the physiologically acceptable salts of the compounds of general formula I according to this invention with inorganic or organic acids.

In a further aspect this invention relates to pharmaceutical compositions, containing at least one compound according to formula I or a physiologically acceptable salt thereof, optionally together with one or more inert carriers and/or diluents.

A further aspect of the present invention relates to compounds according to formula I or a physiologically acceptable salt thereof or pharmaceutical compositions comprising compounds according to formula I or physiologically acceptable salts thereof for the use in the prevention and/or treatment of Aβ-related pathologies.

In a further aspect this invention relates to pharmaceutical compositions, containing at least one compound according to formula I or a physiologically acceptable salt thereof, optionally together with one or more inert carriers and/or diluents.

A further aspect of the present invention relates to compounds according to formula I or a physiologically acceptable salt thereof or pharmaceutical compositions comprising compounds according to formula I or physiologically acceptable salts thereof for the use in the prevention and/or treatment of diseases or conditions which can be influenced by modulating Aβ peptides, such as Aβ-related pathologies like Down's syndrome, Abeta-amyloid angiopathy, cerebral amyloid angiopathy, hereditary cerebral hemorrhage, a disorder associated with cognitive impairment, MCI ("mild cognitive impairment"), Alzheimer's Disease, memory loss, attention deficit symptoms associated with Alzheimer's disease, neurodegeneration associated with Alzheimer's disease, diffuse Lewy body type of Alzheimer's Disease, dementia of mixed vascular origin, dementia of degenerative origin, pre-senile dementia, senile dementia, dementia associated with Parkinson's disease, progressive supranuclear palsy or cortical basal degeneration, the dry form of age-related macular degeneration and glaucoma.

Other aims of the present invention will become apparent to the skilled man directly from the foregoing and following remarks.

DETAILED DESCRIPTION

In a first aspect the present invention relates to compounds of general formula I

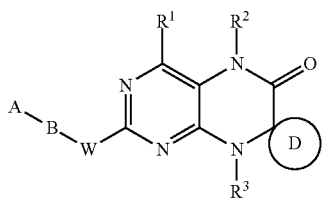

I wherein
A is selected from the group $A^a$ consisting of
a heteroaryl group with 5 or 6 ring atoms containing one to three heteroatoms independently selected from N, O, S,
wherein above mentioned heteroaryl groups may optionally be substituted with 1 or 2 substituents independently selected from the group consisting of halogen, cyano, $C_{1-6}$-alkyl-, HO—$C_{1-6}$-alkyl-, which is optionally fluorinated with 1 to 13 fluorine atoms, $C_{3-6}$-cycloalkyl-, $C_{1-4}$-alkyl-O—$C_{1-3}$-alkyl-, $C_{1-4}$-alkyl-O— which is optionally fluorinated with 1 to 9 fluorine atoms and $(C_{1-4}$-alkyl$)_3$Si—;
B is selected from the group $B^a$ consisting of

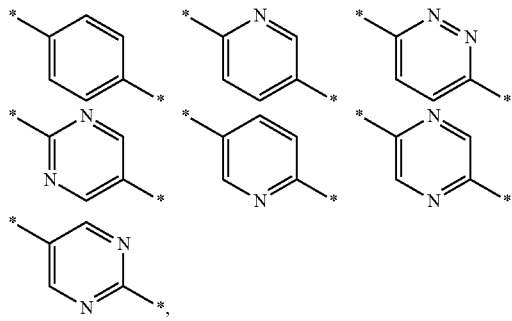

wherein above mentioned phenyl-, pyridinyl-, pyrimidinyl-, pyridazinyl and pyrazinyl groups may optionally be substituted with 1 or 2 substituents independently selected from the group consisting of HO—, halogen, cyano, $C_{1-6}$-alkyl- which is optionally fluorinated with 1 to 13 fluorine atoms, $C_{3-6}$-cycloalkyl-O— and $C_{1-6}$-alkyl-O— which is optionally fluorinated with 1 to 13 fluorine atoms;
D is selected from the group $D^a$ consisting of
a 4- to 12-membered mono-, bicyclic or bridged heterocyclyl group, or a 3- to 12-membered mono- or bicyclic carbocyclyl group,
wherein above mentioned group $D^a$ may optionally be substituted with 1 to 4 substituents independently selected from the group consisting of halogen, cyano, $C_{1-6}$-alkyl- which is optionally fluorinated with 1 to 13 fluorine atoms, $C_{3-6}$-cycloalkyl-, heterocyclyl, aryl, aryl-$C_{1-3}$-alkyl-, heteroaryl, heteroaryl-$C_{1-3}$-alkyl-, HC(O)—, $C_{1-6}$-alkyl-C(O)—, $C_{3-6}$-cycloalkyl-C(O)—, aryl-C(O)—, $C_{1-4}$-alkyl-O—C(O)—, $(C_{1-4}$-alkyl$)_2$N—C(O)—, HO—, oxo, $C_{1-6}$-alkyl-O— which is optionally fluorinated with 1 to 13 fluorine atoms, $C_{3-6}$-cycloalkyl-O—, heterocyclyl-O—, aryl-O—, heteroaryl-O—, $H_2$N—, $(C_{1-4}$-alkyl$)_2$N—, azetidinyl, pyrrolidinyl and $(C_{1-4}$-alkyl$)(C_{1-3}$-alkyl-C(O))N—, and
wherein above mentioned aryl-C(O)—, aryl-O—, aryl, aryl-$C_{1-3}$-alkyl-, heteroaryl, heteroaryl-$C_{1-3}$-alkyl- and heteroaryl-O— groups may optionally be substituted with 1 to 3 substituents independently selected from the group consisting of HO—, $C_{1-4}$-alkyl-O—, $F_3$CO—, $F_3$C—, $F_2$HCO—, $FH_2$CO—, heterocyclyl-O—, cyano, halogen, $F_5$S—, $(C_{1-4}$-alkyl$)_3$Si—, nitro, $H_2$N—, $(C_{1-4}$-alkyl$)_2$N—, $(H_2$N)—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl- which is optionally fluorinated with 1 to 13 fluorine atoms;
W is selected from the group $W^a$ consisting of
—$(R^7)$N— and —O—;
$R^1$ is selected from the group $R^{1a}$ consisting of
H, $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl-, $R^4R^5$N—$C_{1-3}$-alkyl-, $R^4$O—, $R^4S(O)_m$— with m=0, 1, 2,
wherein above mentioned $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl- and $R^4R^5$N—$C_{1-3}$-alkyl- groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $F_5$S—, $(C_{1-4}$-alkyl$)_3$Si—, nitro, $H_2$N—, $(C_{1-4}$-alkyl$)_2$N—, $(H_2$N)—C(O)—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl-, and
wherein above mentioned $C_{1-4}$-alkyl-O—, $C_{3-6}$-cycloalkyl-O—, heterocyclyl-O—, $(C_{1-4}$-alkyl$)_2$N—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl- groups may optionally be substituted with 1 to 13 fluorine atoms;
$R^2$ is selected from the group $R^{ea}$ consisting of
H, $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl-, $R^4R^5$N—, $R^4R^5$N—$C_{1-3}$-alkyl-, $R^4R^5$N—C(O)— and $R^4$O—, wherein above mentioned $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl and heteroaryl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $F_5S$—, $(C_{1-4}$-alkyl$)_3Si$—, nitro, $H_2N$—, $(C_{1-4}$-alkyl$)_2N$—, $(H_2N)$—C(O)—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl-, $C_{3-5}$-cycloalkyl- and $C_{1-6}$-alkyl-, and wherein above mentioned $C_{1-4}$-alkyl-O—, $C_{3-6}$-cycloalkyl-O—, heterocyclyl-O—, $(C_{1-4}$-alkyl$)_2N$—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl-, $C_{3-5}$-cycloalkyl- and $C_{1-6}$-alkyl- may optionally be substituted with 1 to 13 fluorine atoms;

$R^3$ is selected from the group $R^{3a}$ consisting of

H, $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl-, $R^4R^5N$—, $R^4R^5N$—$C_{1-3}$-alkyl-, and $R^4O$—, wherein above mentioned $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl and heteroaryl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $F_5S$—, $(C_{1-4}$-alkyl$)_3Si$—, nitro, $H_2N$—, $(C_{1-4}$-alkyl$)_2N$—, $(H_2N)$—C(O)—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl-, and wherein above mentioned $C_{1-4}$-alkyl-O—, $C_{3-6}$-cycloalkyl-O—, heterocyclyl-O—, $(C_{1-4}$-alkyl$)_2N$—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl- groups may optionally be substituted with 1 to 13 fluorine atoms;

$R^4$, $R^5$ are selected independently of each other from the group $R^{4a}/R^{5a}$ consisting of H, $C_{1-6}$-alkyl-, carbocyclyl, carbocyclyl-$C_{1-3}$-alkyl-, carbocyclyl-O—$C_{2-4}$-alkyl-, heterocyclyl, heterocyclyl-$C_{1-6}$-alkyl-, heterocyclyl-O—$C_{2-4}$-alkyl-, aryl, aryl-$C_{1-3}$-alkyl-, aryl-O—$C_{2-3}$-alkyl-, heteroaryl, heteroaryl-$C_{1-3}$-alkyl- and heteroaryl-O—$C_{2-3}$-alkyl-, wherein above mentioned $C_{1-6}$-alkyl-, carbocyclyl, carbocyclyl-$C_{1-3}$-alkyl-, carbocyclyl-O—$C_{2-4}$-alkyl-, heterocyclyl, heterocyclyl-$C_{1-6}$-alkyl- or heterocyclyl-O—$C_{2-4}$-alkyl- groups may optionally be substituted with 1 to 3 substituents independently selected from the group consisting of halogen, cyano, HO—, oxo, $C_{1-4}$-alkyl-O— which is optionally fluorinated with 1 to 9 fluorine atoms, $C_{1-4}$-alkyl-O—C(O)—, HO—$C_{1-4}$-alkyl-, $C_{1-4}$-alkyl-O—$C_{1-4}$-alkyl-, heterocyclyl, $(C_{1-4}$-alkyl$)_2N$—, $(C_{1-3}$-alkyl$)_2N$—C(O)—, and $C_{1-6}$-alkyl- which is optionally fluorinated with 1 to 13 fluorine atoms, wherein above mentioned aryl-, aryl-$C_{1-3}$-alkyl-, aryl-O—$C_{2-3}$-alkyl-, heteroaryl-, heteroaryl-$C_{1-3}$-alkyl- and heteroaryl-O—$C_{2-3}$-alkyl- groups may optionally be substituted with 1 to 3 substituents independently selected from the group consisting of HO—, $C_{1-4}$-alkyl-O—, $F_3CO$—, $F_2HCO$—, $FH_2CO$—, heterocyclyl-O—, cyano, halogen, $F_5S$—, $(C_{1-4}$-alkyl$)_3Si$—, nitro, $(R^6)_2N$—, $(H_2N)$—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl- which is optionally fluorinated with 1 to 13 fluorine atoms, or $R^{4a}$ and $R^{5a}$ form together with the nitrogen atom to which they are attached a 4-12-membered mono-, bicyclic or bridged ring system optionally containing one or two double bonds and/or one aromatic ring and optionally containing one or two additional heteroatoms selected from the group consisting of —O—, —S—, —S(O)—, —S(O)$_2$—, —N(R$^6$)—, wherein 2 geminal hydrogen atoms of the 4-12-membered mono- or bicyclic ring system may be replaced by a —(CH$_2$)$_{1-5}$— group and wherein one —(CH$_2$)— group of the —(CH$_2$)$_{1-5}$— group may be replaced by —O— or —N(R$^6$)— and wherein above mentioned 4-12-membered mono-, bicyclic or bridged ring system may optionally be substituted with 1 or 2 substituents independently selected from the group consisting of halogen, cyano, aryl, heteroaryl, aryl-$C_{1-3}$-alkyl-, $C_{1-6}$-alkyl- which is optionally fluorinated with 1 to 13 fluorine atoms, heterocyclyl, HO—, oxo, $C_{1-6}$-alkyl-O—, $C_{3-6}$-cycloalkyl-O—, $C_{1-4}$-alkyl-O—C(O)—, HO—$C_{1-4}$-alkyl-, $C_{1-4}$-alkyl-O—$C_{1-4}$-alkyl-, $C_{3-6}$-cycloalkyl-O—$C_{1-4}$-alkyl-, heterocyclyl-O—, heterocyclyl-O—$C_{1-4}$-alkyl-, aryl-O—, heteroaryl-O— and $(R^6)_2N$—, wherein the directly above mentioned aryl, aryl-$C_{1-3}$-alkyl-, aryl-O—, heteroaryl-O—, and heteroaryl groups may optionally be substituted with 1 to 3 substituents independently selected from the group consisting of HO—, $C_{1-4}$-alkyl-O—, $F_3CO$—, $F_2HCO$—, $FH_2CO$—, heterocyclyl-O—, cyano, halogen, $F_5S$—, $(C_{1-4}$-alkyl$)_3Si$—, nitro, amino, $(C_{1-4}$-alkyl$)_2N$—, $(H_2N)$—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl- which is optionally fluorinated with 1 to 13 fluorine atoms;

$R^6$ is selected independently of each other from the group $R^{6a}$ consisting of H, $C_{1-6}$-alkyl-, $C_{3-6}$-cycloalkyl, heterocyclyl, heteroaryl, HC(O)—, $C_{1-6}$-alkyl-C(O)—, $C_{3-6}$-cycloalkyl-C(O)—, aryl-C(O)—, $C_{1-4}$-alkyl-O—C(O)— and $(C_{1-4}$-alkyl$)_2N$—C(O)—, wherein above mentioned $C_{1-6}$-alkyl-, $C_{3-6}$-cycloalkyl-, $C_{1-6}$-alkyl-C(O)— and $C_{3-6}$-cycloalkyl-C(O)— groups may optionally be substituted with 1-13 fluorine atoms wherein the above mentioned aryl-C(O)— and heteroaryl group may optionally be substituted with 1 to 3 substituents independently selected from the group consisting of HO—, $C_{1-4}$-alkyl-O—, $F_3CO$—, $F_2HCO$—, $FH_2CO$—, heterocyclyl-O—, cyano, halogen, $F_5S$—, $(C_{1-4}$-alkyl$)_3Si$—, nitro, amino, $(C_{1-4}$-alkyl$)_2N$—, $(H_2N)$—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl- which is optionally fluorinated with 1 to 13 fluorine atoms;

$R^7$ is selected from the group $R^{7a}$ consisting of

H and $C_{1-5}$-alkyl- which is optionally fluorinated with 1 to 13 fluorine atoms, the tautomers thereof, the stereoisomers thereof, the mixtures thereof and the salts thereof.

Unless otherwise stated, the groups, residues, and substituents, particularly $R^1, R^2, R^3, R^4, R^5, R^6, R^7, A, B, D$ and $W$ are defined as above and hereinafter. If residues, substituents, or groups occur several times in a compound they may have the same or different meanings. Some preferred meanings of groups and substituents of the compounds according to the invention will be given hereinafter.

In a further embodiment of the present invention
A is selected from the group $A^b$ consisting of

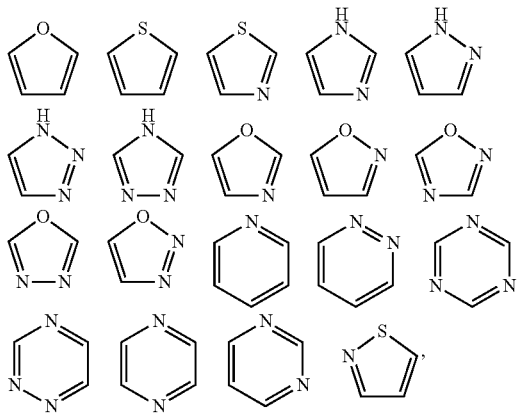

wherein above mentioned groups may optionally be substituted with 1 or 2 substituents independently selected from the group consisting of halogen, cyano, and $C_{1-6}$-alkyl- which is optionally fluorinated with 1 to 13 fluorine atoms.

In a further embodiment of the present invention
A is selected from the group $A^c$ consisting of

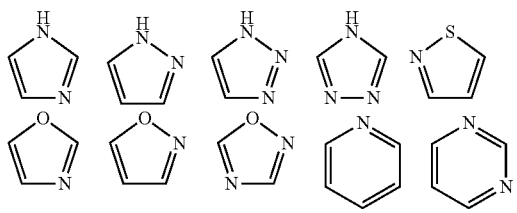

wherein above mentioned groups may optionally be substituted with 1 or 2 substituents independently selected from the group consisting of halogen and $C_{1-3}$-alkyl- which is optionally fluorinated with 1 to 7 fluorine atoms.

In a further embodiment of the present invention
A is selected from the group $A^d$ consisting of

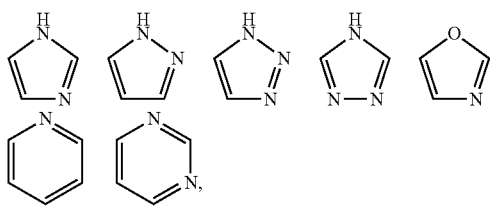

wherein above mentioned groups may optionally be substituted with 1 or 2 substituents independently selected from the group consisting of halogen and $C_{1-3}$-alkyl- which is optionally fluorinated with 1 to 7 fluorine atoms.

In a further embodiment of the present invention
A is selected from the group $A^e$ consisting of

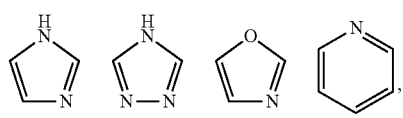

wherein above mentioned groups may optionally be substituted with 1 or 2 substituents independently selected from the group consisting of halogen and $C_{1-3}$-alkyl- which is optionally fluorinated with 1 to 7 fluorine atoms.

In a further embodiment of the present invention
B is selected from the group $B^b$ consisting of

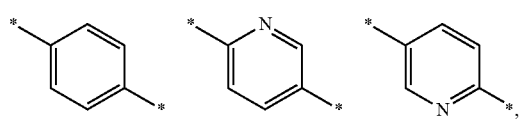

wherein above mentioned phenyl- and pyridinyl-groups may optionally be substituted with 1 or 2 substituents independently selected from the group consisting of HO—, halogen, cyano, $C_{1-6}$-alkyl- which is optionally fluorinated with 1 to 13 fluorine atoms, $C_{3-6}$-cycloalkyl-O— and $C_{1-6}$-alkyl-O— which is optionally fluorinated with 1 to 13 fluorine atoms.

In a further embodiment of the present invention
B is selected from the group $B^c$ consisting of

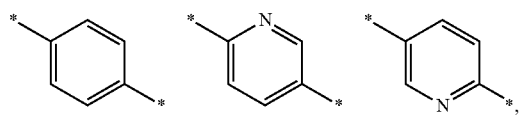

wherein above mentioned phenyl- and pyridinyl- groups may optionally be substituted with 1 or 2 substituents independently selected from the group consisting of halogen, cyano, $C_{1-3}$-alkyl- which is optionally fluorinated with 1 to 7 fluorine atoms, and $C_{1-3}$-alkyl-O— which is optionally fluorinated with 1 to 7 fluorine atoms.

In a further embodiment of the present invention
D is selected from the group $D^b$ consisting of

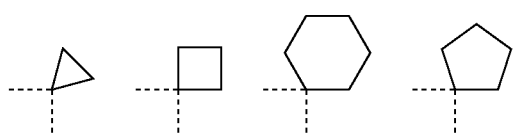

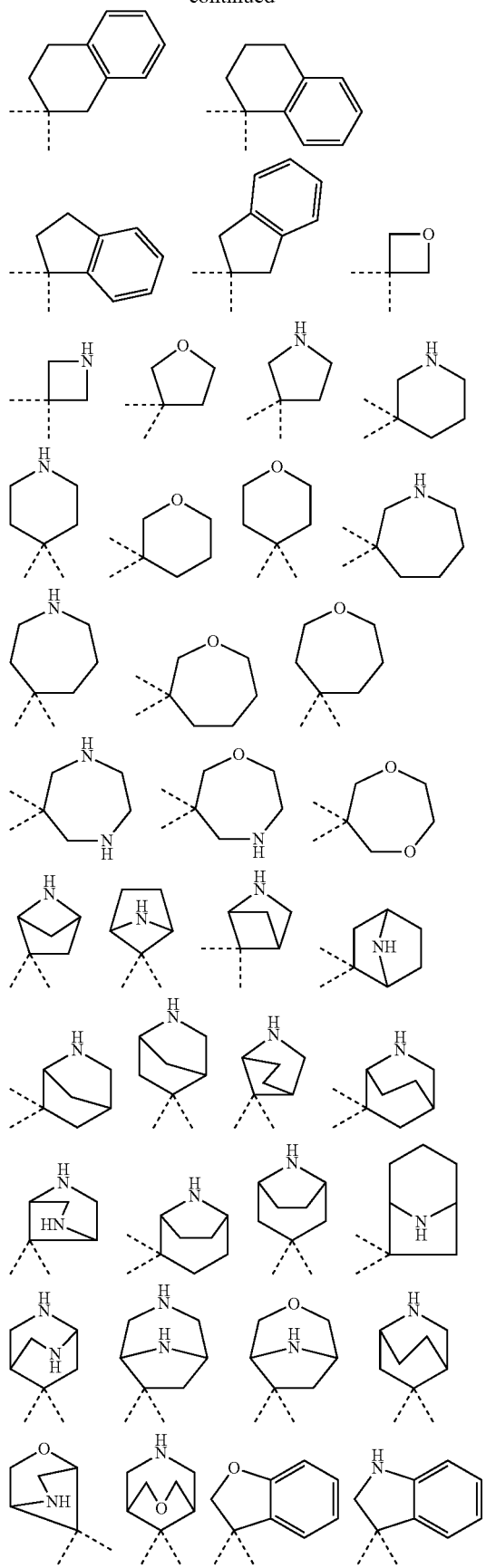
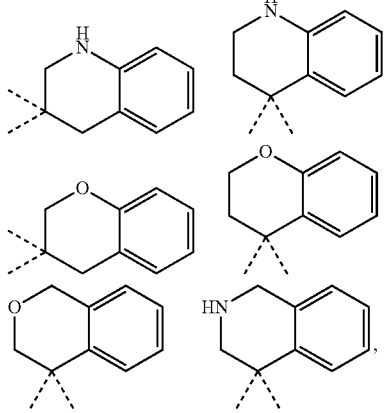

wherein above mentioned ring system $D^b$ may optionally be substituted with 1 to 4 substituents independently selected from the group consisting of halogen, cyano, $C_{1-6}$-alkyl- which is optionally fluorinated with 1 to 13 fluorine atoms, $C_{3-6}$-cycloalkyl-, heterocyclyl, aryl, aryl-$C_{1-3}$-alkyl-, heteroaryl, heteroaryl-$C_{1-3}$-alkyl-, HC(O)—, $C_{1-6}$-alkyl-C(O)—, $C_{3-6}$-cycloalkyl-C(O)—, aryl-C(O)—, $C_{1-4}$-alkyl-O—C(O)—, $(C_{1-4}$-alkyl$)_2$N—C(O)—, HO—, oxo, $C_{1-6}$-alkyl-O— which is optionally fluorinated with 1 to 13 fluorine atoms, $C_{3-6}$-cycloalkyl-O—, heterocyclyl-O—, aryl-O—, heteroaryl-O—, $H_2N$—, $(C_{1-4}$-alkyl$)_2$N—, azetidinyl, pyrrolidinyl and $(C_{1-4}$-alkyl$)(C_{1-3}$-alkyl-C(O))N—, and wherein above mentioned aryl-C(O)—, aryl-O—, aryl, aryl-$C_{1-3}$-alkyl-, heteroaryl, heteroaryl-$C_{1-3}$-alkyl- and heteroaryl-O— groups may optionally be substituted with 1 to 3 substituents independently selected from the group consisting of HO—, $C_{1-4}$-alkyl-O—, $F_3CO$—, $F_3C$—, $F_2HCO$—, $FH_2CO$—, heterocyclyl-O—, cyano, halogen, $F_5S$—, $(C_{1-4}$-alkyl$)_3$Si—, nitro, $H_2N$—, $(C_{1-4}$-alkyl$)_2$N—, $(H_2N)$—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl- which is optionally fluorinated with 1 to 13 fluorine atoms.

In a further embodiment of the present invention

D is selected from the group $D^c$ consisting of

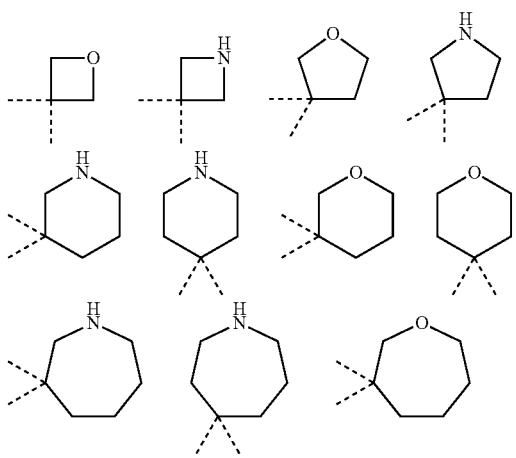

-continued

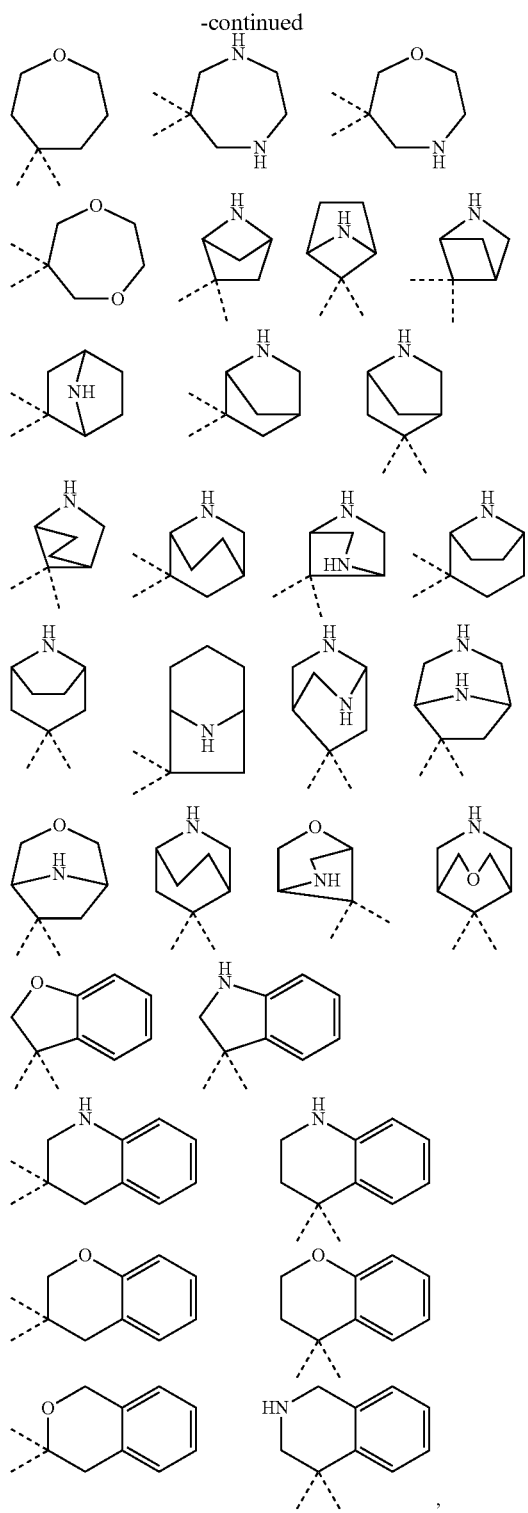

wherein above mentioned ring system D$^c$ may optionally be substituted with 1 to 4 substituents independently selected from the group consisting of halogen, cyano, C$_{1-6}$-alkyl- which is optionally fluorinated with 1 to 13 fluorine atoms, C$_{3-6}$-cycloalkyl-, heterocyclyl, aryl, aryl-C$_{1-3}$-alkyl-, heteroaryl, heteroaryl-C$_{1-3}$-alkyl-, HC(O)—, C$_{1-6}$-alkyl-C(O)—, C$_{3-6}$-cycloalkyl-C(O)—, aryl-C(O)—, C$_{1-4}$-alkyl-O—C(O)—, (C$_{1-4}$-alkyl)$_2$N—C(O)—, HO—, oxo, C$_{1-6}$-alkyl-O— which is optionally fluorinated with 1 to 13 fluorine atoms, C$_{3-6}$-cycloalkyl-O—, heterocyclyl-O—, aryl-O—, heteroaryl-O—, H$_2$N—, (C$_{1-4}$-alkyl)$_2$N—, azetidinyl, pyrrolidinyl and (C$_{1-4}$-alkyl)(C$_{1-3}$-alkyl-C(O))N—, and wherein above mentioned aryl-C(O)—, aryl-O—, aryl, aryl-C$_{1-3}$-alkyl-, heteroaryl, heteroaryl-C$_{1-3}$-alkyl- and heteroaryl-O— groups may optionally be substituted with 1 to 3 substituents independently selected from the group consisting of HO—, C$_{1-4}$-alkyl-O—, F$_3$CO—, F$_3$C—, F$_2$HCO—, FH$_2$CO—, heterocyclyl-O—, cyano, halogen, F$_5$S—, (C$_{1-4}$-alkyl)$_3$Si—, nitro, H$_2$N—, (C$_{1-4}$-alkyl)$_2$N—, (H$_2$N)—C(O)—, (C$_{1-4}$-alkyl)-HN—C(O)—, (C$_{1-4}$-alkyl)$_2$N—C(O)—, C$_{1-4}$-alkyl-O—C$_{1-4}$-alkyl- and C$_{1-6}$-alkyl- which is optionally fluorinated with 1 to 13 fluorine atoms.

In a further embodiment of the present invention

D is selected from the group D$^d$ consisting of

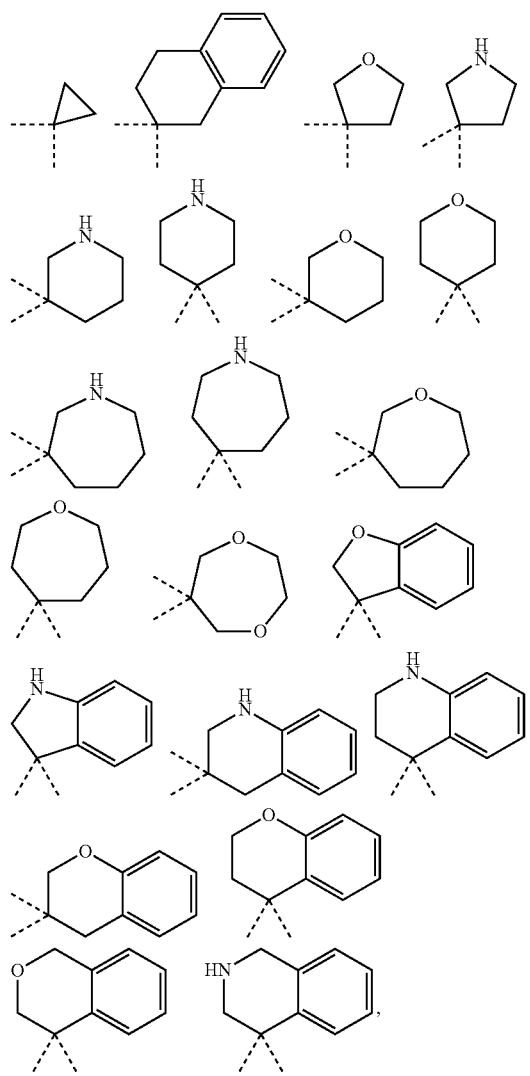

wherein above mentioned ring D$^d$ may optionally be substituted with 1 to 4 substituents independently selected from the group consisting of halogen, cyano, C$_{1-6}$-alkyl- which is optionally fluorinated with 1 to 13 fluorine atoms, $C_{3-6}$-cycloalkyl-, oxetanyl, tetrahydrofuryl, tetrahydropyranyl, phenyl, phenyl-$C_{1-3}$-alkyl-, heteroaryl, heteroaryl-$C_{1-3}$-alkyl-, HC(O)—, $C_{1-6}$-alkyl-C(O)—, $C_{3-6}$-cycloalkyl-C(O)—, phenyl-C(O)—, $C_{1-4}$-alkyl-O—C(O)—, ($C_{1-4}$-alkyl)$_2$N—C(O)—, HO—, oxo, $C_{1-6}$-alkyl-O— which is optionally fluorinated with 1 to 13 fluorine atoms, $C_{3-6}$-cycloalkyl-O—, oxetanyl-O—, tetrahydrofuryl-O—, tetrahydropyranyl-O—, phenyl-O—, heteroaryl-O—, H$_2$N—, ($C_{1-4}$-alkyl)$_2$N—, azetidinyl, pyrrolidinyl and ($C_{1-4}$-alkyl)($C_{1-3}$-alkyl-C(O))N—, and wherein above mentioned phenyl, phenyl-$C_{1-3}$-alkyl-, heteroaryl-$C_{1-3}$-alkyl-, phenyl-C(O)—, phenyl-O—, heteroaryl- and heteroaryl-O— group may optionally be substituted with 1 to 3 substituents independently selected from the group consisting of HO—, $C_{1-4}$-alkyl-O—, F$_3$C—, F$_3$C—, F$_2$HCO—, FH$_2$CO—, oxetanyl-O—, tetrahydrofuryl-O—, tetrahydropyranyl-O—, cyano, halogen, F$_5$S—, ($C_{1-4}$-alkyl)$_3$Si—, nitro, H$_2$N—, ($C_{1-4}$-alkyl)$_2$N—, (H$_2$N)—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl- and $C_{1-6}$-alkyl- which is optionally fluorinated with 1 to 13 fluorine atoms.

In a further embodiment of the present invention

D is selected from the group D$^e$ consisting of

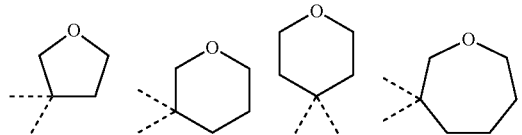

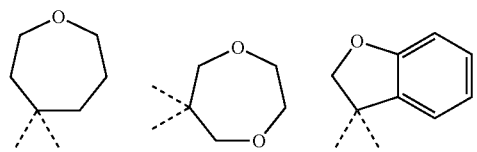

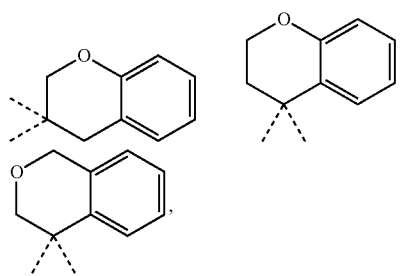

wherein above mentioned rings D$^e$ may optionally be substituted with 1 to 4 substituents independently selected from the group consisting of halogen, cyano, $C_{1-6}$-alkyl- which is optionally fluorinated with 1 to 13 fluorine atoms, $C_{3-6}$-cycloalkyl-, phenyl- wherein above mentioned phenyl may optionally be substituted with 1 to 3 substituents independently selected from the group consisting of $C_{1-4}$-alkyl-O—, F$_3$C—, F$_2$HCO—, FH$_2$CO—, cyano, halogen, F$_5$S— and $C_{1-6}$-alkyl- which is optionally fluorinated with 1 to 13 fluorine atoms.

In a further embodiment of the present invention

D is selected from the group D$^f$ consisting of

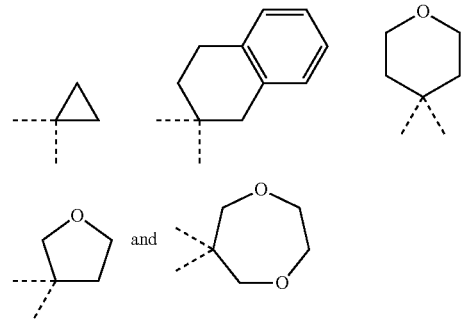

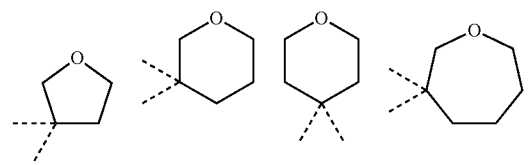

wherein above mentioned rings D$^e$ may optionally be substituted with 1 to 4 substituents independently selected from the group consisting of halogen, cyano, $C_{1-6}$-alkyl- which is optionally fluorinated with 1 to 13 fluorine atoms, $C_{3-6}$-cycloalkyl-, phenyl-$C_{1-3}$-alkyl- and phenyl-, and wherein above mentioned phenyl-$C_{1-3}$-alkyl- and phenyl- groups may optionally be substituted with 1 to 3 substituents independently selected from the group consisting of $C_{1-4}$-alkyl-O—, F$_3$CO—, F$_2$HCO—, FH$_2$CO—, cyano, halogen, F$_5$S— and $C_{1-6}$-alkyl- which is optionally fluorinated with 1 to 13 fluorine atoms.

In a further embodiment of the present invention

D is selected from the group D$^g$ consisting of

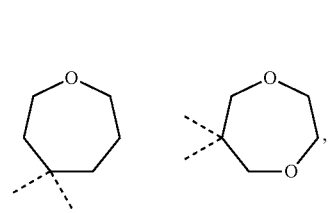

wherein above mentioned ring Dg may optionally be substituted with 1 to 2 substituents independently selected from the group consisting of phenyl, phenyl-$C_{1-3}$-alkyl-, fluoro, $C_{1-6}$-alkyl- and $C_{1-3}$-alkyl-O—, and wherein above mentioned phenyl and phenyl-$C_{1-3}$-alkyl- groups may optionally be substituted with 1 to 3 substituents independently selected from the group consisting of $C_{1-4}$-alkyl-O—, F$_3$C—, F$_3$CO—, F$_2$HCO—, FH$_2$CO—, cyano, halogen, and $C_{1-3}$-alkyl-.

In a further embodiment of the present invention
D is selected from the group $D^h$ consisting of

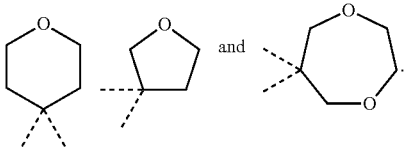

In a further embodiment of the present invention
W is selected from the group $W^b$ consisting of
—($R^7$)N—.

In a further embodiment of the present invention
$R^1$ is selected from the group $R^{1b}$ consisting of H, $C_{1-8}$-alkyl-, carbocyclyl, carbocyclyl-$C_{1-3}$-alkyl-, C-linked heterocyclyl, heterocyclyl-$C_{1-3}$-alkyl-, heteroaryl, heteroaryl-$C_{1-3}$-alkyl-, $R^4R^5N$—$C_{1-3}$-alkyl-, $R^4O$—, and $R^4S(O)_m$— with m=0, 1, 2 wherein above mentioned $C_{1-8}$-alkyl-, carbocyclyl, carbocyclyl-$C_{1-3}$-alkyl-, C-linked heterocyclyl, heterocyclyl-$C_{1-3}$-alkyl-, heteroaryl, heteroaryl-$C_{1-3}$-alkyl- and $R^4R^5N$—$C_{1-3}$-alkyl- groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $H_2N$—, ($C_{1-4}$-alkyl)$_2$N—, ($C_{1-4}$-alkyl)-C(O)—, ($C_{1-4}$-alkyl)-O—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl- and $C_{1-6}$-alkyl-, and wherein above mentioned $C_{1-4}$-alkyl-O—, $C_{3-6}$-cycloalkyl-O—, heterocyclyl-O—, ($C_{1-4}$-alkyl)$_2$N—, ($C_{1-4}$-alkyl)-C(O)—, ($C_{1-4}$-alkyl)-O—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl- and $C_{1-6}$-alkyl- may optionally be substituted with 1 to 13 fluorine atoms.

In a further embodiment of the present invention
$R^1$ is selected from the group $R^{1c}$ consisting of H, $C_{1-8}$-alkyl-, carbocyclyl, carbocyclyl-$C_{1-3}$-alkyl-, C-linked heterocyclyl, and heterocyclyl-$C_{1-3}$-alkyl-, wherein above mentioned $C_{1-8}$-alkyl-, carbocyclyl, carbocyclyl-$C_{1-3}$-alkyl-, C-linked heterocyclyl and heterocyclyl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $C_{1-4}$-alkyl-O—$C_{1-4}$-alkyl- and $C_{1-6}$-alkyl-, and wherein above mentioned $C_{1-4}$-alkyl-O—, $C_{3-6}$-cycloalkyl-O—, heterocyclyl-O—, $C_{1-4}$-alkyl-O—$C_{1-4}$-alkyl- and $C_{1-6}$-alkyl- may optionally be substituted with 1 to 13 fluorine atoms.

In a further embodiment of the present invention
$R^1$ is selected from the group $R^{1d}$ consisting of H, $C_{1-5}$-alkyl-, $C_{3-6}$-cycloalkyl-, $C_{3-6}$-cycloalkyl-$C_{1-2}$-alkyl-, $R^4R^5N$—$C_{1-3}$-alkyl-, C-linked heterocyclyl and heterocyclyl-$C_{1-6}$-alkyl-, wherein the heterocyclyl-groups are selected from the group consisting of

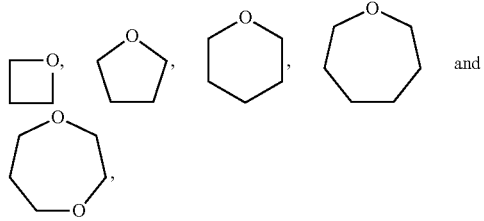

wherein above mentioned $C_{1-5}$-alkyl-, $C_{3-6}$-cycloalkyl-, $C_{3-6}$-cycloalkyl-$C_{1-2}$-alkyl-, C-linked heterocyclyl and heterocyclyl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $C_{1-4}$-alkyl-O—$C_{1-4}$-alkyl- and $C_{1-6}$-alkyl-, and wherein above mentioned $C_{1-4}$-alkyl-O—, $C_{3-6}$-cycloalkyl-O—, heterocyclyl-O—, $C_{1-4}$-alkyl-O—$C_{1-4}$-alkyl- and $C_{1-6}$-alkyl- groups may optionally be substituted with 1 to 13 fluorine atoms.

In a further embodiment of the present invention
$R^1$ is selected from the group $R^{1e}$ consisting of H, $C_{1-6}$-alkyl-, $C_{3-6}$-cycloalkyl-, $C_{3-6}$-cycloalkyl-$C_{1-2}$-alkyl-, C-linked heterocyclyl, heterocyclyl-$C_{1-6}$-alkyl-, wherein the C-linked heterocyclyl-groups are selected from the group consisting of

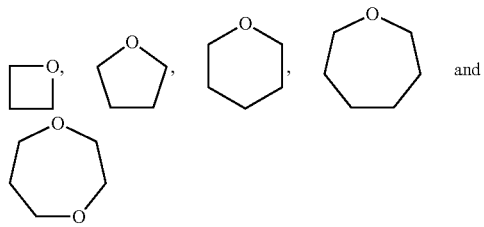

wherein above mentioned $C_{1-5}$-alkyl-, $C_{3-6}$-cycloalkyl-, $C_{3-6}$-cycloalkyl-$C_{1-2}$-alkyl-, C-linked heterocyclyl and heterocyclyl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $C_{1-4}$-alkyl-O—$C_{1-4}$-alkyl- and $C_{1-6}$-alkyl-, and wherein above mentioned $C_{1-4}$-alkyl-O—, $C_{3-6}$-cycloalkyl-O—, heterocyclyl-O—, $C_{1-4}$-alkyl-O—$C_{1-4}$-alkyl- and $C_{1-6}$-alkyl- groups may optionally be substituted with 1 to 13 fluorine atoms.

In a further embodiment of the present invention
$R^1$ is selected from the group $R^{1f}$ consisting of H, $C_{1-4}$-alkyl-, wherein above mentioned $C_{1-8}$-alkyl-groups may optionally be substituted with 1 to 3 substituents independently selected from the group consisting of HO—, $C_{1-3}$-alkyl-O—, cyano, and halogen.

In a further embodiment of the present invention
$R^2$ is selected from the group $R^{2b}$ consisting of H, $C_{1-8}$-alkyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl- and $R^4R^5N$—$C_{2-3}$-alkyl-, wherein above mentioned $C_{1-8}$-alkyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl and heteroaryl-$C_{1-3}$-alkyl- groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $H_2N$—, ($C_{1-4}$-alkyl)$_2N$—, ($H_2N$)—C(O)—, ($C_{1-4}$-alkyl)-C(O)—, ($C_{1-4}$-alkyl)-O—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl-, $C_{3-5}$-cycloalkyl- and $C_{1-6}$-alkyl-, and wherein above mentioned $C_{1-4}$-alkyl-O—, $C_{3-6}$-cycloalkyl-O—, heterocyclyl-O—, ($C_{1-4}$-alkyl)$_2$N—, ($C_{1-4}$-alkyl)-C(O)—, ($C_{1-4}$-alkyl)-O—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl-, $C_{3-5}$-cycloalkyl- and $C_{1-6}$-alkyl- groups may optionally be substituted with 1 to 13 fluorine atoms.

In a further embodiment of the present invention
$R^2$ is selected from the group $R^{2c}$ consisting of
H, $C_{1-8}$-alkyl-, $C_{3-7}$-cycloalkyl-, $C_{3-7}$-cycloalkyl-$C_{1-3}$-alkyl-, phenyl, phenyl-$C_{1-3}$-alkyl-, C-linked heterocyclyl and heterocyclyl-$C_{1-3}$-alkyl-, wherein above mentioned $C_{1-8}$-alkyl-, $C_{3-7}$-cycloalkyl-, $C_{3-7}$-cycloalkyl-$C_{1-3}$-alkyl-, phenyl, phenyl-$C_{1-3}$-alkyl-, C-linked heterocyclyl and heterocyclyl-$C_{1-3}$-alkyl- groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $C_{1-4}$-alkyl-O—$C_{1-4}$-alkyl-, $C_{3-5}$-cycloalkyl- and $C_{1-6}$-alkyl-, and wherein above mentioned $C_{1-4}$-alkyl-O—, $C_{3-6}$-cycloalkyl-O—, heterocyclyl-O—, $C_{1-4}$-alkyl-O—$C_{1-4}$-alkyl-, $C_{3-5}$-cycloalkyl- and $C_{1-6}$-alkyl- groups may optionally be substituted with 1 to 13 fluorine atoms.

In a further embodiment of the present invention
$R^2$ is selected from the group $R^{2d}$ consisting of
H, $C_{1-5}$-alkyl-, $C_{3-6}$-cycloalkyl-, C-linked heterocyclyl-, phenyl and phenyl-$C_{1-3}$-alkyl-, wherein above mentioned $C_{1-5}$-alkyl-, $C_{3-6}$-cycloalkyl-, C-linked heterocyclyl-, phenyl and phenyl-$C_{1-3}$-alkyl-groups may optionally be substituted with 1 to 3 substituents independently selected from the group consisting of HO—, $C_{1-3}$-alkyl-O— and a saturated 4 to 6 membered monocyclic ring containing one O atom, wherein above mentioned $C_{1-5}$-alkyl-, $C_{3-6}$-cycloalkyl-, C-linked heterocyclyl-, phenyl, phenyl-$C_{1-3}$-alkyl- and $C_{1-3}$-alkyl-O— groups may optionally be substituted with 1 to 11 fluorine atoms.

In a further embodiment of the present invention
$R^2$ is selected from the group $R^{2e}$ consisting of
H, $C_{1-5}$-alkyl-, $C_{1-3}$-alkyl-O—$C_{1-3}$-alkyl-, cyclopropyl, phenyl,

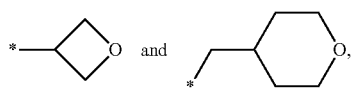

wherein above mentioned $C_{1-5}$-alkyl- and phenyl groups may optionally be substituted with 1 to 3 fluoroatoms.

In a further embodiment of the present invention
$R^3$ is selected from the group $R^{3b}$ consisting of
H, $C_{1-8}$-alkyl-, carbocyclyl, carbocyclyl-$C_{1-3}$-alkyl-, C-linked heterocyclyl, heterocyclyl-$C_{1-3}$-alkyl-, aryl-$C_{1-3}$-alkyl-, heteroaryl-$C_{1-3}$-alkyl- and $R^4R^5N$—$C_{2-3}$-alkyl-, wherein above mentioned $C_{1-8}$-alkyl-, carbocyclyl, carbocyclyl-$C_{1-3}$-alkyl-, C-linked heterocyclyl, heterocyclyl-$C_{1-3}$-alkyl-, aryl-$C_{1-3}$-alkyl-, and heteroaryl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $H_2N$—, ($C_{1-4}$-alkyl)$_2N$—, ($H_2N$)—C(O)—, ($C_{1-4}$-alkyl)-C(O)—, ($C_{1-4}$-alkyl)-O—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl- and $C_{1-6}$-alkyl-, and wherein above mentioned $C_{1-4}$-alkyl-O—, $C_{3-6}$-cycloalkyl-O—, heterocyclyl-O—, ($C_{1-4}$-alkyl)$_2$N—, ($C_{1-4}$-alkyl)-C(O)—, ($C_{1-4}$-alkyl)-O—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl- and $C_{1-6}$-alkyl- groups may optionally be substituted with 1 to 13 fluorine atoms.

In a further embodiment of the present invention
$R^3$ is selected from the group $R^{3c}$ consisting of
H, $C_{3-5}$-cycloalkyl and $C_{1-5}$-alkyl-, wherein above mentioned $C_{3-5}$-cycloalkyl- and $C_{1-5}$-alkyl- groups may optionally be substituted with 1 to 3 substituents independently selected from the group consisting of HO—, $C_{1-4}$-alkyl-O—, $C_{3-6}$-cycloalkyl-O—, heterocyclyl-O— and $C_{1-4}$-alkyl-O—$C_{1-4}$-alkyl-, and wherein above mentioned $C_{1-4}$-alkyl-O—, $C_{3-6}$-cycloalkyl-O—, heterocyclyl-O— and $C_{1-4}$-alkyl-O—$C_{1-4}$-alkyl- groups may optionally be substituted with 1 to 13 fluorine atoms.

In a further embodiment of the present invention
$R^3$ is selected from the group $R^{3d}$ consisting of
H, and $C_{1-5}$-alkyl-, wherein above mentioned $C_{1-5}$-alkyl- group may optionally be substituted with 1 to 3 substituents independently selected from the group consisting of HO—, $C_{1-4}$-alkyl-O—, $C_{3-6}$-cycloalkyl-O—, heterocyclyl-O—, and $C_{1-4}$-alkyl-O—$C_{1-4}$-alkyl-, and wherein above mentioned $C_{1-4}$-alkyl-O—, $C_{3-6}$-cycloalkyl-O—, heterocyclyl-O— and $C_{1-4}$-alkyl-O—$C_{1-4}$-alkyl- groups may optionally be substituted with 1 to 13 fluorine atoms.

In a further embodiment of the present invention
$R^3$ is selected from the group $R^{3e}$ consisting of
H and $H_3C$—.

In a further embodiment of the present invention
$R^4$, $R^5$ are selected independently of each other from the group $R^{4b}/R^{5b}$ consisting of
H, $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, heterocyclyl, heterocyclyl-$C_{1-6}$-alkyl-, aryl, aryl-$C_{1-3}$-alkyl-, aryl-O—$C_{2-3}$-alkyl-, heteroaryl and heteroaryl-$C_{1-3}$-alkyl-, wherein above mentioned $C_{1-6}$-alkyl-, $C_{3-7}$-cycloalkyl-, $C_{3-7}$-cycloalkyl-$C_{1-3}$-alkyl-, $C_{3-7}$-cycloalkyl-O—$C_{2-4}$-alkyl-, heterocyclyl or heterocyclyl-$C_{1-6}$-alkyl- groups may optionally be substituted with 1 to 3 substituents independently selected from the group consisting of fluoro, HO—, oxo, $C_{1-4}$-alkyl-O— which is optionally fluorinated with 1 to 9 fluorine atoms, HO—$C_{1-4}$-alkyl-, $C_{1-4}$-alkyl-O—$C_{1-4}$-alkyl-, heterocyclyl, $(C_{1-3}$-alkyl$)_2$N—C(O)—, and $C_{1-6}$-alkyl- which is optionally fluorinated with 1 to 13 fluorine atoms, wherein above mentioned aryl-, aryl-$C_{1-3}$-alkyl-, aryl-O—$C_{2-3}$-alkyl-, heteroaryl- and heteroaryl-$C_{1-3}$-alkyl- groups may optionally be substituted with 1 to 3 substituents independently selected from the group consisting of $C_{1-4}$-alkyl-O—, $F_3$CO—, $F_2$HCO—, $FH_2$CO—, cyano, halogen, $(C_{1-4}$-alkyl$)_2$N—C(O)—, and $C_{1-6}$-alkyl- which is optionally fluorinated with 1 to 13 fluorine atoms, or $R^{4b}$ and $R^{5b}$ form together with the nitrogen atom to which they are attached a 4-12-membered mono-, bicyclic or bridged ring system optionally containing one double bond and/or one aromatic ring and optionally containing one additional heteroatom selected from the group consisting of —O—, —N($R^6$)—, wherein 2 geminal hydrogen atoms of the 4-12-membered mono- or bicyclic ring may be replaced by a —(CH$_2$)$_{1-5}$— group and wherein one —(CH$_2$)— group of the —(CH$_2$)$_{1-5}$— group may be replaced by —O— or —N($R^6$)— and wherein above mentioned 4-12-membered mono-, bicyclic or bridged ring system may optionally be substituted with 1 or 2 substituents independently selected from the group consisting of fluoro, aryl, heteroaryl, $C_{1-6}$-alkyl- which is optionally fluorinated with 1 to 13 fluorine atoms, heterocyclyl, HO—, oxo, $C_{1-6}$-alkyl-O—, $C_{3-6}$-cycloalkyl-O—, HO—$C_{1-4}$-alkyl-, $C_{1-4}$-alkyl-O—$C_{1-4}$-alkyl-, heterocyclyl-O— and $(R^6)_2$N—, wherein the directly above mentioned aryl and heteroaryl groups may optionally be substituted with 1 to 3 substituents independently selected from the group consisting of $C_{1-4}$-alkyl-O—, $F_3$CO—, $F_2$HCO—, $FH_2$CO—, cyano, halogen, $(C_{1-4}$-alkyl$)_2$ N—C(O)— and $C_{1-6}$-alkyl- which is optionally fluorinated with 1 to 13 fluorine atoms.

In a further embodiment of the present invention $R^4$, $R^5$ are selected independently of each other from the group $R^{4c}/R^{5c}$ consisting of H, $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl-, tetrahydropyranyl-$C_{1-3}$-alkyl-, phenyl, phenyl-$C_{1-3}$-alkyl-, phenyl-O—$C_{2-3}$-alkyl-, triazolyl-$C_{1-3}$-alkyl-, pyrazolyl-$C_{1-3}$-alkyl-, oxazolyl-$C_{1-3}$-alkyl-, isoxazolyl-$C_{1-3}$-alkyl-, oxadiazolyl-$C_{1-3}$-alkyl-, thiazolyl-$C_{1-3}$-alkyl-, pyridinyl-$C_{1-3}$-alkyl-, pyrazinyl-$C_{1-3}$-alkyl-, pyridazinyl-$C_{1-3}$-alkyl-, pyrimidinyl-$C_{1-3}$-alkyl-, triazinyl-$C_{1-3}$-alkyl-, wherein above mentioned $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl-, tetrahydropyranyl-$C_{1-3}$-alkyl- or oxazepanyl-$C_{1-3}$-alkyl- groups may optionally be substituted with 1 to 3 substituents independently selected from the group consisting of fluoro, HO—, oxo, $C_{1-4}$-alkyl-O—, HO—$C_{1-4}$-alkyl-, $C_{1-4}$-alkyl-O—$C_{1-4}$-alkyl-, morpholinyl, oxetanyl, tetrahydrofuryl, tetrahydropyranyl, $(C_{1-3}$-alkyl$)_2$N—C(O)—, and $C_{1-6}$-alkyl- which is optionally fluorinated with 1 to 13 fluorine atoms, wherein above mentioned phenyl-, phenyl-$C_{1-3}$-alkyl-, phenyl-O—$C_{2-3}$-alkyl-, triazolyl-$C_{1-3}$-alkyl-, pyrazolyl-$C_{1-3}$-alkyl-, oxazolyl-$C_{1-3}$-alkyl-, isoxazolyl-$C_{1-3}$-alkyl-, oxadiazolyl-$C_{1-3}$-alkyl-, thiazolyl-$C_{1-3}$-alkyl-, pyridinyl-$C_{1-3}$-alkyl-, pyrazinyl-$C_{1-3}$-alkyl-, pyridazinyl-$C_{1-3}$-alkyl-, pyrimidinyl-$C_{1-3}$-alkyl-, and triazinyl-$C_{1-3}$-alkyl- groups may optionally be substituted with 1 to 3 substituents independently selected from the group consisting of $C_{1-3}$-alkyl-, $F_3$C—, $C_{1-4}$-alkyl-O—, $F_3$CO—, $F_2$HCO—, $FH_2$CO—, cyano and halogen, or $R^{4c}$ and $R^{5c}$ form together with the nitrogen atom to which they are attached a 4-11-membered mono-, bicyclic or bridged ring system optionally containing one aromatic ring and optionally one additional heteroatom selected from the group consisting of —O—, —N($R^6$)—, wherein 2 geminal hydrogen atoms of the 4-11-membered saturated mono- or bicyclic ring may be replaced by a —(CH$_2$)$_{1-5}$— group and wherein one —(CH$_2$)— group of the —(CH$_2$)$_{1-5}$— group may be replaced by —O— or —N($R^6$)— and wherein above mentioned 4-11-membered mono-, bicyclic or bridged ring system may optionally be substituted with 1 or 2 substituents independently selected from the group consisting of fluoro, aryl, heteroaryl, $C_{1-6}$-alkyl- which is optionally fluorinated with 1 to 13 fluorine atoms, heterocyclyl, HO—, oxo, $C_{1-6}$-alkyl-O—, $C_{3-6}$-cycloalkyl-O—, HO—$C_{1-4}$-alkyl-, $C_{1-4}$-alkyl-O—$C_{1-4}$-alkyl-, heterocyclyl-O—, $(R^6)_2$N—;

wherein the directly above mentioned aryl and heteroaryl groups may optionally be substituted with 1 to 3 substituents independently selected from the group consisting of $C_{1-4}$-alkyl-O—, $F_3$CO—, $F_2$HCO—, $FH_2$CO—, cyano, halogen, $(C_{1-4}$-alkyl$)_2$ N—C(O)— and $C_{1-6}$-alkyl- which is optionally fluorinated with 1 to 13 fluorine atoms.

In a further embodiment of the present invention $R^4$, $R^5$ are selected independently of each other from the group $R^{4d}/R^{5d}$ consisting of H, $C_{1-6}$-alkyl-, $C_{3-7}$-cycloalkyl-, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl-, tetrahydropyranyl-$C_{1-3}$-alkyl-, phenyl, phenyl-$C_{1-3}$-alkyl-, phenyl-O—$C_{2-3}$-alkyl-, triazolyl-$C_{1-3}$-alkyl-, pyrazolyl-$C_{1-3}$-alkyl-, oxazolyl-$C_{1-3}$-alkyl-, isoxazolyl-$C_{1-3}$-alkyl-, oxadiazolyl-$C_{1-3}$-alkyl-, thiazolyl-$C_{1-3}$-alkyl-, pyridinyl-$C_{1-3}$-alkyl-, pyrazinyl-$C_{1-3}$-alkyl-, pyridazinyl-$C_{1-3}$-alkyl-, pyrimidinyl-$C_{1-3}$-alkyl-, triazinyl-$C_{1-3}$-alkyl-, wherein above mentioned $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$- alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl- or tetrahydropyranyl-$C_{1-3}$-alkyl- groups may optionally be substituted with 1 to 3 substituents independently selected from the group consisting of fluoro, HO—, oxo, $C_{1-4}$-alkyl-O—, HO—$C_{1-4}$-alkyl-, $C_{1-4}$-alkyl-O—$C_{1-4}$-alkyl-, oxetanyl, tetrahydrofuryl, tetrahydropyranyl, and $C_{1-6}$-alkyl- which is optionally fluorinated with 1 to 13 fluorine atoms, wherein above mentioned phenyl-, phenyl-$C_{1-3}$-alkyl-, phenyl-O—$C_{2-3}$-alkyl-, triazolyl-$C_{1-3}$-alkyl-, pyrazolyl-$C_{1-3}$-alkyl-, oxazolyl-$C_{1-3}$-alkyl-, isoxazolyl-$C_{1-3}$-alkyl-, oxadiazolyl-$C_{1-3}$-alkyl-, thiazolyl-$C_{1-3}$-alkyl-, pyridinyl-$C_{1-3}$-alkyl-, pyrazinyl-$C_{1-3}$-alkyl-, pyridazinyl-$C_{1-3}$-alkyl- pyrimidinyl-$C_{1-3}$-alkyl- and triazinyl-$C_{1-3}$-alkyl- groups may optionally be substituted with 1 to 3 substituents independently selected from the group consisting of $C_{1-3}$-alkyl-, $F_3C$—, $C_{1-4}$-alkyl-O—, $F_3CO$—, $F_2HCO$—, $FH_2CO$—, cyano and halogen, or $R^{4d}$ and $R^{5d}$ form together with the nitrogen atom to which they are attached a ring system selected from the group consisting of,

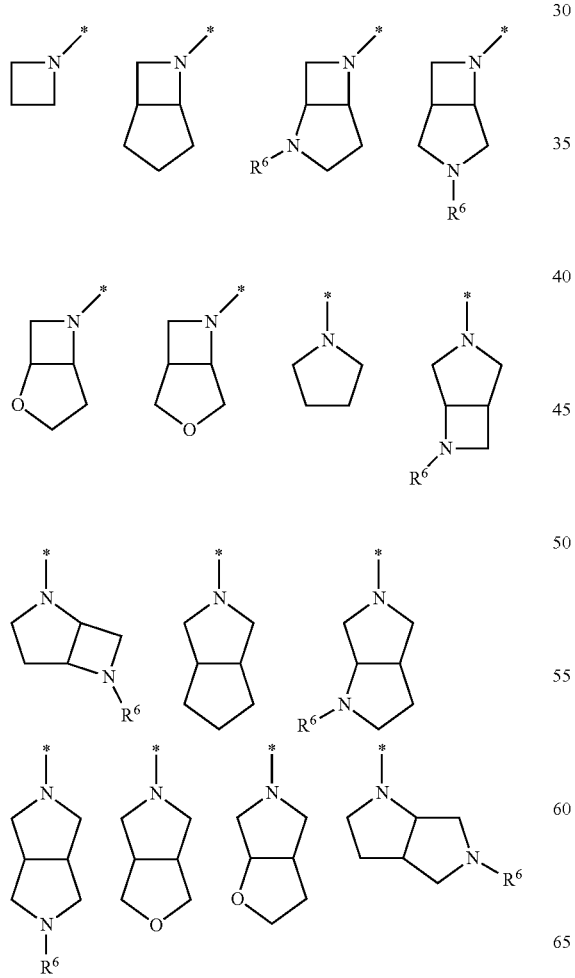

-continued

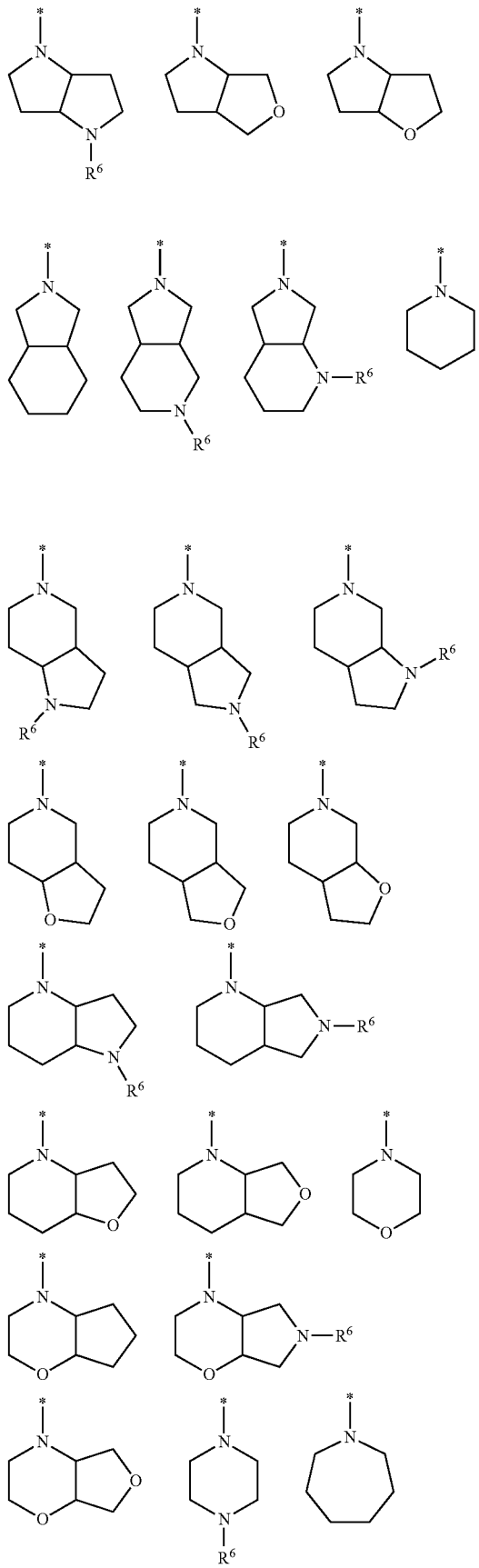

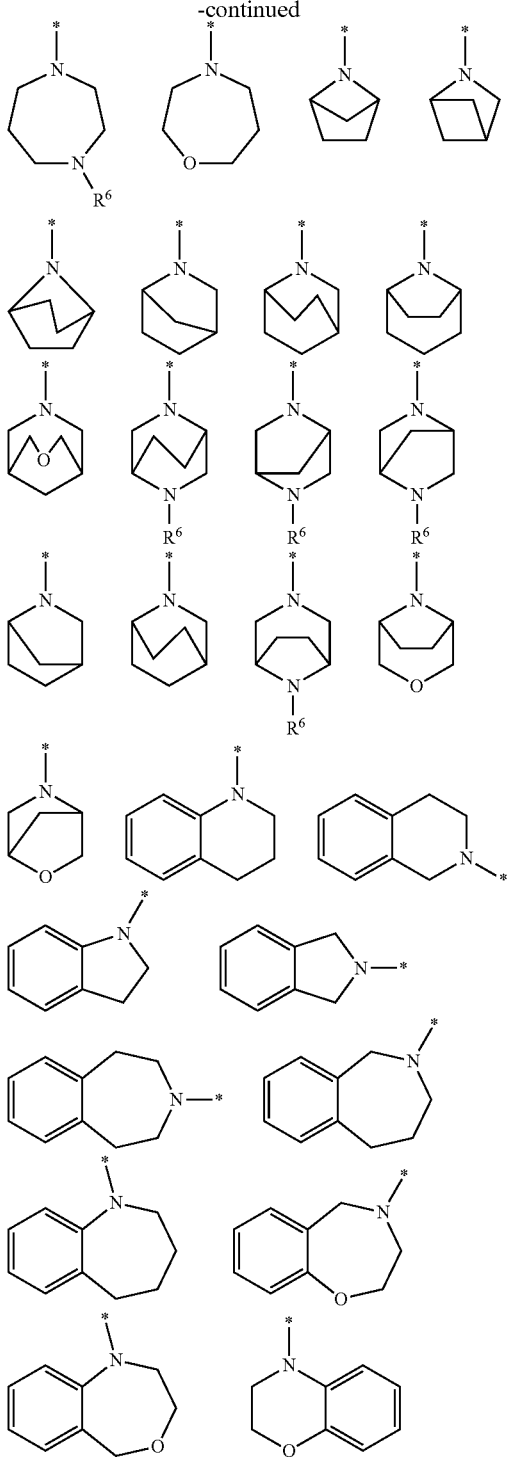

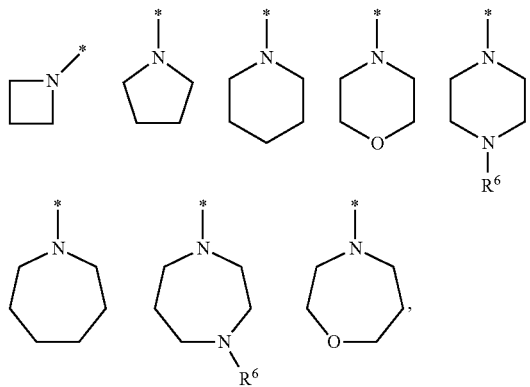

wherein 2 geminal hydrogen atoms of the above mentioned mono- or bicyclic ring may be replaced by a —(CH$_2$)$_{3-5}$— group and
wherein one —(CH$_2$)— group of the —(CH$_2$)$_{3-5}$— group may be replaced by —O— or —N(R$^6$)— and
wherein above mentioned mono- or bicyclic ring may optionally be substituted with 1 or 2 substituents independently selected from the group consisting of fluoro, phenyl, C$_{1-6}$-alkyl- which is optionally fluorinated with 1 to 13 fluorine atoms, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, HO—, oxo, C$_{1-6}$-alkyl-O—, C$_{3-6}$-cycloalkyl-O—, HO—C$_{1-4}$-alkyl-, C$_{1-4}$-alkyl-O—C$_{1-4}$-alkyl-, oxetanyl-O—, tetrahydrofuryl-O—, tetrahydropyranyl-O— and (R$^6$)$_2$N—
wherein the aforementioned phenyl groups may optionally be substituted with 1 to 3 substituents independently selected from the group consisting of F$_3$C—, C$_{1-4}$-alkyl-O—, F$_3$CO—, F$_2$HCO—, FH$_2$CO—, cyano, halogen, and C$_{1-3}$-alkyl-.

In a further embodiment of the present invention
R$^4$, R$^5$ are selected independently of each other from the group R$^{4e}$/R$^{5e}$ consisting of
H, C$_{1-6}$-alkyl-, C$_{3-7}$-cycloalkyl, C$_{3-7}$-cycloalkyl-C$_{1-3}$-alkyl-, C$_{3-7}$-cycloalkyl-O—C$_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-C$_{1-3}$-alkyl-, pyrrolidinyl-C$_{1-3}$-alkyl-, piperidinyl-C$_{1-3}$-alkyl-, piperazinyl-C$_{1-3}$-alkyl-, oxetanyl-C$_{1-3}$-alkyl-, tetrahydrofuryl-C$_{1-3}$-alkyl-, tetrahydropyranyl-C$_{1-3}$-alkyl-,
wherein above mentioned C$_{1-6}$-alkyl-, C$_{3-7}$-cycloalkyl, C$_{3-7}$-cycloalkyl-C$_{1-3}$-alkyl-, C$_{3-7}$-cycloalkyl-O—C$_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-C$_{1-3}$-alkyl-, pyrrolidinyl-C$_{1-3}$-alkyl-, piperidinyl-C$_{1-3}$-alkyl-, piperazinyl-C$_{1-3}$-alkyl-, oxetanyl-C$_{1-3}$-alkyl-, tetrahydrofuryl-C$_{1-3}$-alkyl-, tetrahydropyranyl-C$_{1-3}$-alkyl-groups may optionally be substituted with 1 to 3 substituents independently selected from the group consisting of fluoro, HO—, oxo, C$_{1-4}$-alkyl-O—, HO—C$_{1-4}$-alkyl-, C$_{1-4}$-alkyl-O—C$_{1-4}$-alkyl- and C$_{1-3}$-alkyl- which is optionally fluorinated with 1 to 7 fluorine atoms,
or
R$^{4e}$ and R$^{5e}$ form together with the nitrogen atom to which they are attached a ring system selected from the group consisting of wherein above mentioned monocyclic rings may optionally be substituted with 1 or 2 substituents independently selected from the group consisting of fluoro, C$_{1-3}$-alkyl- which is optionally fluorinated with 1 to 7 fluorine atoms, HO—, oxo, $C_{1-6}$-alkyl-O—, $C_{3-6}$-cycloalkyl-O—, HO—$C_{1-4}$-alkyl- and $C_{1-4}$-alkyl-O—$C_{1-4}$-alkyl-.

In a further embodiment of the present invention $R^4$, $R^5$ are selected independently of each other from the group $R^{4f}/R^{5f}$ consisting of H and $C_{1-5}$-alkyl- which is optionally fluorinated with 1 to 13 fluorine atoms.

In a further embodiment of the present invention $R^6$ is selected independently of each other from the group $R^{6b}$ consisting of H, $C_{1-6}$-alkyl-, $C_{3-6}$-cycloalkyl, oxetanyl, tetrahydrofuryl, tetrahydropyranyl, pyridinyl, pyrimidinyl, pyridazinyl, pyrazinyl, triazinyl, thiazolyl, oxadiazolyl, oxazolyl, HC(O)—, $C_{1-6}$-alkyl-C(O)—, $C_{3-6}$-cycloalkyl-C(O)—, phenyl-C(O)—, $C_{1-4}$-alkyl-O—C(O)— and ($C_{1-4}$-alkyl)$_2$N—C(O)—,
  wherein above mentioned $C_{1-6}$-alkyl-, $C_{3-6}$-cycloalkyl-, $C_{1-6}$-alkyl-C(O)— and $C_{3-6}$-cycloalkyl-C(O)— groups may optionally be substituted with 1-13 fluorine atoms,
  wherein the aforementioned phenyl-C(O)—, pyridinyl, pyrimidinyl, pyridazinyl, pyrazinyl, triazinyl, thiazolyl oxadiazolyl and oxazolyl groups may optionally be substituted with 1 to 3 substituents independently selected from the group consisting of $C_{1-4}$-alkyl-O—, $F_3C$—, $F_3CO$—, $F_2HCO$—, $FH_2CO$—, cyano, halogen, and $C_{1-3}$-alkyl-.

In a further embodiment of the present invention $R^6$ is selected independently of each other from the group $R^{ho}$ consisting of H and $C_{1-5}$-alkyl- which is optionally fluorinated with 1 to 13 fluorine atoms.

In a further embodiment of the present invention $R^7$ is selected from the group $R^{7b}$ consisting of H.

Each $R^{1x}$, $R^{2x}$, $R^{3x}$, $R^{4x/5x}$, $R^{6x}$, $R^{7x}$, $A^x$, $B^x$, $D^x$, and $W^x$ represents a characterized, individual embodiment for the corresponding substituent as described above. Thus given the above definitions, preferred individual embodiments of the first aspect of the invention are fully characterized by the term ($R^{1x}$, $R^{2x}$, $R^{3x}$, $R^{4x/5x}$, $R^{6x}$, $R^{7x}$, $A^x$, $B^x$, $D^x$, and $W^x$), wherein for each index x an individual figure is given that ranges from "a" to the highest letter given above. All individual embodiments described by the term in parentheses with full permutation of the indices x, referring to the definitions above, shall be comprised by the present invention.

The following Table 1 shows, exemplarily and in the order of increasing preference from the first line to the last line, such embodiments E-1 to E-40 of the invention that are considered preferred. This means that embodiment E-40, represented by the entries in the last row of Table 1, is the most preferred embodiment.

TABLE 1

Preferred embodiments E-1 to E-40 of the invention

| | $A^x$ | $B^x$ | $D^x$ | $W^x$ | $R^{1x}$ | $R^{2x}$ | $R^{3x}$ | $R^{4x}/R^{5x}$ | $R^{6x}$ | $R^{7x}$ |
|---|---|---|---|---|---|---|---|---|---|---|
| E-1 | $A^b$ | $B^b$ | $D^b$ | $W^a$ | $R^{1b}$ | $R^{2b}$ | $R^{3b}$ | $R^{4b}/R^{5b}$ | $R^{6b}$ | $R^{7a}$ |
| E-2 | $A^b$ | $B^b$ | $D^c$ | $W^a$ | $R^{1b}$ | $R^{2b}$ | $R^{3b}$ | $R^{4b}/R^{5b}$ | $R^{6b}$ | $R^{7a}$ |
| E-3 | $A^b$ | $B^b$ | $D^d$ | $W^b$ | $R^{1b}$ | $R^{2c}$ | $R^{3b}$ | $R^{4c}/R^{5c}$ | $R^{6b}$ | $R^{7a}$ |
| E-4 | $A^b$ | $B^b$ | $D^d$ | $W^b$ | $R^{1b}$ | $R^{2c}$ | $R^{3b}$ | $R^{4d}/R^{5d}$ | $R^{6c}$ | $R^{7b}$ |
| E-5 | $A^b$ | $B^b$ | $D^d$ | $W^b$ | $R^{1b}$ | $R^{2c}$ | $R^{3b}$ | $R^{4e}/R^{5e}$ | — | $R^{7b}$ |
| E-6 | $A^b$ | $B^b$ | $D^d$ | $W^b$ | $R^{1b}$ | $R^{2c}$ | $R^{3b}$ | $R^{4f}/R^{5f}$ | — | $R^{7b}$ |
| E-7 | $A^c$ | $B^c$ | $D^e$ | $W^b$ | $R^{1b}$ | $R^{2b}$ | $R^{3b}$ | $R^{4b}/R^{5b}$ | $R^{6b}$ | $R^{7a}$ |
| E-8 | $A^c$ | $B^c$ | $D^e$ | $W^b$ | $R^{1b}$ | $R^{2b}$ | $R^{3b}$ | $R^{4c}/R^{5c}$ | $R^{6c}$ | $R^{7b}$ |
| E-9 | $A^c$ | $B^c$ | $D^e$ | $W^b$ | $R^{1c}$ | $R^{2c}$ | $R^{3b}$ | $R^{4d}/R^{5d}$ | $R^{6c}$ | $R^{7a}$ |
| E-10 | $A^c$ | $B^c$ | $D^e$ | $W^b$ | $R^{1c}$ | $R^{2c}$ | $R^{3b}$ | $R^{4e}/R^{5e}$ | — | $R^{7b}$ |

TABLE 1-continued

Preferred embodiments E-1 to E-40 of the invention

| | $A^x$ | $B^x$ | $D^x$ | $W^x$ | $R^{1x}$ | $R^{2x}$ | $R^{3x}$ | $R^{4x}/R^{5x}$ | $R^{6x}$ | $R^{7x}$ |
|---|---|---|---|---|---|---|---|---|---|---|
| E-11 | $A^d$ | $B^c$ | $D^f$ | $W^b$ | $R^{1c}$ | $R^{2c}$ | $R^{3c}$ | — | — | $R^{7b}$ |
| E-12 | $A^d$ | $B^c$ | $D^g$ | $W^b$ | $R^{1c}$ | $R^{2c}$ | $R^{3c}$ | — | — | $R^{7b}$ |
| E-13 | $A^d$ | $B^c$ | $D^h$ | $W^b$ | $R^{1c}$ | $R^{2c}$ | $R^{3c}$ | — | — | $R^{7b}$ |
| E-14 | $A^d$ | $B^c$ | $D^f$ | $W^b$ | $R^{1d}$ | $R^{2c}$ | $R^{3c}$ | — | — | $R^{7b}$ |
| E-15 | $A^d$ | $B^c$ | $D^g$ | $W^b$ | $R^{1e}$ | $R^{2d}$ | $R^{3d}$ | — | — | $R^{7b}$ |
| E-16 | $A^d$ | $B^c$ | $D^h$ | $W^b$ | $R^{1f}$ | $R^{2e}$ | $R^{3e}$ | — | — | $R^{7b}$ |
| E-17 | $A^e$ | $B^c$ | $D^f$ | $W^b$ | $R^{1c}$ | $R^{2c}$ | $R^{3c}$ | — | — | $R^{7b}$ |
| E-18 | $A^e$ | $B^c$ | $D^g$ | $W^b$ | $R^{1c}$ | $R^{2c}$ | $R^{3c}$ | — | — | $R^{7b}$ |
| E-19 | $A^e$ | $B^c$ | $D^h$ | $W^b$ | $R^{1c}$ | $R^{2c}$ | $R^{3c}$ | — | — | $R^{7b}$ |
| E-20 | $A^e$ | $B^c$ | $D^f$ | $W^b$ | $R^{1d}$ | $R^{2c}$ | $R^{3c}$ | — | — | $R^{7b}$ |
| E-21 | $A^e$ | $B^c$ | $D^g$ | $W^b$ | $R^{1d}$ | $R^{2c}$ | $R^{3c}$ | — | — | $R^{7b}$ |
| E-22 | $A^e$ | $B^c$ | $D^h$ | $W^b$ | $R^{1d}$ | $R^{2c}$ | $R^{3c}$ | — | — | $R^{7b}$ |
| E-23 | $A^e$ | $B^c$ | $D^f$ | $W^b$ | $R^{1e}$ | $R^{2c}$ | $R^{3c}$ | — | — | $R^{7b}$ |
| E-24 | $A^e$ | $B^c$ | $D^g$ | $W^b$ | $R^{1e}$ | $R^{2c}$ | $R^{3c}$ | — | — | $R^{7b}$ |
| E-25 | $A^e$ | $B^c$ | $D^h$ | $W^b$ | $R^{1e}$ | $R^{2c}$ | $R^{3c}$ | — | — | $R^{7b}$ |
| E-26 | $A^e$ | $B^c$ | $D^f$ | $W^b$ | $R^{1f}$ | $R^{2c}$ | $R^{3c}$ | — | — | $R^{7b}$ |
| E-27 | $A^e$ | $B^c$ | $D^g$ | $W^b$ | $R^{1f}$ | $R^{2c}$ | $R^{3c}$ | — | — | $R^{7b}$ |
| E-28 | $A^e$ | $B^c$ | $D^h$ | $W^b$ | $R^{1f}$ | $R^{2c}$ | $R^{3c}$ | — | — | $R^{7b}$ |
| E-29 | $A^e$ | $B^c$ | $D^f$ | $W^b$ | $R^{1f}$ | $R^{2d}$ | $R^{3c}$ | — | — | $R^{7b}$ |
| E-30 | $A^e$ | $B^c$ | $D^g$ | $W^b$ | $R^{1f}$ | $R^{2d}$ | $R^{3c}$ | — | — | $R^{7b}$ |
| E-31 | $A^e$ | $B^c$ | $D^h$ | $W^b$ | $R^{1f}$ | $R^{2d}$ | $R^{3c}$ | — | — | $R^{7b}$ |
| E-32 | $A^e$ | $B^c$ | $D^f$ | $W^b$ | $R^{1f}$ | $R^{2e}$ | $R^{3c}$ | — | — | $R^{7b}$ |
| E-33 | $A^e$ | $B^c$ | $D^f$ | $W^b$ | $R^{1f}$ | $R^{2e}$ | $R^{3d}$ | — | — | $R^{7b}$ |
| E-34 | $A^e$ | $B^c$ | $D^f$ | $W^b$ | $R^{1f}$ | $R^{2e}$ | $R^{3e}$ | — | — | $R^{7b}$ |
| E-35 | $A^e$ | $B^c$ | $D^g$ | $W^b$ | $R^{1f}$ | $R^{2e}$ | $R^{3c}$ | — | — | $R^{7b}$ |
| E-36 | $A^e$ | $B^c$ | $D^g$ | $W^b$ | $R^{1f}$ | $R^{2e}$ | $R^{3d}$ | — | — | $R^{7b}$ |
| E-37 | $A^e$ | $B^c$ | $D^g$ | $W^b$ | $R^{1f}$ | $R^{2e}$ | $R^{3e}$ | — | — | $R^{7b}$ |
| E-38 | $A^e$ | $B^c$ | $D^h$ | $W^b$ | $R^{1f}$ | $R^{2e}$ | $R^{3c}$ | — | — | $R^{7b}$ |
| E-39 | $A^e$ | $B^c$ | $D^h$ | $W^b$ | $R^{1f}$ | $R^{2e}$ | $R^{3d}$ | — | — | $R^{7b}$ |
| E-40 | $A^e$ | $B^c$ | $D^h$ | $W^b$ | $R^{1f}$ | $R^{2e}$ | $R^{3e}$ | — | — | $R^{7b}$ | the tautomers thereof, the stereoisomers thereof, the mixtures thereof, and the salts thereof.

Accordingly, for example E-40 covers compounds of formula I, wherein

A is selected from the group $A^e$ consisting of

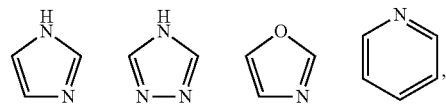

wherein above mentioned groups may optionally be substituted with 1 or 2 substituents independently selected from the group consisting of halogen and $C_{1-3}$-alkyl- which is optionally fluorinated with 1 to 7 fluorine atoms;

B is selected from the group $B^c$ consisting of

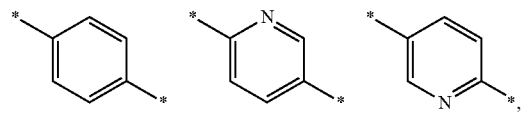

wherein above mentioned phenyl- and pyridinyl- groups may optionally be substituted with 1 or 2 substituents independently selected from the group consisting of halogen, cyano, $C_{1-3}$-alkyl- which is optionally fluorinated with 1 to 7 fluorine atoms, and $C_{1-3}$-alkyl-O— which is optionally fluorinated with 1 to 7 fluorine atoms;

D is selected from the group $D^h$ consisting of

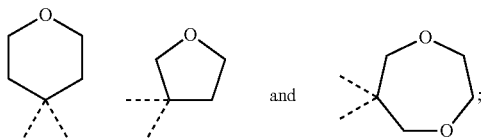

W is selected from the group $W^b$ consisting of
—($R^7$)N—;

$R^1$ is selected from the group $R^{1f}$ consisting of
H, $C_{1-4}$-alkyl-
wherein above mentioned $C_{1-8}$-alkyl-groups may optionally be substituted with 1 to 3 substituents independently selected from the group consisting of HO—, $C_{1-3}$-alkyl-O—, cyano, and halogen;

$R^2$ is selected from the group $R^{ee}$ consisting of
H, $C_{1-5}$-alkyl-, $C_{1-3}$-alkyl-O—$C_{1-3}$-alkyl-, cyclopropyl, phenyl,

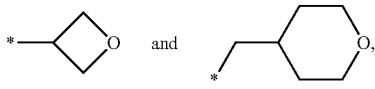

wherein above mentioned $C_{1-5}$-alkyl- and phenyl groups may optionally be substituted with 1 to 3 fluoroatoms;

$R^3$ is selected from the group $R^{3e}$ consisting of
H and $H_3C$—;

$R^7$ is selected from the group $R^{7b}$ consisting of
H;

the tautomers thereof, the stereoisomers thereof, the mixtures thereof, and the salts thereof.

Further preferred are the following compounds listed in table 2:

| No. | Structure |
|---|---|
| I | 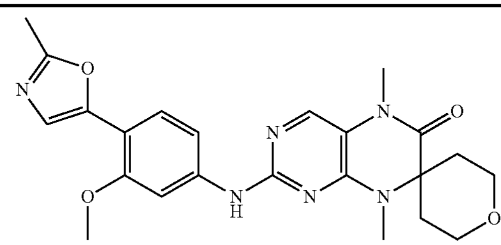 |
| II | 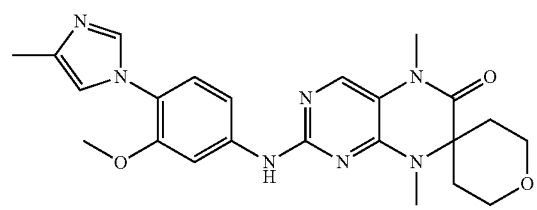 [SMILES: COc1cc(Nc2ncc3c(n2)N(C)C2(CCOCC2)C(=O)N3C)ccc1-n1cnc(C)c1] |
| III | 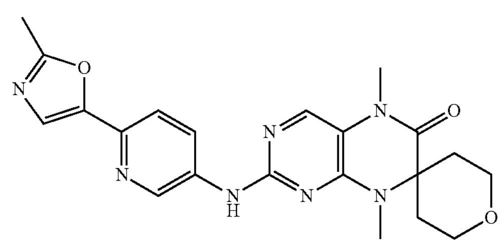 [SMILES: Cc1ncc(-c2ccc(Nc3ncc4c(n3)N(C)C3(CCOCC3)C(=O)N4C)cn2)o1] |
| IV | 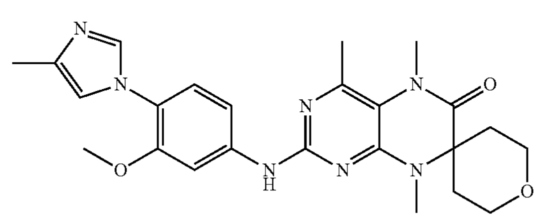 [SMILES: COc1cc(Nc2nc(C)c3c(n2)N(C)C2(CCOCC2)C(=O)N3C)ccc1-n1cnc(C)c1] |

| No. | Structure |
|---|---|
| V | 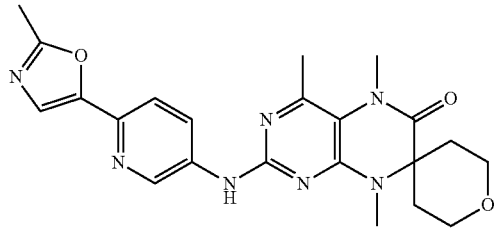 [SMILES: Cc1ncc(-c2ccc(Nc3nc(C)c4c(n3)N(C)C3(CCOCC3)C(=O)N4C)cn2)o1] |
| VI | 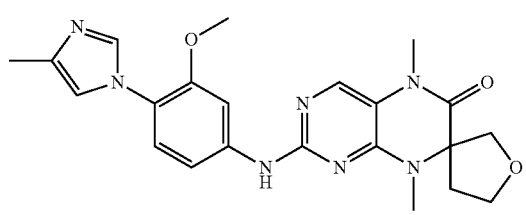 [SMILES: COc1cc(Nc2ncc3c(n2)N(C)C2(CCOC2)C(=O)N3C)ccc1-n1cnc(C)c1] |
| VII | 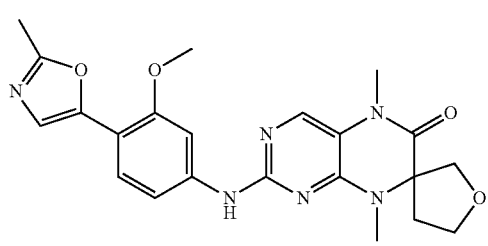 [SMILES: COc1cc(Nc2ncc3c(n2)N(C)C2(CCOC2)C(=O)N3C)ccc1-c1cnc(C)o1] |
| VIII | 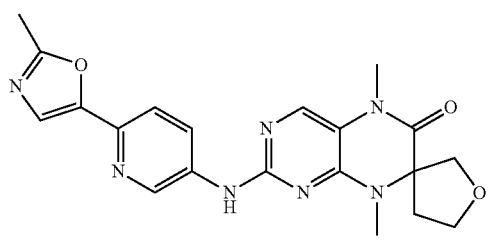 [SMILES: Cc1ncc(-c2ccc(Nc3ncc4c(n3)N(C)C3(CCOC3)C(=O)N4C)cn2)o1] |
| IX | 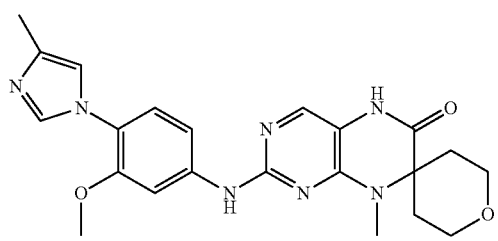 [SMILES: COc1cc(Nc2ncc3c(n2)N(C)C2(CCOCC2)C(=O)N3)ccc1-n1cnc(C)c1] |
| X | 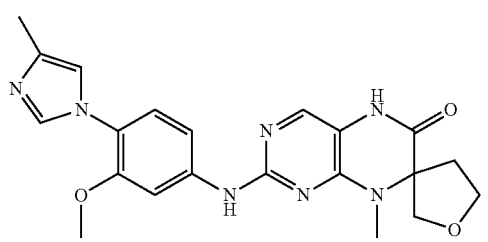 [SMILES: COc1cc(Nc2ncc3c(n2)N(C)C2(CCOC2)C(=O)N3)ccc1-n1cnc(C)c1] |

-continued
| No. | Structure |
|---|---|
| XI | 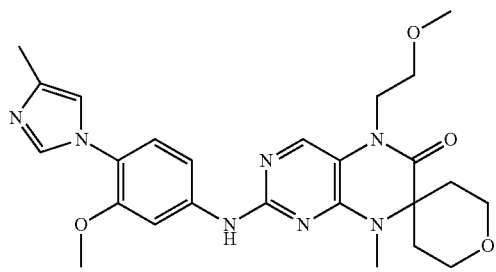 [SMILES: COCCN1C(=O)C2(CCOCC2)N(C)c2nc(Nc3ccc(-n4cnc(C)c4)c(OC)c3)ncc21] |
| XII | 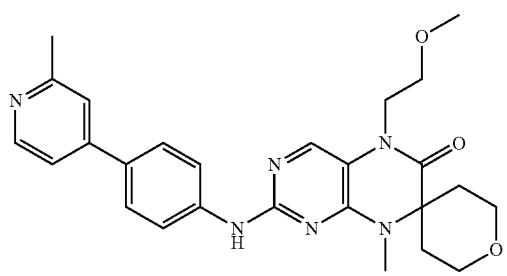 [SMILES: COCCN1C(=O)C2(CCOCC2)N(C)c2nc(Nc3ccc(-c4ccnc(C)c4)cc3)ncc21] |
| XIII | 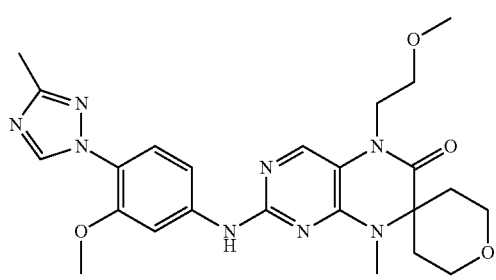 [SMILES: COCCN1C(=O)C2(CCOCC2)N(C)c2nc(Nc3ccc(-n4cnc(C)n4)c(OC)c3)ncc21] |
| XIV | 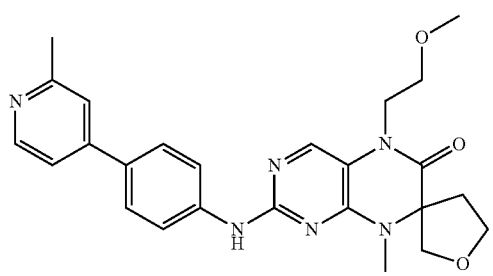 [SMILES: COCCN1C(=O)C2(CCOC2)N(C)c2nc(Nc3ccc(-c4ccnc(C)c4)cc3)ncc21] |
| XV | 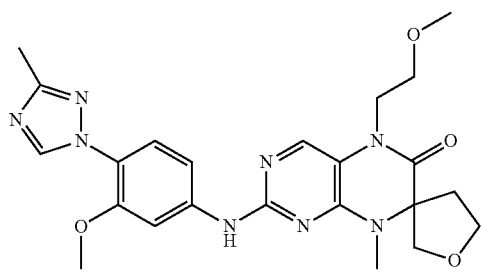 [SMILES: COCCN1C(=O)C2(CCOC2)N(C)c2nc(Nc3ccc(-n4cnc(C)n4)c(OC)c3)ncc21] |

-continued
| No. | Structure |
|---|---|
| XVI | 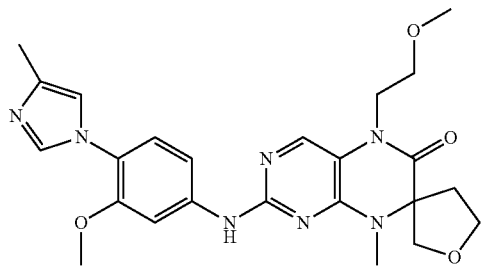 [SMILES: COCCN1C(=O)C2(CCOC2)N(C)c2nc(Nc3ccc(-n4cnc(C)c4)c(OC)c3)ncc21] |
| XVII | 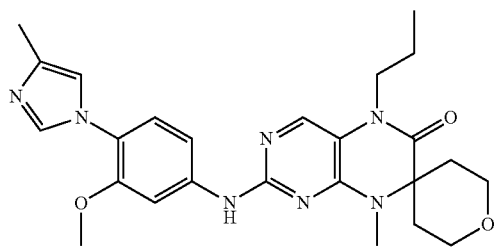 [SMILES: CCCN1C(=O)C2(CCOCC2)N(C)c2nc(Nc3ccc(-n4cnc(C)c4)c(OC)c3)ncc21] |
| XVIII | 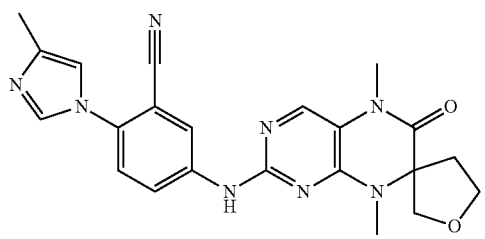 [SMILES: Cc1cn(-c2ccc(Nc3ncc4c(n3)N(C)C3(CCOC3)C(=O)N4C)cc2C#N)cn1] |
| XIX | 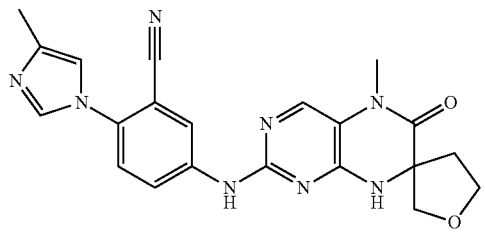 [SMILES: Cc1cn(-c2ccc(Nc3ncc4c(n3)NC3(CCOC3)C(=O)N4C)cc2C#N)cn1] |
| XX | 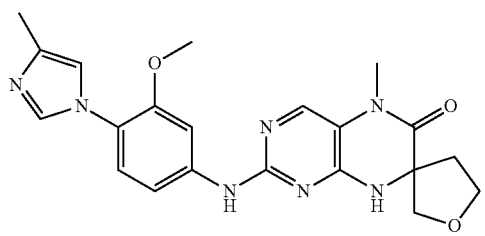 [SMILES: COc1cc(Nc2ncc3c(n2)NC2(CCOC2)C(=O)N3C)ccc1-n1cnc(C)c1] |
| XXI | 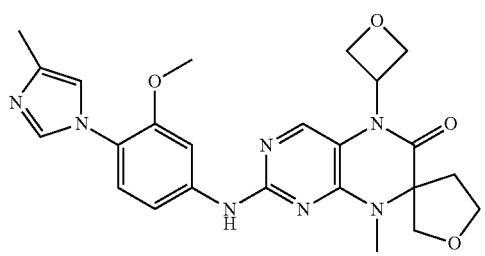 [SMILES: COc1cc(Nc2ncc3c(n2)N(C)C2(CCOC2)C(=O)N3C2COC2)ccc1-n1cnc(C)c1] |

| No. | Structure |
|---|---|
| XXII | 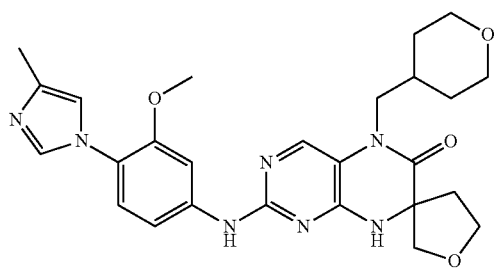 [SMILES: COc1cc(Nc2ncc3c(n2)NC2(CCOC2)C(=O)N3CC2CCOCC2)ccc1-n1cnc(C)c1] |
| XXIII | 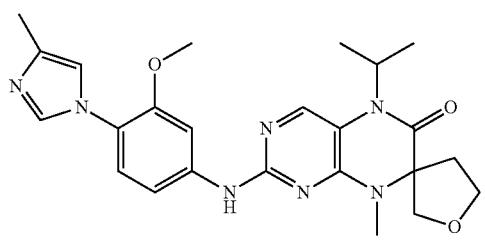 [SMILES: COc1cc(Nc2ncc3c(n2)N(C)C2(CCOC2)C(=O)N3C(C)C)ccc1-n1cnc(C)c1] |
| XXIV | 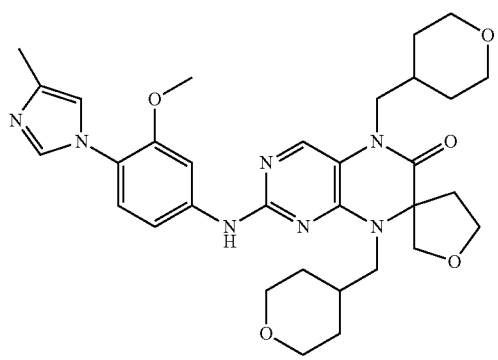 [SMILES: COc1cc(Nc2ncc3c(n2)N(CC2CCOCC2)C2(CCOC2)C(=O)N3CC2CCOCC2)ccc1-n1cnc(C)c1] |
| XXV | 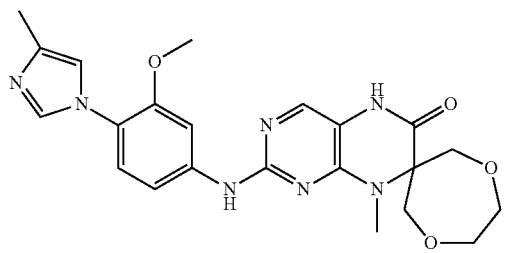 [SMILES: COc1cc(Nc2ncc3c(n2)N(C)C2(COCCOC2)C(=O)N3)ccc1-n1cnc(C)c1] |
| XXVI | 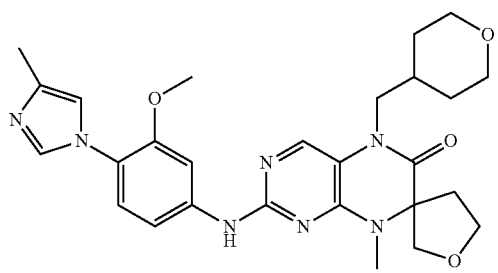 [SMILES: COc1cc(Nc2ncc3c(n2)N(C)C2(CCOC2)C(=O)N3CC2CCOCC2)ccc1-n1cnc(C)c1] |

| No. | Structure |
|---|---|
| XXVII | 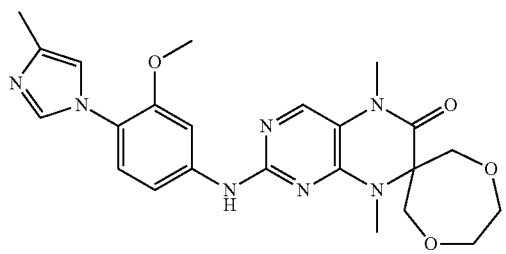 [SMILES: COc1cc(Nc2ncc3c(n2)N(C)C2(COCCOC2)C(=O)N3C)ccc1-n1cnc(C)c1] |
| XXVIII | 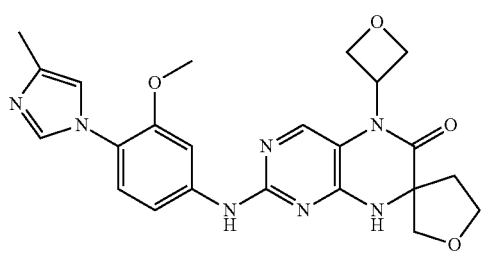 [SMILES: COc1cc(Nc2ncc3c(n2)NC2(CCOC2)C(=O)N3C2COC2)ccc1-n1cnc(C)c1] |
| XXIX | 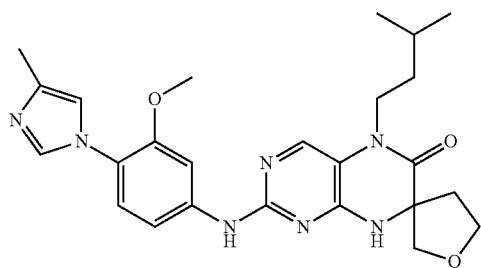 [SMILES: COc1cc(Nc2ncc3c(n2)NC2(CCOC2)C(=O)N3CCC(C)C)ccc1-n1cnc(C)c1] |
| XXX | 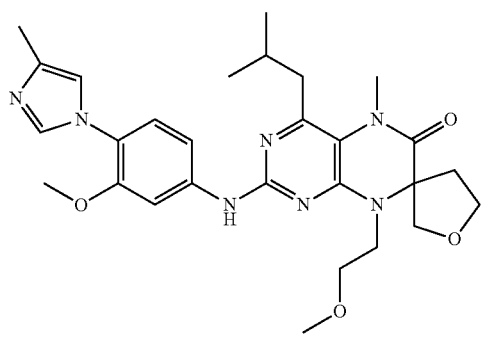 [SMILES: COCCN1c2nc(Nc3ccc(-n4cnc(C)c4)c(OC)c3)nc(CC(C)C)c2N(C)C(=O)C12CCOC2] |
| XXXI | 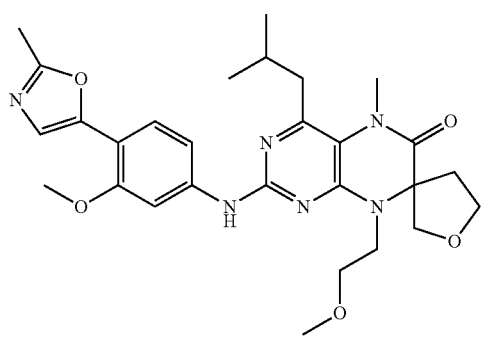 [SMILES: COCCN1c2nc(Nc3ccc(-c4cnc(C)o4)c(OC)c3)nc(CC(C)C)c2N(C)C(=O)C12CCOC2] |

| No. | Structure |
|---|---|
| XXXII | 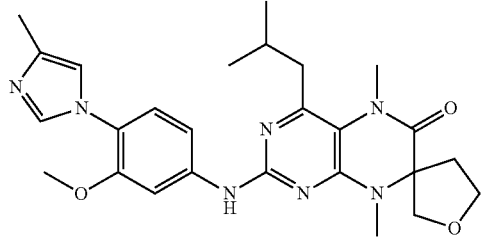 [SMILES: COc1cc(Nc2nc(CC(C)C)c3c(n2)N(C)C2(CCOC2)C(=O)N3C)ccc1-n1cnc(C)c1] |
| XXXIII | 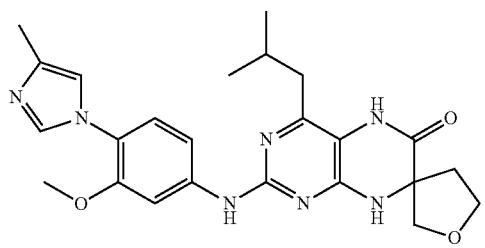 [SMILES: COc1cc(Nc2nc(CC(C)C)c3c(n2)NC2(CCOC2)C(=O)N3)ccc1-n1cnc(C)c1] |
| XXXIV | 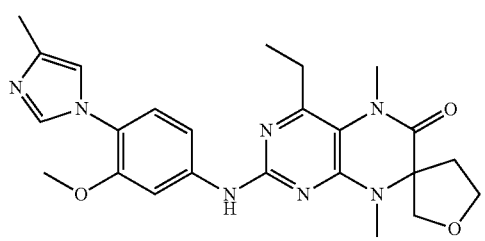 [SMILES: CCc1nc(Nc2ccc(-n3cnc(C)c3)c(OC)c2)nc2c1N(C)C(=O)C1(CCOC1)N2C] |
| XXXV | 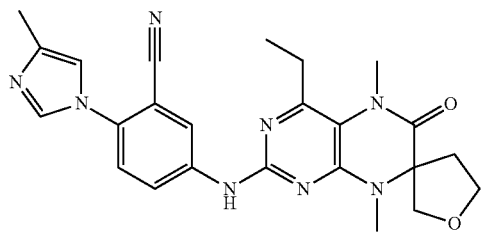 [SMILES: CCc1nc(Nc2ccc(-n3cnc(C)c3)c(C#N)c2)nc2c1N(C)C(=O)C1(CCOC1)N2C] |
| XXXVI | 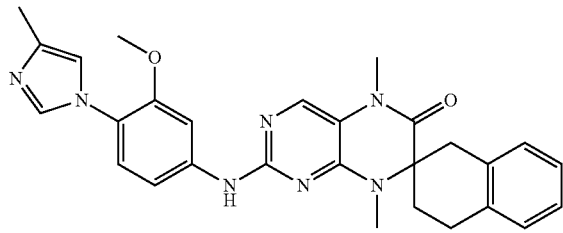 [SMILES: COc1cc(Nc2ncc3c(n2)N(C)C2(CCc4ccccc4C2)C(=O)N3C)ccc1-n1cnc(C)c1] |
| XXXVII | 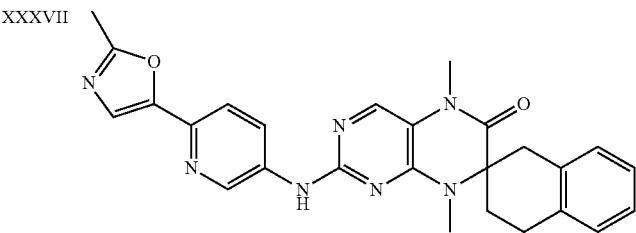 |

| No. | Structure |
|---|---|
| XXXVIII | 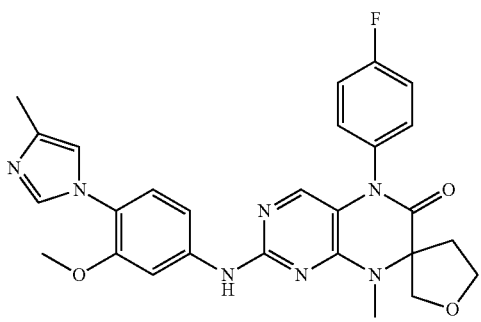 [SMILES: COc1cc(Nc2ncc3c(n2)N(C)C2(CCOC2)C(=O)N3c2ccc(F)cc2)ccc1-n1cnc(C)c1] |
| XXXIX | 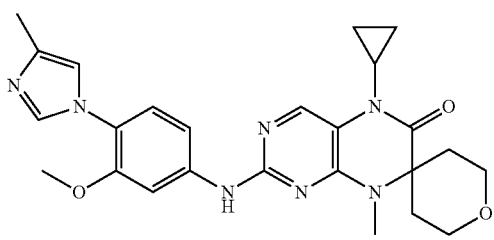 [SMILES: COc1cc(Nc2ncc3c(n2)N(C)C2(CCOCC2)C(=O)N3C2CC2)ccc1-n1cnc(C)c1] |
| XL | 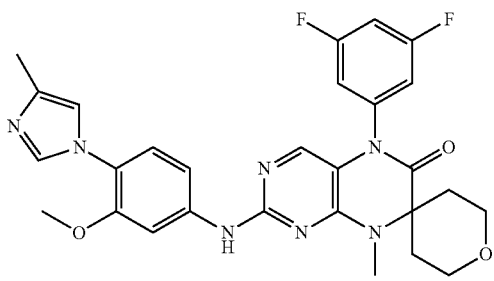 [SMILES: COc1cc(Nc2ncc3c(n2)N(C)C2(CCOCC2)C(=O)N3c2cc(F)cc(F)c2)ccc1-n1cnc(C)c1] |
| XLI | 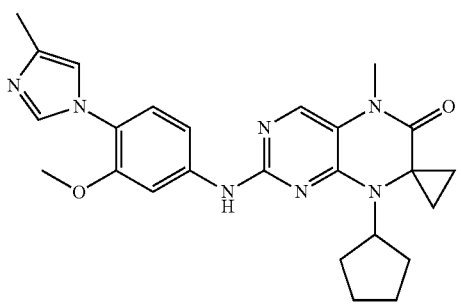 [SMILES: COc1cc(Nc2ncc3c(n2)N(C2CCCC2)C2(CC2)C(=O)N3C)ccc1-n1cnc(C)c1] |
| XLII | 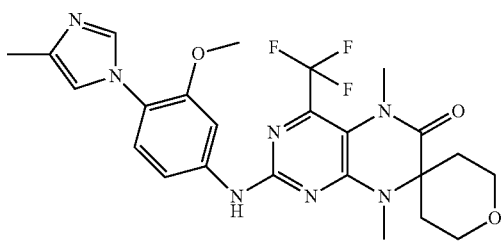 [SMILES: COc1cc(Nc2nc3c(c(C(F)(F)F)n2)N(C)C(=O)C2(CCOCC2)N3C)ccc1-n1cnc(C)c1] |

-continued
| No. | Structure |
|---|---|
| XLIII | 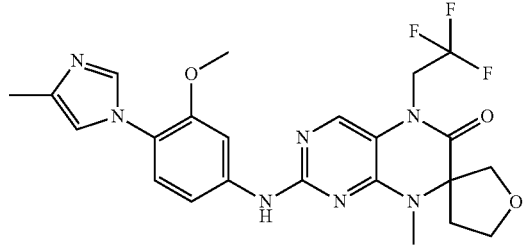 [SMILES: COc1cc(Nc2ncc3c(n2)N(C)C2(CCOC2)C(=O)N3CC(F)(F)F)ccc1-n1cnc(C)c1] |
| XLIV | 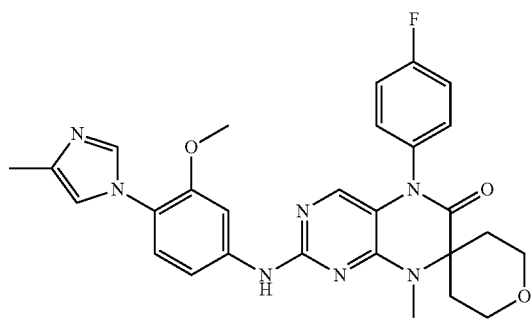 [SMILES: COc1cc(Nc2ncc3c(n2)N(C)C2(CCOCC2)C(=O)N3c2ccc(F)cc2)ccc1-n1cnc(C)c1] |
| XLV | 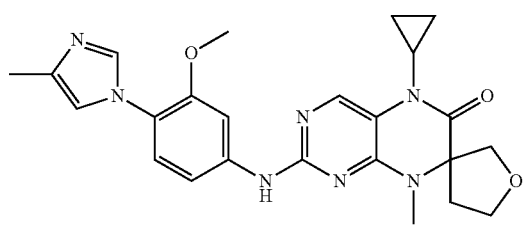 [SMILES: COc1cc(Nc2ncc3c(n2)N(C)C2(CCOC2)C(=O)N3C2CC2)ccc1-n1cnc(C)c1] |
| XLVI | 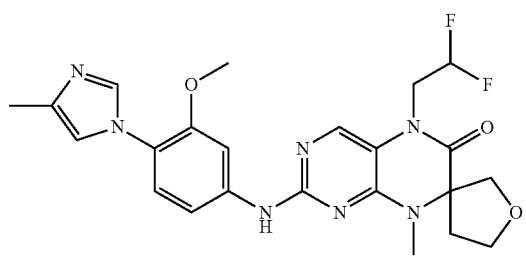 [SMILES: COc1cc(Nc2ncc3c(n2)N(C)C2(CCOC2)C(=O)N3CC(F)F)ccc1-n1cnc(C)c1] |
| XLVII | 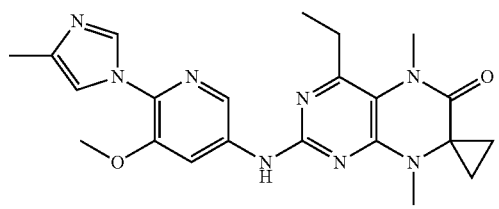 [SMILES: CCc1nc(Nc2cnc(-n3cnc(C)c3)c(OC)c2)nc2c1N(C)C(=O)C1(CC1)N2C] |
| XLVIII | 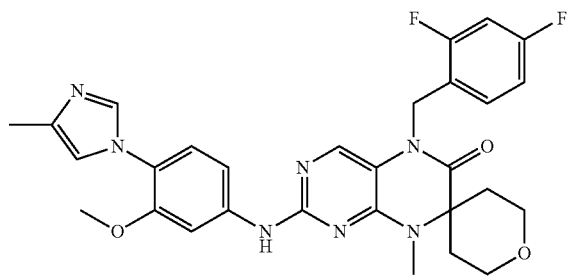 [SMILES: COc1cc(Nc2ncc3c(n2)N(C)C2(CCOCC2)C(=O)N3Cc2ccc(F)cc2F)ccc1-n1cnc(C)c1] |

| No. | Structure |
|---|---|
| XLIX | 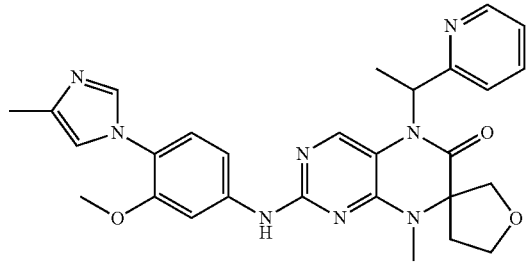 [SMILES: COc1cc(Nc2ncc3c(n2)N(C)C2(CCOC2)C(=O)N3C(C)c2ccccn2)ccc1-n1cnc(C)c1] |
| L | 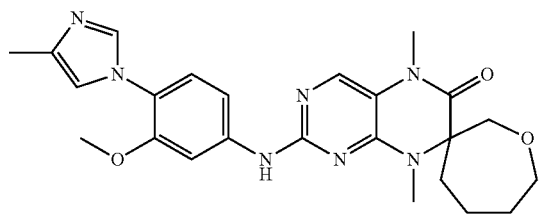 [SMILES: COc1cc(Nc2ncc3c(n2)N(C)C2(CCCCOC2)C(=O)N3C)ccc1-n1cnc(C)c1] |
| LI | 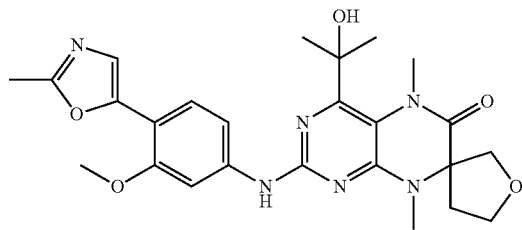 [SMILES: COc1cc(Nc2nc3c(c(C(C)(C)O)n2)N(C)C(=O)C2(CCOC2)N3C)ccc1-c1cnc(C)o1] |
| LII | 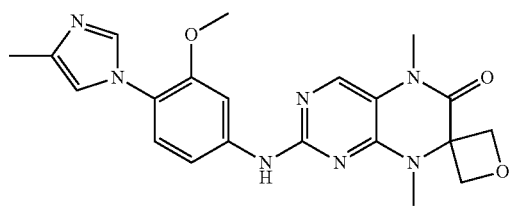 [SMILES: COc1cc(Nc2ncc3c(n2)N(C)C2(COC2)C(=O)N3C)ccc1-n1cnc(C)c1] |
| LIII | 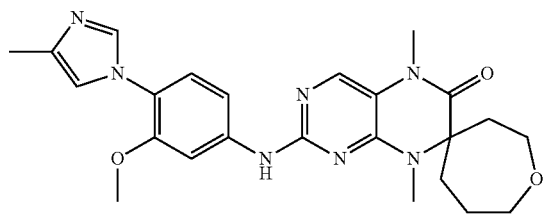 [SMILES: COc1cc(Nc2ncc3c(n2)N(C)C2(CCCOCC2)C(=O)N3C)ccc1-n1cnc(C)c1] |
| LIV | 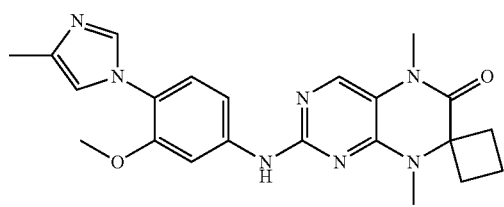 [SMILES: COc1cc(Nc2ncc3c(n2)N(C)C2(CCC2)C(=O)N3C)ccc1-n1cnc(C)c1] |

| No. | Structure |
|---|---|
| LV | 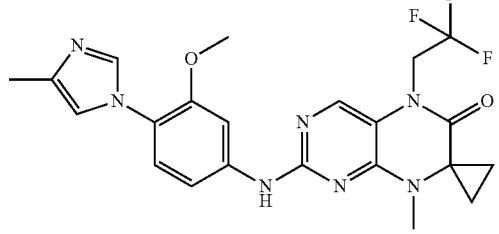 |
| LVI | 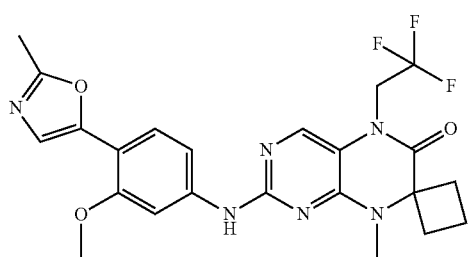 [SMILES: COc1cc(Nc2ncc3c(n2)N(C)C2(CCC2)C(=O)N3CC(F)(F)F)ccc1-c1cnc(C)o1] |
| LVII | 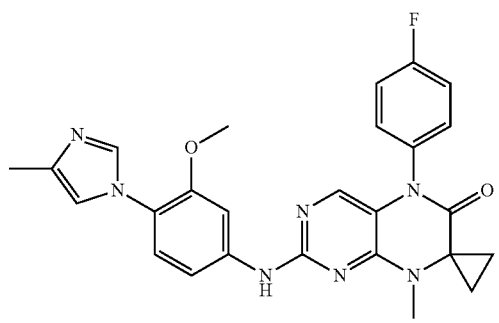 [SMILES: COc1cc(Nc2ncc3c(n2)N(C)C2(CC2)C(=O)N3c2ccc(F)cc2)ccc1-n1cnc(C)c1] |
| LVIII | 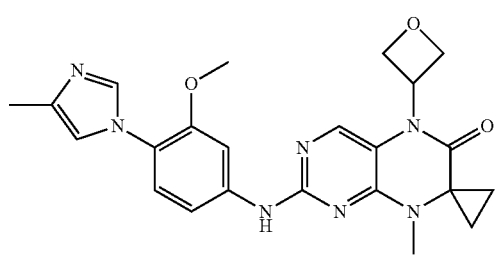 [SMILES: COc1cc(Nc2ncc3c(n2)N(C)C2(CC2)C(=O)N3C2COC2)ccc1-n1cnc(C)c1] |
| LIX | 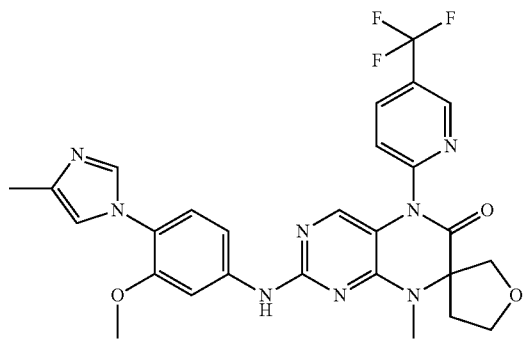 [SMILES: COc1cc(Nc2ncc3c(n2)N(C)C2(CCOC2)C(=O)N3c2ccc(C(F)(F)F)cn2)ccc1-n1cnc(C)c1] |

| No. | Structure |
|---|---|
| LX | 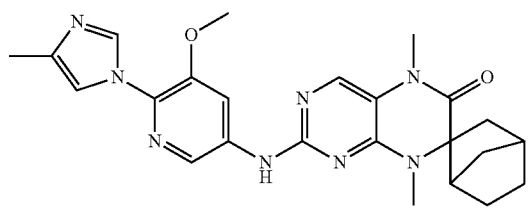 [SMILES: COc1cc(Nc2ncc3c(n2)N(C)C2(CC4CCC2C4)C(=O)N3C)cnc1-n1cnc(C)c1] |
| LXI | 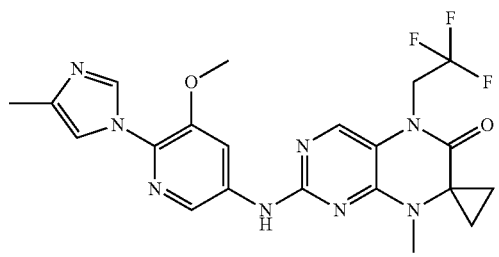 |
| LXII | 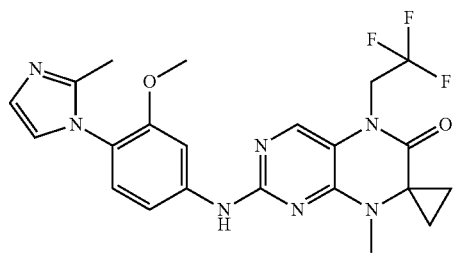 [SMILES: COc1cc(Nc2ncc3c(n2)N(C)C2(CC2)C(=O)N3CC(F)(F)F)ccc1-n1ccnc1C] |
| LXIII | 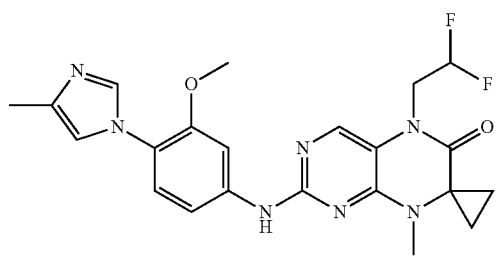 [SMILES: COc1cc(Nc2ncc3c(n2)N(C)C2(CC2)C(=O)N3CC(F)F)ccc1-n1cnc(C)c1] |
| LXIV | 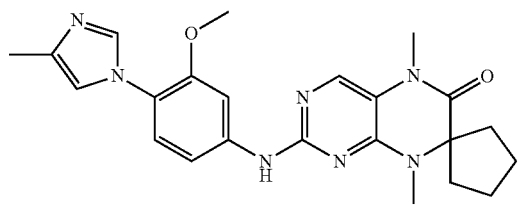 [SMILES: COc1cc(Nc2ncc3c(n2)N(C)C2(CCCC2)C(=O)N3C)ccc1-n1cnc(C)c1] |
| LXV | 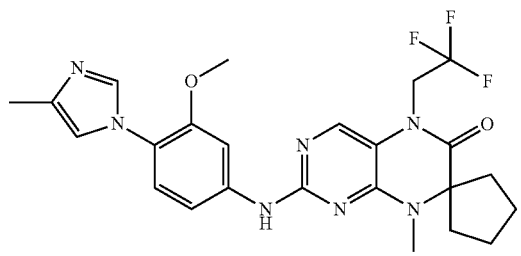 [SMILES: COc1cc(Nc2ncc3c(n2)N(C)C2(CCCC2)C(=O)N3CC(F)(F)F)ccc1-n1cnc(C)c1] |

| No. | Structure |
|---|---|
| LXVI | 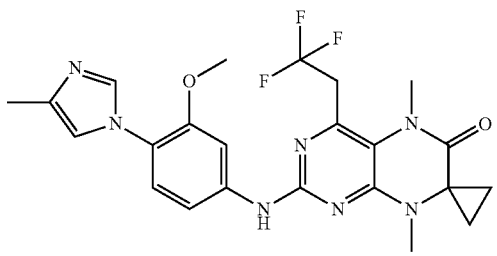 [SMILES: COc1cc(Nc2nc(CC(F)(F)F)c3c(n2)N(C)C2(CC2)C(=O)N3C)ccc1-n1cnc(C)c1] |

Some terms used above and hereinafter to describe the compounds according to the invention will now be defined more closely.

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl group, the latter of which is bound to the core or to the group to which the substituent is attached.

Within the present invention, the term "core molecule" is defined by the following structure:

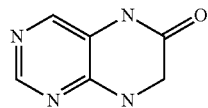

In general, the attachment site of a given residue to another group shall be variable, i.e. any capable atom, bearing hydrogens to be replaced, within this residue may be the linking spot to the group being attached, unless otherwise indicated.

In case a compound of the present invention is depicted in form of a chemical name and as a formula in case of any discrepancy the formula shall prevail.

An asterisk may be used in sub-formulas to indicate the bond which is connected to the core molecule as defined.

The dotted lines in sub-formulas of substituent D indicate the spiro atom being part of the core molecule of formula (I) and the substituent D. For example, the substructure

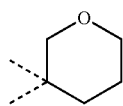

of substituent D means that ring D is attached to the core molecule of formula (I) via the indicated carbon atom resulting in the following structure:

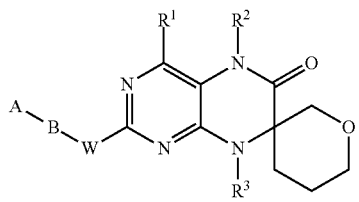

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term "substituted" as used herein means that any one or more hydrogens on the designated atom is replaced with a selection from the indicated group, provided that the designated atom's viable valence number is not exceeded, and that the substitution results in a stable compound.

The term "partially unsaturated" as used herein means that in the designated group or moiety 1, 2, or more, preferably 1 or 2, double bonds are present. Preferably, as used herein, the term "partially unsaturated" does not cover fully unsaturated groups or moieties.

The term "C-linked heterocyclyl" as used herein means that the heterocyclyl group is connected to the core molecule according to formula I by a bond from a C-atom of the heterocyclyl ring.

The term "halogen" generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. The term $C_{2-5}$-alkenyl includes for example the radicals $H_2C$=$CH$—, $H_2C$=$CH$—$CH_2$—, $H_3C$—$CH$=$CH$—, $H_2C$=$CH$—$CH_2$—$CH_2$—, $H_3C$—$CH$=$CH$—$CH_2$—, $H_3C$—$CH_2$—$CH$=$CH$—, $(H_3C)_2C$=$CH$—, $H_2C$=$CH$—$CH_2$—$CH_2$—$CH_2$—, $H_3C$—$CH$=$CH$—$CH_2$—$CH_2$—, $H_3C$—$CH_2$—$CH$=$CH$—$CH_2$—, $H_3C$—$CH_2$—$CH_2$—$CH$=$CH$—, $H_2C$=$CH$—$CH$=$CH$—$CH_2$— and $(H_3C)_2C$=$CH$—$CH_2$—.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. The term $C_{2-5}$-alkynyl includes for example the radicals HC≡C—, HC≡C—$CH_2$—, $H_3C$—C≡C—, HC≡C—$CH_2$—$CH_2$—, $H_3C$—C≡C—$CH_2$—, $H_3C$—$CH_2$—C≡C—, HC≡C—$CH_2$—$CH_2$—$CH_2$—, $H_3C$—C≡C—$CH_2$—$CH_2$—, $H_3C$—$CH_2$—C≡C—$CH_2$—, $H_3C$—$CH_2$—$CH_2$—C≡C— and $(H_3C)_2CH$—C≡C—.

The term "carbocyclyl" as used either alone or in combination with another radical, means, if not mentioned otherwise, a mono- bi- or tricyclic ring structure consisting of 3 to 14 carbon atoms. The term, if not mentioned otherwise, refers to fully saturated, partially saturated and aromatic ring systems. The term "carbocycle" encompasses fused, bridged and spirocyclic systems.

Thus, the term "carbocyclyl" includes the following exemplary structures which are not depicted as radicals as each form may be attached through a covalent bond to any atom so long as appropriate valences are maintained:

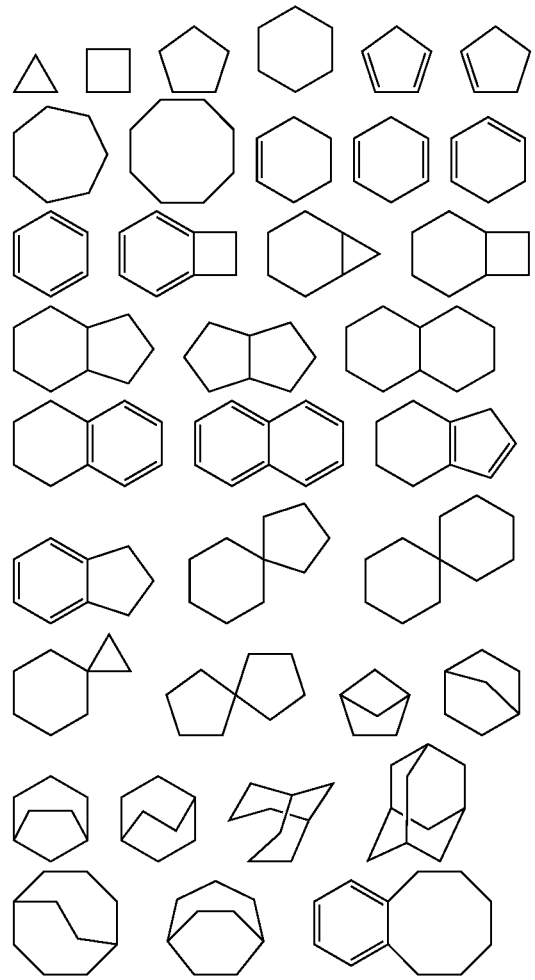

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heterocyclyl" means a saturated or unsaturated mono- or polycyclic-ring systems which may contain aromatic rings containing one or more heteroatoms selected from N, O or $S(O)_r$, wherein r=0, 1 or 2, consisting of, if not mentioned otherwise, 3 to 14 ring atoms wherein none of the heteroatoms is part of an aromatic ring. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

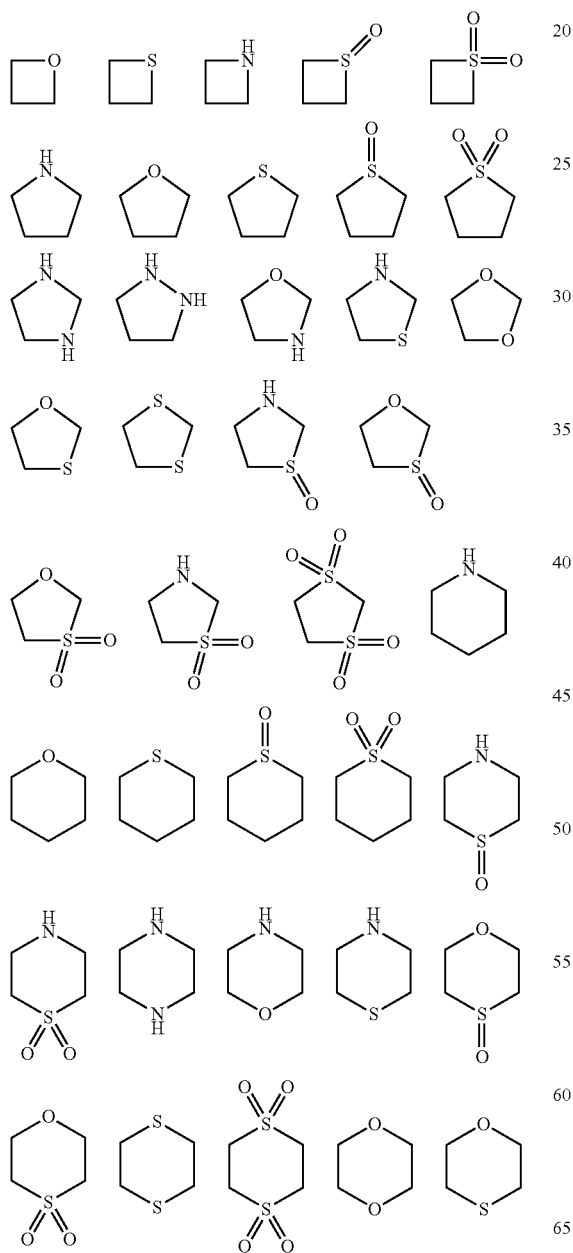

-continued

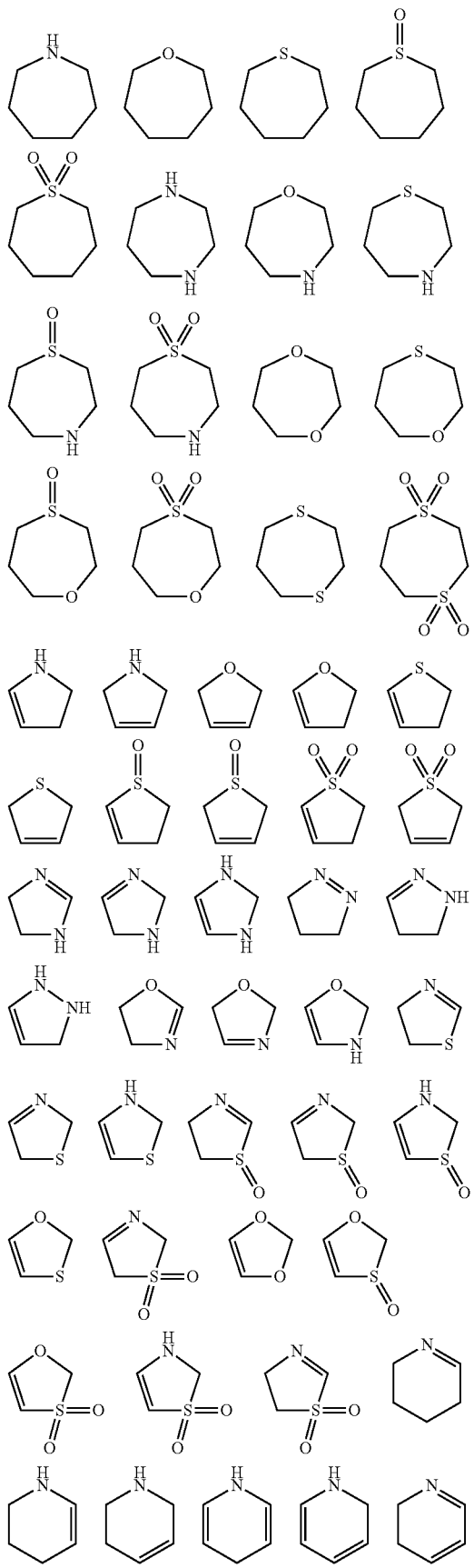

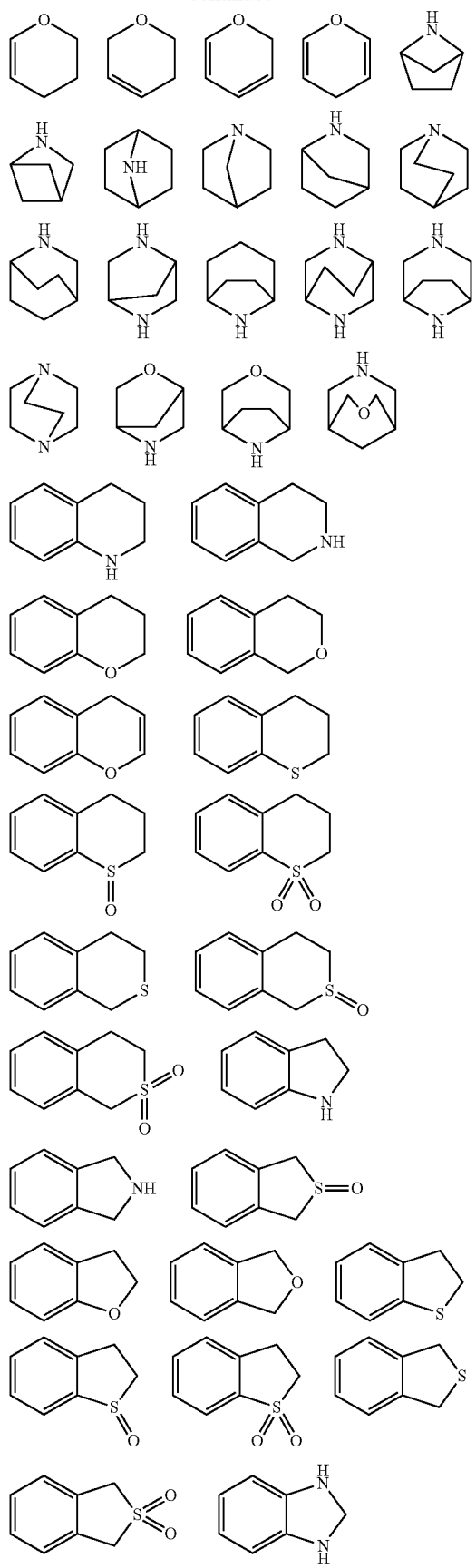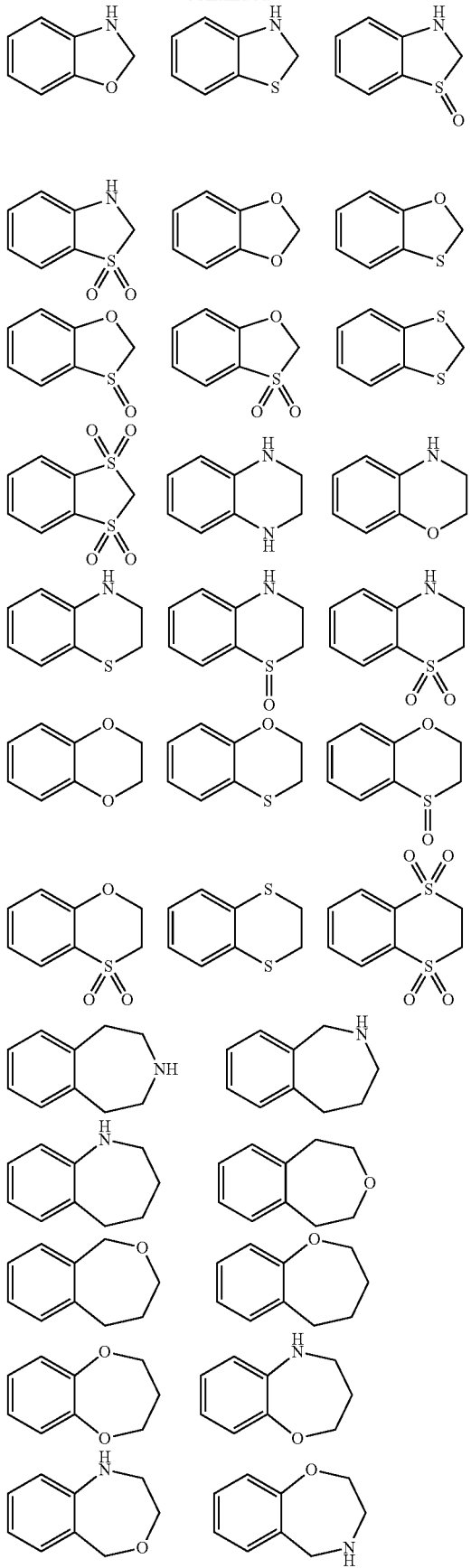

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

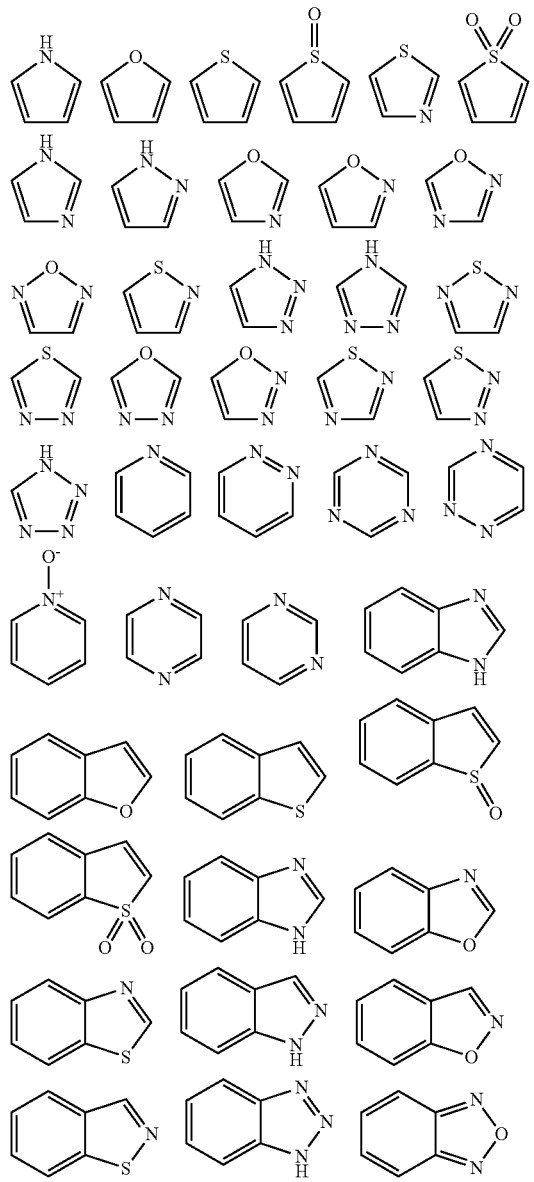

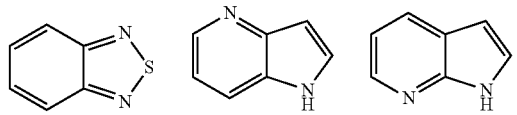
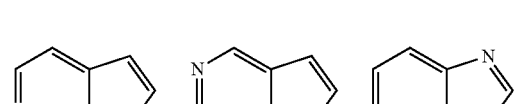
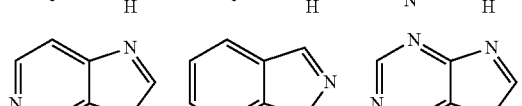
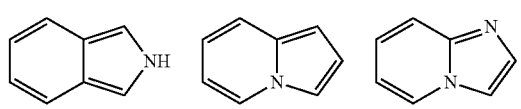
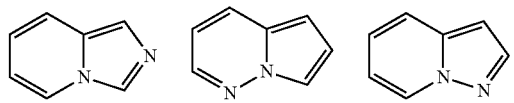
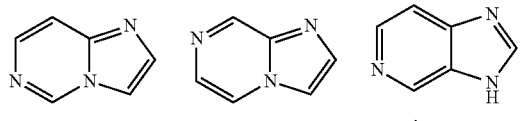
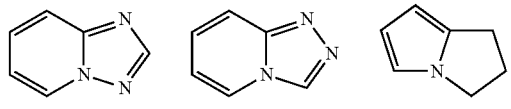
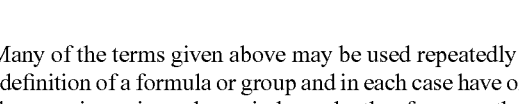
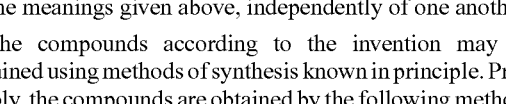
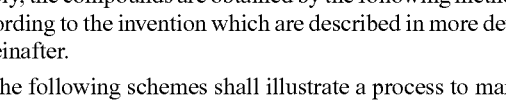
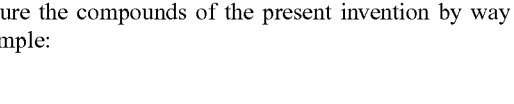
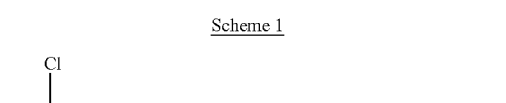

Many of the terms given above may be used repeatedly in the definition of a formula or group and in each case have one of the meanings given above, independently of one another.

The compounds according to the invention may be obtained using methods of synthesis known in principle. Preferably, the compounds are obtained by the following methods according to the invention which are described in more detail hereinafter.

The following schemes shall illustrate a process to manufacture the compounds of the present invention by way of example:

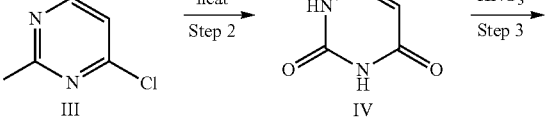

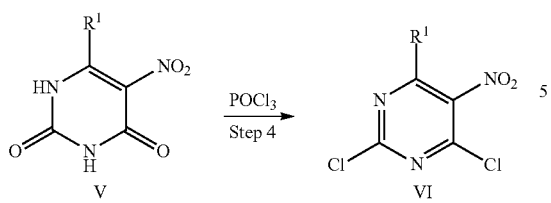
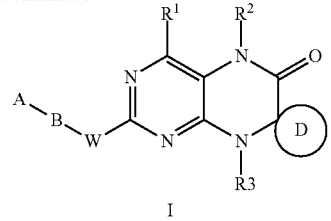

Scheme 1 illustrates the synthesis of 6-substituted 2,4-dichloro-5-nitro-pyrimidines (VI) als intermediates for the synthesis of dihydropteridinones (I):

In a first step 2,4,6-trichloro-pyrimidine (II) is reacted with Grignard reagents $R^1$—Mg—X (with X=Cl, Br, I, $R^1$) in an appropriate solvent like tetrahydrofurane in the presence of a Copper catalyst (e.g. Cu(I) iodide) to form 6-substituted 2,4-dichloro-pyrimidine derivatives (III). These compounds are converted in a second step to the corresponding 1H-pyrimidine-2,4-diones (IV) by heating with aqueous mineral acid (e.g. hydrochloric acid). In a third step, nitration, e.g. by using a mixture of sulfuric acid and nitric acid, leads to the corresponding 5-nitro-1H-pyrimidine-2,4-diones (V). In a fourth step, these compounds are heated with phosphorus oxychloride resulting in the formation of 6-substituted 2,4-dichloro-5-nitro-pyrimidines (VI).

Scheme 2: In a first step 6-substituted 2,4-dichloro-5-nitro-pyrimidines (VI, see Scheme 1) are reacted with alpha amino acid esters (VII, R preferentially methyl, ethyl) using an appropriate solvent/base system like diethyl ether/water/potassium hydrogen carbonate or acetone/water/potassium carbonate or dichloromethane/N-ethyl-diisopropylamine to form 2-chloro-5-nitro-pyrimidinyl esters (VIII). These intermediates are reduced in a second step, e.g. using iron in acetic acid to form dihydropteridinones IX after in situ cyclization. Subsequent alkylation using an alkylating agent $R^2$—X (with X=Cl, Br, I, Me-$SO_2$—O—, $CF_3$—$SO_2$—O—, 4-Me-Ph-$SO_2$—O—) and a base, e.g. sodium hydride or potassium carbonate in suitable solvents like N-methylpyrrolidone or dimethylformamide, leads to 2-chloro-7,8-dihydro-5H-pteridin-6-ones (X, step 3). These 2-chloro-7,8-dihydro-5H-pteridin-6-ones (X) are converted in a fourth step into the final products (I) by heating with an amine A-B—W—H in the presence of a suitable catalyst (e.g. p-toluenesulfonic acid in acetic acid) in a suitable solvent like 4-methyl-2-pentanol or N-methylpyrrolidone or dimethylsulfoxide to form the final dihydropteridinones (I). Alternatively, dihydropteridinones (I) can be obtained by heating 2-chloro-7,8-dihydro-5H-pteridin-6-ones (X) with an amine A-B—W—H in the presence of a suitable catalyst (e.g. $Pd(OAc)_2$ or $Pd_2(dba)_3$), a ligand (e.g. BINAP, dppf or Xantphos) and a base (e.g. cesium carbonate or potassium tert.-butoxide) in a suitable solvent like tetrahydrofurane or 1,4-dioxane.

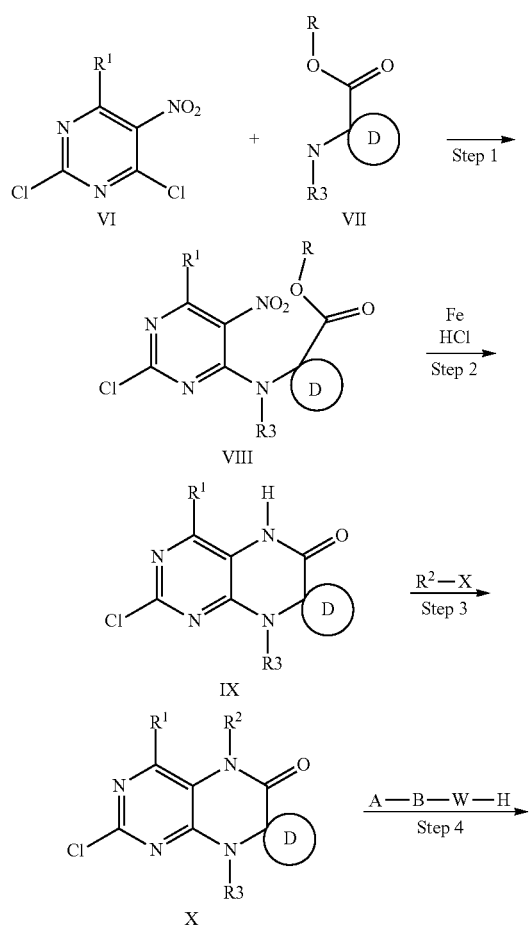

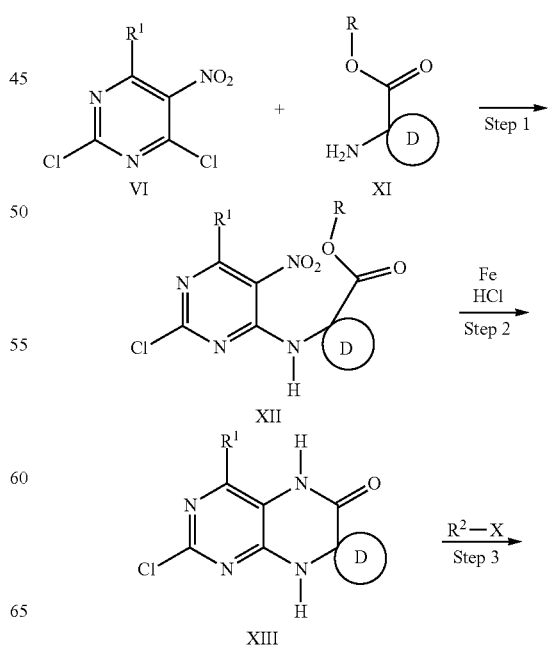

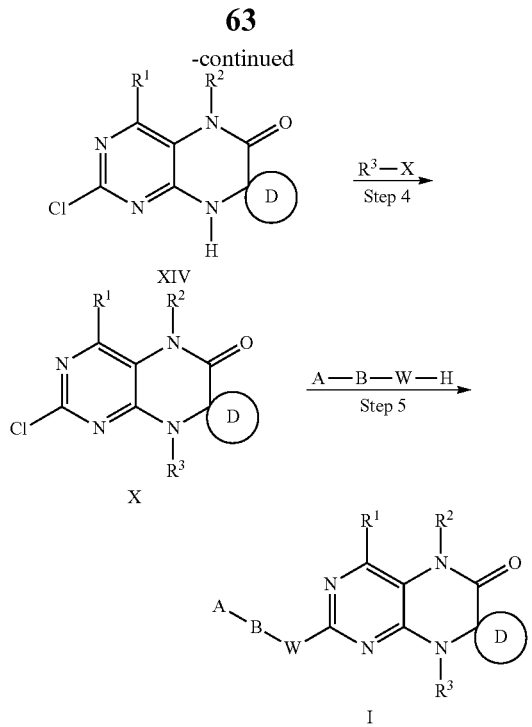

Scheme 3: In a first step 6-substituted 2,4-dichloro-5-nitro-pyrimidines (VI, see Scheme 1) are reacted with alpha amino acid esters (XI, R preferentially methyl, ethyl) using an appropriate solvent/base system like diethyl ether/water/potassium hydrogen carbonate or acetone/water/potassium carbonate or dichloromethane/N-ethyl-diisopropylamine to form 2-chloro-5-nitro-pyrimidinyl esters (XII). These intermediates are reduced in a second step, e.g. using iron in acetic acid to form dihydropteridinones XIII after in situ cyclization. Subsequent alkylation using an alkylating agent $R^2$—X (with X=Cl, Br, I, Me-SO$_2$—O—, CF$_3$—SO$_2$—O—, 4-Me-Ph-SO$_2$—O—) and a base, e.g. sodium hydride or potassium carbonate in suitable solvents like N-methylpyrrolidone or dimethylformamide, leads to 2-chloro-7,8-dihydro-5H-pteridin-6-ones (XIV, step 3). A second alkylation using an alkylating agent $R^2$—X (with X=Cl, Br, I, Me-SO$_2$—O—, CF$_3$—SO$_2$—O—, 4-Me-Ph-SO$_2$—O—) and a base, e.g. sodium hydride or potassium carbonate in suitable solvents like N-methylpyrrolidone or dimethylformamide, leads to 2-chloro-7,8-dihydro-5H-pteridin-6-ones (X, step 3). These 2-chloro-7,8-dihydro-5H-pteridin-6-ones (X) are converted in a fourth step into the final products (I) by heating with an amine A-B—W—H in the presence of a suitable catalyst (e.g. p-toluenesulfonic acid in acetic acid) in a suitable solvent like 4-methyl-2-pentanol or N-methylpyrrolidone or dimethylsulfoxide to form the final dihydropteridinones (I). Alternatively, dihydropteridinones (I) can be obtained by heating 2-chloro-7,8-dihydro-5H-pteridin-6-ones (X) with an amine A-B—W—H in the presence of a suitable catalyst (e.g. Pd(OAc)$_2$ or Pd$_2$(dba)$_3$), a ligand (e.g. BINAP, dppf or Xantphos) and a base (e.g. cesium carbonate or potassium tert.-butoxide) in a suitable solvent like tetrahydrofurane or 1,4-dioxane.

The compounds according to the invention are advantageously also obtainable using the methods described in the examples that follow, which may also be combined for this purpose with methods known to the skilled man from the literature.

As already mentioned, the compounds of general formula I according to the invention and the physiologically acceptable salts thereof have valuable pharmacological properties, particularly as modulators of γ-secretase.

Biological Examples

Screening for compounds which preferentially inhibit production of Aβ42 vs. total Aβ was performed using H4 neuroglioma cells stably expressing the human APP695 isoform grown in Dulbecco's Modified Eagles medium (DMEM) GlutaMAX supplemented with 10% Fetal Bovine Serum and 250 μg/mL Zeocine. Cells were plated out to near confluency. The compounds to be tested were received as 10 mM stocks in 100% DMSO. A dilution series was initially generated in 100% DMSO and then diluted 200-fold in cell culture media such that the tested concentration range was 30 μM to 0.1 nM and the final DMSO concentration was 0.5%. The diluted compounds were incubated with the cells for 22 hours in an incubator at 37° C. and 5% CO$_2$. Aβ42 as well as Aβ total levels were then measured post-incubation from the supernatant of the cells. Aβ42 levels were determined using a specific electrochemiluminescence assay provided by Meso Scale Discovery (Catalog #L21CA-1) according to the manufacturer's protocol. Aβ total levels were likewise determined using a specific electrochemiluminescence assay provided by Meso Scale Discovery (Catalog #L21ZA-1) according to the manufacturer's protocol. To identify compounds which preferentially inhibited Aβ42, the ratio Aβ total IC$_{50}$/Aβ42 IC$_{50}$ was determined, where the higher the ratio, the more specific the inhibition of Aβ42 over Aβ total.

The compounds of general formula I according to the invention for example have IC$_{50}$ values below 30000 nM, particularly below 1000 nM, most preferably below 500 nM.

TABLE 3

Activity of the examples (Ex) compiled in the experimental part, based on Aβ$_{42}$ cellular IC$_{50}$ values in H4 neuroglioma cells (see above).

| Ex | IC$_{50}$ [μM] | Ratio Aβ(total)/Aβ$_{42}$ | Ex | IC$_{50}$ [μM] | Ratio Aβ(total)/Aβ$_{42}$ |
|---|---|---|---|---|---|
| 1 | 0.12 | >244 | 2 | 0.19 | 89 |
| 3 | 5.4 | >6 | 4 | 0.29 | 101 |
| 5 | 3.2 | >9 | 6 | 0.22 | >136 |
| 7 | 0.095 | >315 | 8 | 3.0 | >10 |
| 9 | 0.30 | >101 | 10 | 0.62 | 46 |
| 11 | 0.31 | 26 | 12 | 1.9 | 11 |
| 13 | 2.2 | >13 | 14 | 1.4 | >27 |
| 15 | 2.1 | >15 | 16 | 0.18 | 88 |
| 17 | 0.094 | 65 | 18 | 0.30 | 145 |
| 19 | 0.28 | >257 | 20 | 0.79 | >90 |
| 21 | 0.22 | 114 | 22 | 3.3 | >9 |
| 23 | 0.039 | 599 | 24 | 3.0 | >10 |
| 25 | 0.29 | 91 | 26 | 0.35 | 46 |
| 27 | 0.27 | >112 | 28 | 10.5 | >3 |
| 29 | 0.27 | 39 | 30 | 0.10 | 96 |
| 31 | 0.18 | 47 | 32 | 0.079 | 124 |
| 33 | 0.14 | 124 | 34 | 0.073 | 115 |
| 35 | 0.076 | 180 | 36 | 0.069 | 179 |
| 37 | 0.94 | 29 | 37a | 0.060 | 307 |
| 37b | 0.172 | 47 | 37c | 0.116 | 75 |
| 38 | 0.41 | >15 | 44 | 0.085 | 50 |
| 37d | 0.815 | >36 | 40 | 0.485 | >62 |
| 37f | 0.145 | 55 | 45 | 0.058 | >517 |
| 37g | 0.196 | 58 | 46 | 0.098 | >306 |
| 37e | 0.086 | 82 | 47 | 0.191 | 98 |
| 37k | 0.12 | 88 | 48 | 0.389 | 22 |
| 37h | 0.123 | 85 | 49 | 0.095 | 69 |
| 37i | 0.15 | 54 | 50 | 0.204 | >147 |

TABLE 3-continued

Activity of the examples (Ex) compiled in the
experimental part, based on Aβ$_{42}$ cellular IC$_{50}$
values in H4 neuroglioma cells (see above).

| Ex | IC$_{50}$ [µM] | Ratio Aβ(total)/ Aβ$_{42}$ | Ex | IC$_{50}$ [µM] | Ratio Aβ(total)/ Aβ$_{42}$ |
|---|---|---|---|---|---|
| 37j | 0.073 | 57 | 51 | 0.059 | 126 |
| 39 | 0.078 | 91 | 52 | 0.11 | 61 |
| 41 | 1.22 | >25 | 53 | 0.04 | 132 |
| 42 | 0.206 | 51 | 54 | 0.022 | 116 |
| 43 | 0.123 | 237 | 55 | 0.076 | 103 |

Whereas γ-Secretase inhibitors simultaneously inhibit production of all Aβ species, γ-Secretase modulators preferentially inhibit the production of the neurotoxic Aβ42 species. In order to absolutely define the described compounds as modulators of γ-Secretase as opposed to simply inhibitors of γ-Secretase, measurements of not only Aβ42 but also Aβ total are performed. When the ratio of Aβ total IC$_{50}$/Aβ42 IC$_{50}$ is >1, the compound preferentially inhibits Aβ42 production, thereby demonstrating that the compound is in fact a γ-Secretase modulator.

In view of their ability to modulate the activity of γ-secretase, the compounds of general formula I according to the invention are suitable for the treatment and/or preventative treatment of all those conditions or diseases which may be affected by the formation of Aβ peptides. Therefore, compounds according to the invention are particularly suitable for the prevention or treatment of diseases, particularly Down's syndrome, Abeta-amyloid angiopathy, cerebral amyloid angiopathy, hereditary cerebral hemorrhage, a disorder associated with cognitive impairment, MCI ("mild cognitive impairment"), Alzheimer's Disease, memory loss, attention deficit symptoms associated with Alzheimer's disease, neurodegeneration associated with Alzheimer's disease, diffuse Lewy body type of Alzheimer's Disease, dementia of mixed vascular origin, dementia of degenerative origin, pre-senile dementia, senile dementia, dementia associated with Parkinson's disease, progressive supranuclear palsy or cortical basal degeneration, the dry form of age-related macular degeneration and glaucoma.

Preferably the compounds according to the invention, including the physiologically acceptable salts thereof, are suitable for the prevention or treatment of Alzheimer's Disease, the dry form of age-related macular degeneration and/or MCI.

In particular, the compounds according to the invention, including the physiologically acceptable salts thereof, are suitable for the prevention or treatment of Alzheimer's Disease and/or MCI.

In a further aspect of the present invention the present invention relates to methods for the treatment or prevention of above mentioned diseases and conditions, which method comprises the administration of an effective amount of a compound of general formula I to a human being.

The dose range of the compounds of general formula I applicable per day is usually from 0.1 to 1000 mg, preferably from 1 to 500 mg by oral route, in each case administered 1 to 4 times a day.

Each dosage unit may conveniently contain from 0.1 to 500 mg, preferably 1 to 100 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Suitable preparations for administering the compounds of formula I will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) should be in the range from 0.1 to 95 wt.-%, preferably 5.0 to 90 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, citric acid, tartaric acid, water, polyvinylpyrrolidone, water/ethanol, water/glycerol, water/sorbitol, water/polyethylene glycol, propylene glycol, cetylstearyl alcohol, carboxymethylcellulose or fatty substances such as hard fat or suitable mixtures thereof.

The compounds according to the invention may also be used in conjunction with other active substances, particularly for the treatment and/or prevention of the diseases and conditions mentioned above. Other active substances which are suitable for such combinations include, for example, BACE inhibitors; amyloid aggregation inhibitors (e.g. ELND-005); directly or indirectly acting neuroprotective and/or disease-modifying substances; anti-oxidants (e.g. vitamin E or ginkolide); anti-inflammatory substances (e.g. Cox inhibitors, NSAIDs additionally or exclusively having Abeta lowering properties); HMG-CoA reductase inhibitors (statins); acetylcholinesterase inhibitors (e.g., donepezil, rivastigmine, tacrine, galantamine); NMDA receptor antagonists (e.g. memantine); AMPA receptor agonists; AMPA receptor positive modulators, AMPAkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocyclin or rifampicin); PDE2, PDE4, PDE5, PDE9, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, glycine transporter 1 inhibitors, antidepressants, such as citalopram, fluoxetine, paroxetine, sertraline and trazodone; anxiolytics, such as lorazepam and oxazepam; antiphychotics, such as aripiprazole, clozapine, haloperidol, olanzapine, quetiapine, risperidone and ziprasidone, and other substances that modulate receptors or enzymes in a manner such that the efficacy and/or safety of the compounds according to the invention is increased and/or unwanted side effects are reduced. The compounds according to the invention may also be used in combination with immunotherapies (e.g., active immunisation with Abeta or parts thereof or passive immunisation with humanised anti-Abeta antibodies or nanobodies) for the treatment of the above-mentioned diseases and conditions.

The dosage for the combination partners mentioned above is usefully ⅕ of the lowest dose normally recommended up to 1/1 of the normally recommended dose.

Therefore, in another aspect, this invention relates to the use of a compound according to the invention or a physiologically acceptable salt thereof combined with at least one of the active substances described above as a combination partner, for preparing a pharmaceutical composition which is suitable for the treatment or prevention of diseases or conditions which can be affected by modulation of γ-secretase. These are preferably Aβ-related pathologies, particularly one of the diseases or conditions listed above, most particularly Alzheimer's Disease and/or MCI.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

Experimental Section

The following examples are intended to illustrate the invention, without restricting its scope.

As a rule, melting points, IR, $^1$H-NMR and/or mass spectra have been obtained for the compounds prepared. Unless otherwise stated, Rf values were obtained using ready-made silica gel 60 F254 TLC plates (E. Merck, Darmstadt, item no. 1.05714) without chamber saturation. The ratios given for the eluants refer to units by volume of the solvents in question. Chromatographic purification was done using silica gel supplied by E. Merck, Darmstadt (Silica gel 60, 0.040-0.063 mm, item no. 1.09385.2500).

The following abbreviations are used in the following examples:
ACN Acetonitrile
Boc t-butyloxycarbonyl-
CH Cyclohexane
DAD Diode array detection
DCM Dichloromethane
DIPEA N-Ethyl-diisopropylamine
DMSO Dimethylsulphoxide
DMF N,N-Dimethylformamide
EA Ethyl acetate
ESI Electrospray ionisation
h Hour(s)
HPLC High performance liquid chromatography
M Molar
MeOH Methanol
min Minute(s)
mL Milliliters
μL Microliters
mmol Millimoles
μmol Micromoles
MPLC Medium pressure liquid chromatography
MS Mass spectrometry
NMP N-Methyl-pyrrolidinone
Pd/C Palladium on charcoal
PE Petroleum ether
psi pound-force per square inch
Rf Retention factor
Rt Retention time
sat. saturated
tert. Tertiary
TLC Thin layer chromatography
TFA Trifluoroacetic acid
THF Tetrahydrofurane
UPLC Ultra performance liquid chromatography All references to brine refer to a saturated aqueous solution of sodium chloride. Unless otherwise indicated, all temperatures are expressed in ° C. (degrees Centigrade). All reactions are conducted not under an inert atmosphere at room temperature unless otherwise noted.

EXAMPLES

HPLC/UPLC Methods

Method A

| Device: |
| Waters Alliance with DAD and ESI-MS detector |
| Column: |
| Waters XBridge C18, 4.6 × 30 mm, 3.5 μm |

| Time [min] | % Solvent A [H₂O, 0.10% TFA] | % Solvent B [MeOH] | Flow rate [mL/min] | Temperature [° C.] |
| --- | --- | --- | --- | --- |
| 0.0 | 95 | 5 | 4 | 60 |
| 1.6 | 0 | 100 | 4 | 60 |
| 1.85 | 0 | 100 | 4 | 60 |
| 1.9 | 95 | 5 | 4 | 60 |

Method B

| Device: |
| Waters Alliance with DAD and ESI-MS detector |
| Column: |
| Waters XBridge C18, 4.6 × 30 mm, 3.5 μm |

| Time [min] | % Solvent A [H₂O, 0.10% NH₃] | % Solvent B [MeOH] | Flow rate [mL/min] | Temperature [° C.] |
| --- | --- | --- | --- | --- |
| 0.0 | 95 | 5 | 4 | 60 |
| 0.2 | 95 | 5 | 4 | 60 |
| 1.5 | 0 | 100 | 4 | 60 |
| 1.75 | 0 | 100 | 4 | 60 |

Method C

Device:
Waters Acquity with DAD and ESI-MS detector
Column:
Waters XBridge BEH C18, 2.1 × 30 mm, 1.7 μm

| Time [min] | % Solvent A [H$_2$O, 0.13% TFA] | % Solvent B [MeOH, 0.05% TFA] | Flow rate [mL/min] | Temperature [° C.] |
|---|---|---|---|---|
| 0.0 | 99 | 1 | 1.3 | 60 |
| 0.05 | 99 | 1 | 1.3 | 60 |
| 1.05 | 0 | 100 | 1.3 | 60 |
| 1.2 | 0 | 100 | 1.3 | 60 |

Method D

Device:
Waters Alliance with DAD and ESI-MS detector
Column:
Waters XBridge C18, 4.6 × 30 mm, 3.5 μm

| Time [min] | % Solvent A [H$_2$O, 0.1% TFA] | % Solvent B [MeOH] | Flow rate [mL/min] | Temperature [° C.] |
|---|---|---|---|---|
| 0.0 | 95 | 5 | 4 | 60 |
| 1.6 | 0 | 100 | 4 | 60 |
| 1.85 | 0 | 100 | 4 | 60 |
| 1.9 | 95 | 5 | 4 | 60 |

Method E

Device:
Waters Acquity with DAD and ESI-MS detector
Column:
Sunfire C18, 2.1 × 20 mm, 2.5 μm

| Time [min] | % Solvent A [H$_2$O, 0.1% TFA] | % Solvent B [MeOH] | Flow rate [mL/min] | Temperature [° C.] |
|---|---|---|---|---|
| 0.00 | 99 | 1 | 1.3 | 60 |
| 0.15 | 99 | 1 | 1.3 | 60 |
| 1.10 | 0 | 100 | 1.3 | 60 |
| 1.25 | 0 | 100 | 1.3 | 60 |

Method F

Device:
Agilent 1200 with DAD and ESI-MS detector
Column:
XBridge C18, 3 × 30 mm, 2.5 μm

| Time [min] | % Solvent A [H2O, 0.1% NH4OH] | % Solvent B [MeOH] | Flow rate [mL/min] | Temperature [° C.] |
|---|---|---|---|---|
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

Method G

Device:
Waters Acquity with DAD and ESI-MS detector
Column:
XBridge C18, 2.1 × 20 mm, 2.5 μm

| Time [min] | % Solvent A [H2O, 0.10% TFA] | % Solvent B [MeOH] | Flow rate [mL/min] | Temperature [° C.] |
|---|---|---|---|---|
| 0.0 | 95 | 5 | 1.4 | 60 |
| 0.05 | 95 | 5 | 1.4 | 60 |
| 1.00 | 0 | 100 | 1.4 | 60 |
| 1.1 | 0 | 100 | 1.4 | 60 |

Method H

Device:
Waters Alliance with DA- and MS-Detector
Column:
XBridge C18_4.6 × 30 mm, 3.5 μm

| Time [min] | % Solvent A [H2O, 0.1% NH3] | % Solvent B [Acetonitrile] | Flow rate [mL/min] | Temperature [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

Method I

Device:
Waters Acquity with DA- and MS-Detector
Column:
XBridge BEH C18_2.1 × 30 mm, 1.7 μm

| Time [min] | % Solvent A [H2O, 0.1% TFA] | % Solvent B [Acetonitrile] | Flow rate [mL/min] | Temperature [° C.] |
|---|---|---|---|---|
| 0.0 | 99 | 1 | 1.6 | 60 |
| 0.02 | 99 | 1 | 1.6 | 60 |
| 1.0 | 0 | 100 | 1.6 | 60 |
| 1.1 | 0 | 100 | 1.6 | 60 |

Method J

Device:
Waters Acquity with DA- and MS-Detector
Column:
Sunfire C18, 2.1 × 30 mm, 2.5 μm

| Time [min] | % Solvent A [H2O, 0.1% TFA] | % Solvent B [Acetonitrile] | Flow rate [mL/min] | Temperature [° C.] |
|---|---|---|---|---|
| 0.0 | 99 | 1 | 1.5 | 60 |
| 0.02 | 99 | 1 | 1.5 | 60 |
| 1.0 | 0 | 100 | 1.5 | 60 |
| 1.1 | 0 | 100 | 1.5 | 60 |

Method K

Device:
Agilent 1200 with DAD and ESI-MS detector
Column:
XBridge C18, 3 × 30 mm, 2.5 μm

| Time [min] | % Solvent A [H2O, 0.1% TFA] | % Solvent B [Acetonitrile] | Flow rate [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

Method L

Device:
Waters Alliance with DA- and MS-Detector
Column:
Sunfire C18, 4.6 × 30 mm, 3.5 μm

| Time [min] | % Solvent A [H2O, 0.1% TFA] | % Solvent B [Acetonitrile] | Flow rate [mL/min] | Temperature [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

Method M

Device:
Waters Alliance with DA- and MS-Detector
Column:
Sunfire C18, 4.6 × 30 mm, 3.5 μm

| Time [min] | % Solvent A [H2O, 0.1% TFA] | % Solvent B [Methanol] | Flow rate [mL/min] | Temperature [° C.] |
|---|---|---|---|---|
| 0.00 | 95 | 5 | 4 | 60 |
| 1.60 | 0 | 100 | 4 | 60 |
| 1.85 | 0 | 100 | 4 | 60 |
| 1.90 | 95 | 5 | 4 | 60 |

Method N

Device:
Waters Alliance with DA- and MS-Detector
Column:
XBridge C18, 4.6 × 30 mm, 3.5 μm

| Time [min] | % Solvent A [H2O, 0.1% TFA] | % Solvent B [Acetonitrile] | Flow rate [mL/min] | Temperature [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

Method O

Device:
Agilent 1200 with DAD and ESI-MS detector
Column:
XBridge C18, 3 × 30 mm, 2.5 μm

| Time [min] | % Solvent A [H2O, 0.1% NH3] | % Solvent B [Acetonitrile] | Flow rate [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

Method P

Device:
Waters Acquity with DA- and MS-Detector
Column:
BEH C18, 2.1 × 30 mm, 1.7 μm

| Time [min] | % Solvent A [H2O, 0.1% NH3] | % Solvent B [Acetonitrile] | Flow rate [mL/min] | Temperature [° C.] |
|---|---|---|---|---|
| 0.0 | 95.0 | 5.0 | 1.5 | 60 |
| 0.8 | 0.1 | 99.9 | 1.5 | 60 |
| 0.9 | 0.1 | 99.9 | 1.5 | 60 |

Intermediate A1

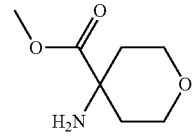

4-Amino-tetrahydro-pyran-4-carboxylic acid (2.00 g, 11.0 mmol) is added at 0° C. in portions to a mixture of MeOH (15 mL) and thionylchloride (1.60 mL, 0.022 mmol). The reaction mixture is heated to reflux for 12 h. After evaporation of the solvents diethyl ether is added and the precipitate is filtered off yielding the product as the hydrochloride salt.

MS (ESI$^+$): m/z=160 [M+H]$^+$

Intermediate A2-1

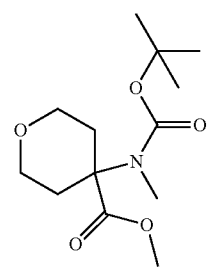 [SMILES: COC(=O)C1(N(C)C(=O)OC(C)(C)C)CCOCC1]

4-(Boc-amino)tetrahydropyran-4-carboxylic acid (1.96 g, 8.00 mmol) is mixed with N,N-dimethylformamide (15 mL) and sodium hydride (60% in oil, 0.800 g, 20.0 mmol).

Then methyl iodide (1.49 mL, 24.0 mmol) is added and the reaction mixture is stirred for 12 h at room temperature. The precipitate is filtered off. The filtrate is concentrated in vacuo. The residue is extracted with water and EA. The organic phase is dried over magnesium sulfate and concentrated in vacuo to give the product as an oil.

MS (ESI⁺): m/z=274 [M+H]⁺
HPLC (Method A): Rt=1.13 min
Intermediate A2

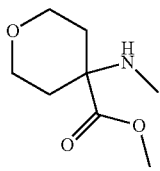

Intermediate A2-1 (2.88 g, 10.6 mmol) is dissolved in dioxane (10 mL) and 4M HCl solution in dioxane (10.6 mL) is added. The mixture is stirred for 12 h at room temperature. After concentration in vacuo diethylether is added and the resulting precipitate is filtered off. The product is obtained as hydrochloride salt.

MS (ESI⁺): m/z=174 [M+H]⁺
HPLC (Method A): Rt=0.25 min
Intermediate A3

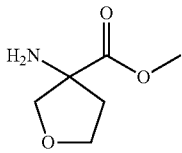

Intermediate A3 is prepared with racemic 3-amino-tetrahydrofuran-3-carboxylic acid in analogy to the preparation of intermediate A1. As no precipitate is observed after adding diethyl ether, the reaction mixture is concentrated in vacuo yielding the product as hydrochloride salt.

MS (ESI⁺): m/z=146 [M+H]⁺
HPLC (Method A): Rt=0.15 min
Intermediate A4-1

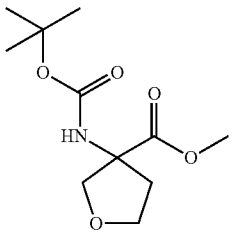 [SMILES: COC(=O)C1(NC(=O)OC(C)(C)C)CCOC1]

Intermediate A3 (4.10 g, 22.6 mmol) is mixed with tetrahydrofuran (100 mL), triethyl amine (3.49 mL, 24.8 mmol) and di-tert-butyl-dicarbonate (5.67 g, 26.0 mmol) and stirred for 12 h at 60° C. The precipitate is filtered off and the filtrate is concentrated in vacuo to give the product as an oil.

MS (ESI⁺): m/z=246 [M+H]⁺
HPLC (Method A): Rt=0.97 min
Intermediate A4-2

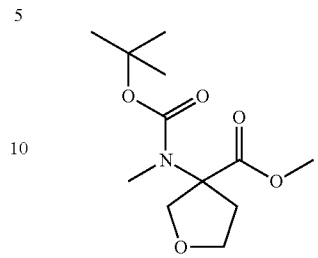

Intermediate A4-2 is prepared with intermediate A4-1 in analogy to the preparation of intermediate A2-1.
MS (ESI⁺): m/z=260 [M+H]⁺
HPLC (Method A): Rt=1.10 min
Intermediate A4

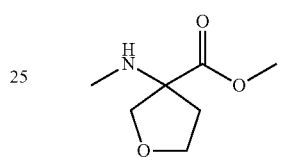

Intermediate A4 (as hydrochloride salt) is prepared with intermediate A4-2 in analogy to the preparation of intermediate A2 using trifluoroacetic acid instead of HCl. The product is obtained as trifluoroacetate.
MS (ESI⁺): m/z=160 [M+H]⁺
Intermediate A5-1

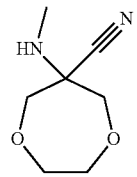

KCN (2.71 g, 41.0 mmol) is added to a solution of [1,4] dioxepan-6-one (5.00 g, 41 mmol) and methylamine hydrochloride (2.819 g, 41 mmol) in methanol (25 mL) and water (25 mL) at 0° C. The reaction mixture is stirred at 0° C. for 3 h, warmed to rt and stirred over night. The mixture is concentrated in vacuo. Standard work up yielded crude A5-1 which is used in the following step without further purification.
Intermediate A5-1b

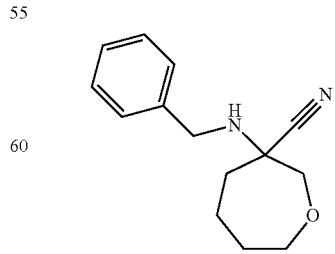

KCN (0.69 g, 10.5 mmol) is added to a solution of 3-oxepanone (1.00 g, 8.76 mmol; WO 2010021680) and benzylamine hydrochloride (1.26 g, 8.76 mmol) in methanol (10 mL) and water (10 mL) and the reaction mixture is stirred at room temperature for 16 h. The mixture is diluted with sat. sodium bicarbonate solution and EA. The organic layer is separated, dried over sodium sulfate, filtered and concentrated in vacuo to get the product without further purification.

TLC (silica gel, PE/EA 7/3): Rf=0.60
Intermediate A5-2

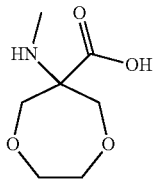

A5-1 (800 mg, 5.12 mmol) in concentrated aqueous HCl solution (15.0 mL) is heated to reflux over night. The reaction mixture is concentrated in vacuo and used in the next step without further purification.
Intermediate A5-2b

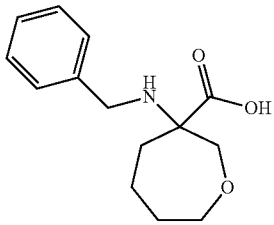 [SMILES: O=C(O)C1(NCc2ccccc2)CCCCOC1]

A5-1b (500 mg, 2.17 mmol) in conc. aqueous HCl solution and acetic acid is heated to reflux for 24 h. The reaction mixture is concentrated in vacuo and used in the next step without further purification.

TLC (silica gel, PE/EA 1/1): Rf=0.20
Intermediate A5

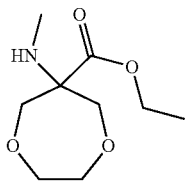

A5-2 (5.00 g, 29.0 mmol) in ethanolic HCl (35%, 125 mL) is refluxed over night. The reaction mixture is concentrated and purified by column chromatography (silica: eluent: DCM:MeOH 100:1).

TLC (DCM/MeOH 30:1): Rf=0.3
Intermediate A5b

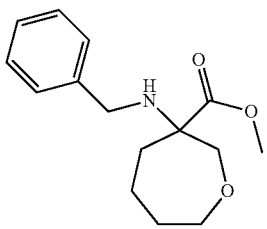 [SMILES: COC(=O)C1(NCc2ccccc2)CCCCOC1]

A5-2b (4.00 g, 16.0 mmol) in methanolic HCl (6 mol/L) is refluxed over night. The reaction mixture is concentrated and the residue is dissolved in water and neutralized with sat. sodium bicarbonate solution and then extracted with EA. The combined organic layers are dried over sodium sulfate, filtered and concentrated in vacuo to give the product.

TLC (silica gel, PE/EA 8/2): Rf=0.60
Intermediate A6-1

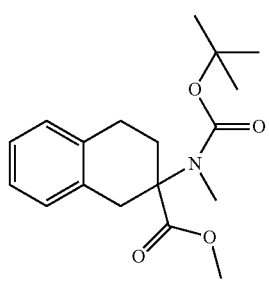 [SMILES: COC(=O)C1(N(C)C(=O)OC(C)(C)C)CCc2ccccc2C1]

Intermediate A6-1 is prepared with 2-(tert-butoxycarbonylamino)-1,2,3,4-tetrahydronaphthalene-2-carboxylic acid in analogy to the preparation of intermediate A4-2.

HPLC (Method A): Rt=1.5 min
Intermediate A6

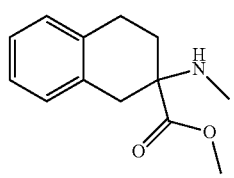 [SMILES: CNC1(C(=O)OC)CCc2ccccc2C1]

Intermediate A6-2a is prepared with intermediate 18a in analogy to the preparation of intermediate A4.

HPLC (Method A): Rt=0.75 min
Intermediate A7

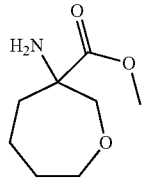

Intermediate A5b (2.40 g, 8.66 mmol) in methanol is hydrogenated (H$_2$ atmosphere, 50 psi) with Pd/C (10%) at 30° C. The reaction mixture is filtered and concentrated in vacuo to give the product without further purification.
Intermediate A8-1

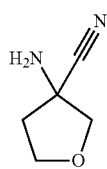

Intermediate A8-1 is prepared from dihydrofuran-3(2H)-one in analogy to the preparation of intermediate A5-1b.
Intermediate A8

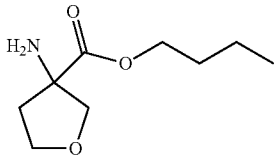

Intermediate A8 is prepared from intermediate A8-1 and n-butanole in analogy to the preparation of intermediate A5-2b.
Intermediate A9-1

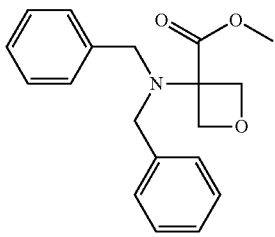 [SMILES: COC(=O)C1(N(Cc2ccccc2)Cc2ccccc2)COC1]

To a solution of 3-dibenzyl-amino-oxetane-3-carboxylic acid (1.50 g, 5.045 mmol; WO 2010097372) in 30 mL ACN and 3 mL methanol, trimethylsilyldiazomethane in hexane (2 M, 3.03 mL, 6.054 mmol) is added dropwise under cooling. The reaction mixture is stirred at room temperature for 1.5 h. To the reaction mixture conc. acetic acid (360 µL) is added and evaporated. The residue is treated with sodium hydroxide solution (1 mol/L) and extracted with DCM. The organic layer is concentrated in vacuo to give the product.

MS (ESI$^+$): m/z=312 [M+H]$^+$
HPLC (Method A): Rt=1.54 min.
Intermediate A9

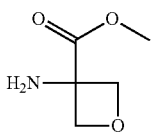

Intermediate A9-1 (1.55 g, 4.978 mmol) in 75 mL methanol is hydrogenated (H$_2$ atmosphere, 50 psi) with Pd/C (10%) at room temperature for 9 h. The reaction mixture is filtered and concentrated in vacuo to give the product without further purification.

MS (ESI$^+$): m/z=132 [M+H]$^+$
HPLC (Method A): Rt=0.13 min.
Intermediate A10

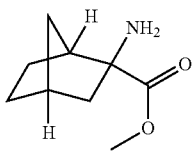

Intermediate A10-1 is prepared from 2-amino-2-norbornanecarboxylic acid in analogy to the preparation of intermediate A1.

MS (ESI$^+$): m/z=170 [M+H]$^+$
Intermediate A11-1

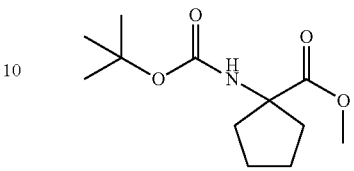

Intermediate A11-1 is prepared from Boc-1-aminocyclopentane-1-carboxylic acid in analogy to the preparation of intermediate A9-1.

MS (ESI$^+$): m/z=244 [M+H]$^+$
Intermediate A11-2

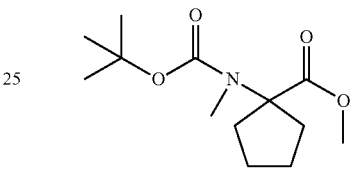

To intermediate A11-1 (1.429 g, 5.573 mmol) in DMF (20 mL) sodium hydride (60% in oil, 0.470 g, 11.747 mmol) and methyl iodide (0.548 mL, 8.810 mmol) are added and the reaction mixture is stirred at room temperature for 12 h. To the reaction mixture water is added and extracted with EA. The combined organic layers are washed with sat. sodium chloride solution, dried, filtered and concentrated in vacuo to give the product.

MS (ESI$^+$): m/z=258 [M+H]$^+$
Intermediate A11

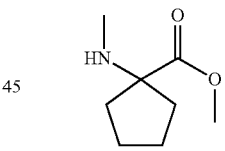

To intermediate A11-2 (1.174 g, 4.562 mmol) hydrochloride acid (4 mol/L in dioxane, 4.562 mL, 18.249 mmol) is added and the reaction mixture is stirred at room temperature for 12 h. The reaction mixture is concentrated in vacuo to give the product as hydrochloride salt.

MS (ESI$^+$): m/z=158 [M+H]$^+$
Intermediate B1-1

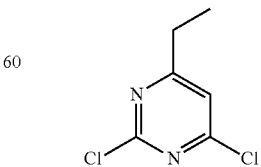

2,4,6-trichloropyrimidine (14.0 mL, 116 mmol) and copper(I) iodide (2.21 g, 11.6 mmol) are mixed under argon with THF (200 mL). At 0° C. ethylmagnesium bromide (116 mL, 116 mmol, 1M in THF) is added slowly and the reaction mixture is stirred for 2 h at 0° C., heated to room temperature and stirred for further 12 h. The reaction mixture is quenched with sat. ammonium chloride solution and extracted with tert.-butylmethyl ether. The organic phase is dried and concentrated in vacuo. The product is obtained after purification by column chromatography (silica, eluent: CH:EA 97:3).

MS (ESI$^+$): m/z=177/179/181 (2Cl) [M+H]$^+$
HPLC (Method B): Rt=1.15 min.
Intermediate B1-2

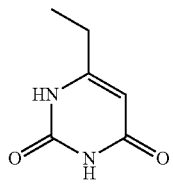

Intermediate B1-1 (19.22 g, 108.6 mmol) is mixed with HCl (75.0 mL, 32% in water) and heated to reflux for 2 h. The reaction mixture is concentrated in vacuo and freeze dried to yield the product that is used for the next step without further purification.

MS (ESI$^+$): m/z=141 [M+H]$^+$
HPLC (Method B): Rt=0.38 min
Intermediate B1-3

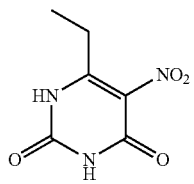

Intermediate B1-2 (14.5 g, 103 mmol) is mixed with concentrated sulfuric acid (150 mL) at 0° C. Nitric acid (9.88 mL, 155 mmol; 65% in water) is added slowly and the reaction mixture is stirred for 1 h at 0° C. and for 12 h at room temperature. The reaction mixture is poured on ice and stirred for 2 h. The precipitate is filtered off and washed with water to yield the product that is used for the next step without further purification.

MS (ESI$^+$): m/z=186 [M+H]$^+$
HPLC (Method B): Rt=0.52 min.
Intermediate B1

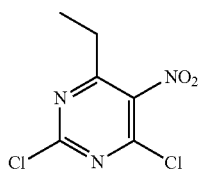

Phosphorus oxychloride (50 mL) is mixed with N,N-diethylaniline (12.8 mL, 81 mmol). Intermediate B1-3 (11.5 g, 62.1 mmol) is added at room temperature and stirred for 20 min, followed by heating to reflux for 2 h. After cooling to room temperature the reaction mixture is poured into ice water. The precipitate is filtered off and purified by column chromatography (silica, DCM/MeOH 99:1) to yield the product.

MS (ESI$^+$): m/z=220/222/224 (2Cl) [M−H]$^-$
HPLC (Method B): Rt=1.43 min.
Intermediate B2

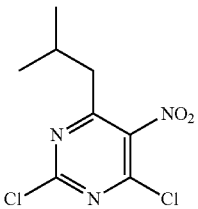

Intermediate B2 was prepared in analogy to intermediate B1 starting with 2,4,6-trichloropyrimidine and 2-methyl-propylmagnesium bromide.

HPLC (Method B): Rt=1.56 min.
Intermediate B3

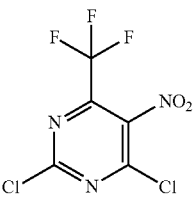 [SMILES: O=[N+]([O-])c1c(Cl)nc(Cl)nc1C(F)(F)F]

Intermediate B3 was prepared in analogy to intermediate B1 starting with 2,4-dihydroxy-5-nitro-6-(trifluoromethyl)pyrimidine.

HPLC (Method K): Rt=0.92 min.
Intermediate B4-1

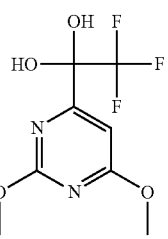

To a solution of 4-bromo-2,6-dimethoxy-pyrimidine (6.80 g, 27.94 mmol) in THF (190 mL) and diethylether (190 mL) n-butyllithium (in hexane/THF, 2.01 g, 30.74 mmol) is added dropwise with stirring at −78° C. After 4 min ethyl trifluoroacetate (4.46 g, 30.74 mmol) in THF (50 mL) is added dropwise at −78° C. The reaction mixture is stirred for 30 min at −78° C. and then the reaction is allowed to warm to room temperature slowly and stirred over night at room temperature. To the reaction mixture 1 N HCl solution is added. The resulting mixture is extracted with EA and washed with sat. sodium chloride solution and water. The organic phase is dried over sodium sulfate, filtered and the solvent is evaporated in vacuo. The residue is purified by flash column chromatography (silica gel, PE/EA=8/2) to give the product.

MS (ESI$^+$): m/z=255 [M+H]$^+$
TLC (silica gel, PE/EA 3/1): Rf=0.20

Intermediate B4-2

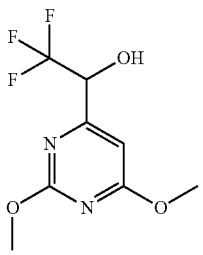 [SMILES: COc1cc(C(O)C(F)(F)F)nc(OC)n1]

To a solution of intermediate B4-1 (5.90 g, 20.89 mmol) in MeOH (100 mL) in an ice water bath sodium borohydride (7.94 g, 208.92 mmol) is added. The mixture is stirred at room temperature for 2 h. Aq. ammonium chloride solution is added and the mixture is extracted with chloroform. The combined organic layers are dried over MgSO$_4$, filtered and concentrated in vacuo to give the product which is used in the next step without further purification.

MS (ESI$^+$): m/z=239 [M+H]$^+$
TLC (silica gel, PE/EA 3/1): Rf=0.40

Intermediate B4-3

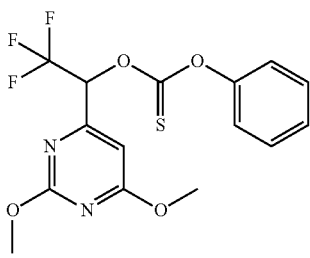 [SMILES: COc1cc(C(OC(=S)Oc2ccccc2)C(F)(F)F)nc(OC)n1]

To a solution of intermediate B4-2 (1.00 g, 3.78 mmol) and dimethylaminopyridine (1.41 g, 11.34 mmol) in DCM (100 mL) phenyl chlorothioformate (1.33 g, 7.76 mmo) is added dropwise at 0° C. Then the mixture is stirred at room temperature for 2 h. To the reaction aq. sodium chloride solution is added and the organic layer is separated, dried over MgSO$_4$, filtered and concentrated in vacuo to give the product which is used in the next step without further purification.

MS (ESI$^+$): m/z=375 [M+H]$^+$
TLC (silica gel, PE/EA 10/1): Rf=0.80

Intermediate B4-4

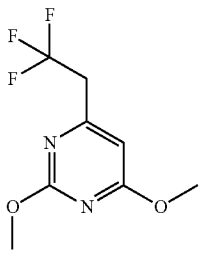

To a solution of intermediate B4-3 (12.58 g, 30.25 mmol) and 2,2'-azobis(isobutyronitrile) (1.03 g, 6.05 mmol) in toluene (200 mL) tri-n-butyltin hydride (35.93 g, 120.98 mmo) is added at room temperature and then the mixture is stirred under reflux for 2 h. Afterwards the solvent is removed in vacuo. The residue is purified by flash column chromatography (silica gel, PE/EA=9/1) to give the product.

MS (ESI$^+$): m/z=223 [M+H]$^+$
TLC (silica gel, PE/EA 10/1): Rf=0.60

Intermediate B4-5

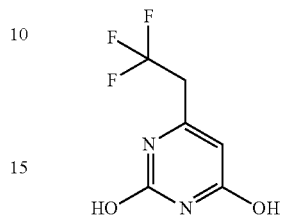

Intermediate B4-4 (1.00 g, 4.501 mmol) is added to conc. HCl (15 mL) and refluxed for 12 h. The reaction mixture is extracted with DCM. The aqueous layer is concentrated in vacuo to give the product which is used in the next step without further purification.

MS (ESI$^+$): m/z=195 [M+H]$^+$
TLC (silica gel, PE/EA 10/1): Rf=0.50

Intermediate B4-6

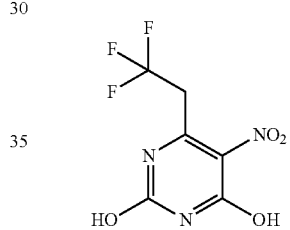

Intermediate B4-5 (0.340 g, 1.576 mmol) is dissolved in conc. H$_2$SO$_4$, then fuming HNO$_3$ is added while keeping the temperature below 5° C. The reaction is stirred at 0-5° C. for 2 h. Then the reaction is warmed to room temperature slowly and stirred over night.

The solution is poured into ice water (50 mL) and the aqueous phase is extracted with EA. The combined organic layers are concentrated in vacuo to give the crude product which was purified by flash column chromatography (silica gel, EA) to give the product.

MS (ESI$^+$): m/z=240 [M+H]$^+$

Intermediate B4

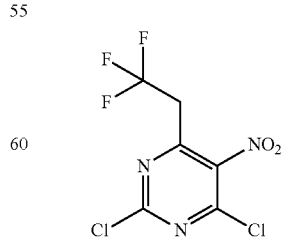

Intermediate B4-6 (1.00 g, 4.18 mmol) and phosphorus oxychloride (10 mL) is stirred at 145° C. for 3 h in a microwave oven. Afterwards the reaction mixture is concentrated in vacuo to give the product.

HPLC (Method J): Rt=0.67 min

Intermediate C1

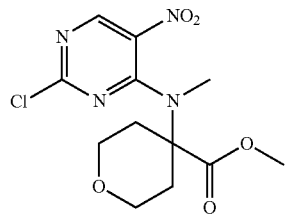 [SMILES: COC(=O)C1(N(C)c2nc(Cl)ncc2[N+](=O)[O-])CCOCC1]

Intermediate A2 (500 mg, 2.39 mmol) is mixed with water (20 mL). A solution of 2,4-dichloro-5-nitropyrimidin (463 mg, 2.39 mmol) in diethyl ether (20 mL) is added dropwise. Potassium bicarbonate (506 mg, 5.01 mmol) is added and the reaction mixture is stirred for 12 h at room temperature.

After standard workup the resulting residue is purified by column chromatography (silica, heptane:EE 100:0 to 76:24) to give the product as a solid.

MS (ESI$^+$): m/z=331/333 (Cl) [M+H]$^+$

HPLC (Method E): Rt=0.71 min

The following intermediates were prepared in an analogous manner to intermediate C1:

| Nr. | Structure / Comment | Starting materials | Mass signal(s) | $R_f$ Value or $R_t$ |
|---|---|---|---|---|
| C2 |  | 2,4-dichloro-5-nitropyrimidin and A1 | (M + H)$^+$ = 317/319 (Cl) | 1.03 min (Method D) |
| C3 |  | 2,4-dichloro-5-nitropyrimidin and A3 | (M + H)$^+$ = 303/305 (Cl) | 0.67 min (Method E) |
| C4 |  | 2,4-dichloro-5-nitropyrimidin and A4 | (M + H)$^+$ = 317/319 (Cl) | 0.69 min (Method E) |
| C5 |  | 2,4-dichloro-5-nitro-6-methylpyrimidin and A2 | (M + H)$^+$ = 345/347 (Cl) | 0.81 min (Method E) |

-continued

| Nr. | Structure Comment | Starting materials | Mass signal(s) | R_f Value or R_t |
|---|---|---|---|---|
| C6 | | A3 and B1 | (M + H)⁺ = 331/333 (Cl) | 0.81 min (Method E) |
| C7 | | A3 and B2 | (M + H)⁺ = 359/361 (Cl) | 0.92 min (Method E) |
| C8 | | 2,4-dichloro-5-nitropyrimidin and A5 | (M + H)⁺ = 361/363 (Cl) | 0.76 min (Method E) |
| C9 | | 2,4-dichloro-5-nitropyrimidin and A6 | (M + H)⁺ = 377/379 (Cl) | 1.46 min (Method A) |
| C10 | | A1 and B3 | (M + H)⁺ = 385/387 (Cl) | 0.64 min (Method I) |
| C11 | | B1 and 1-amino-cyclopropan-1-carboxylic acid ethylester HCl | (M + H)⁺ = 315/317 (Cl) | 1.25 min (Method L) |

-continued

| Nr. | Structure Comment | Starting materials | Mass signal(s) | $R_f$ Value or $R_t$ |
|---|---|---|---|---|
| C13 | | A7 and 2,4-dichloro-5-nitro-pyrimidine | $(M + H)^+$ = 331/333 (Cl) | 1.11 min (Method N) |
| C15 | | A9 and 2,4-dichloro-5-nitro-pyrimidine | $(M - H)^-$ = 287/289 (Cl) | 0.77 min (Method H) |
| C16 | | 4-oxepanecarboxylic acid-4-amino-methyl ester (WO 2011053948) and 2,4-dichloro-5-nitro-pyrimidine | $(M - H)^-$ = 331/333 (Cl) | 0.51 min (Method I) |
| C17 | | methyl 1-(methylamino)cyclopropane-1-carboxylate and 2,4-dichloro-5-nitro-pyrimidine | $(M - H)^-$ = 287/289 (Cl) | 0.57 min (Method J) |
| C18 | | A10 and 2,4-dichloro-5-nitro-pyrimidine | $(M - H)^-$ = 327/329 (Cl) | 1.26 min (Method L) |
| C19 | | A11 and 2,4-dichloro-5-nitro-pyrimidine | $(M + H)^+$ = 315/317 (Cl) | 0.68 min (Method J) |

| Nr. | Structure Comment | Starting materials | Mass signal(s) | $R_f$-Value or $R_t$ |
|---|---|---|---|---|
| C20 | 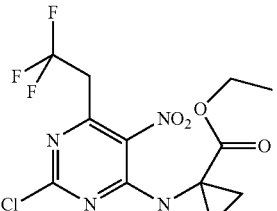 | B4 and 1-amino-cyclopropane-1-carboxylic acid ethyl ester HCl | $(M + H)^+ = 369/371$ (Cl) | 0.70 min (Method J) |

Intermediate C20-2

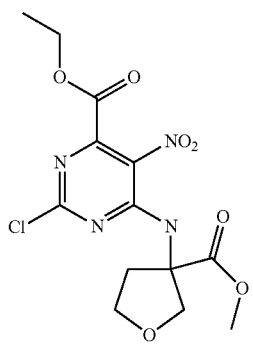 [SMILES: CCOC(=O)c1nc(Cl)nc(NC2(C(=O)OC)CCOC2)c1[N+](=O)[O-]]

A solution of intermediate A3 (455 mg, 2.255 mmol) and DIPEA (1.156 mL, 6.676 mmol) in 20 mL DCM is added dropwise to 2,6-dichloro-5-nitro-pyrimidine-4-carboxylic acid methyl ester hydrochloride (600 mg, 2.255 mmol) in 40 mL DCM at −70° C. and stirring is continued at −70° C. for 1 h and at room temperature for 2 h.

To the reaction mixture 60 mL potassium bicarbonate solution (10%) is added and the layers are separated. The organic layer is concentrated in vacuo and the residue is purified by preparative HPLC (eluent A: water+0.15% TFA, eluent B: ACN) to give the product.

HPLC (Method N): Rt=1.10 min

Intermediate C20-3

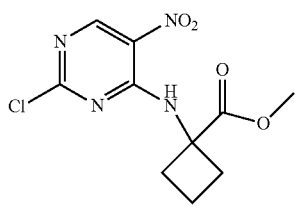 [SMILES: COC(=O)C1(Nc2nc(Cl)ncc2[N+](=O)[O-])CCC1]

To a solution of cyclobutanecarboxylic acid 1-amino-methyl ester hydrochloride (10.0 g, 60.38 mmol; WO 2009146347) and potassium carbonate (301.9 mL, 120.76 mmol) in THF (300 mL) a solution of 2,4-dichloro-5-nitro-pyrimidine (11.71 g, 60.38 mmol) in THF (50 mL) is added dropwise at 0° C. The resulting mixture was stirred at this temperature for 2 h. The mixture was diluted with DCM. The organic layer was separated, washed with water, dried over Na2SO4 and concentrated in vacuo. The crude product is purified by column chromatography on silica gel (PE/EA=50/1) to give the product.

MS (ESI⁺): m/z=287/289 (Cl) [M+H]⁺

TLC (silica gel, PE/EA=5/1): Rf=0.60

Intermediate C20-4

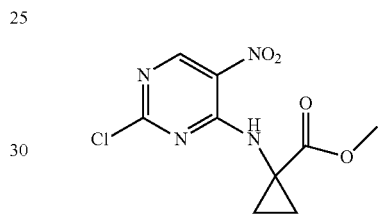

2,4-Dichloro-5-nitrol-pyrimidine (21.31 g, 109.9 mmol) in THF (200 mL) is added to the mixture of 1-amino-cyclopropylcarboxylic acid methyl ester (11.50 g, 13.03 mmol) and potassium carbonate (13.81 g, 99.88 mmol) in THF (200 mL) and H2O (200 mL) at 0° C. Afterwards the mixture is stirred at room temperature overnight.

The solvent is removed in vacuo and the resulting oil was purified by a flash column chromatography (silica gel, PE/EA=5/1) to afford the product.

TLC (silica gel, PE/EA=5/1): Rf=0.60

Intermediate D1

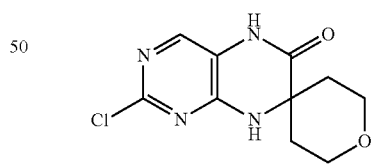

Intermediate C2 (1.48 g, 2.34 mmol) is mixed with acetic acid (11.4 mL, 0.20 mmol) and heated to 60° C. Iron filings (639 mg, 11.4 mmol) are added in portions and the reaction mixture is stirred at 70° C. for 1 h and filtered then over celite and activated carbon. The filtrate is concentrated in vacuo. The residue is purified by preparative HPLC (eluent A: water+0.13% TFA, eluent B: MeOH) to give the product as a solid.

MS (ESI⁺): m/z=255/257 (Cl) [M+H]⁺

HPLC (Method A): Rt=0.65 min

The following intermediates were prepared in an analogous manner to intermediate D1:

| Nr. | Structure / Comment | Starting materials | Mass signal(s) | $R_f$ Value or $R_t$ |
|---|---|---|---|---|
| D2 | | C1 | $(M + H)^+ = 317/319$ (Cl) | 0.99 min (Method B) |
| D3 | | C3 | $(M + H)^+ = 241/243$ (Cl) | 0.98 min (Method B) |
| D4 | | C4 | $(M + H)^+ = 255/257$ (Cl) | 0.84 min (Method B) |
| D5 | | C5 | $(M + H)^+ = 283/285$ (Cl) | 0.96 min (Method B) |
| D6 | | C6 | $(M + H)^+ = 269/271$ (Cl) | 0.85 min (Method B) |
| D7 | | C7 | $(M + H)^+ = 297/299$ (Cl) | 1.11 min (Method B) |
| D8 | | C8 | $(M + H)^+ = 285/287$ (Cl) | 0.88 min (Method B) |
| D9 | | C9 | $(M + H)^+ = 315/317$ (Cl) | 1.39 min (Method A) |

-continued

| Nr. | Structure Comment | Starting materials | Mass signal(s) | R_f Value or R_t |
|---|---|---|---|---|
| D11 | (chloro-pteridinone spiro-oxepane) | C13 | (M + H)⁺ = 269/271 (Cl) | 0.73 min (Method N) |
| D13 | (chloro-pteridinone spiro-cyclobutane) | C20-3 | (M + H)⁺ = 225/227 (Cl) | Rf = 0.40 (TLC: silica gel, DCM/MeOH = 20/1) |
| D14 | (chloro-pteridinone spiro-cyclopropane) | C20-4 | (M + H)⁺ = 211/213 (Cl) | Rf = 0.40 (TLC: silica gel, DCM/MeOH = 20/1) |
| D15 | (chloro-pteridinone spiro-cyclobutane) | C20-3 | (M + H)⁺ = 225/227 (Cl) | Rf = 0.40 (TLC: silica gel, DCM/MeOH = 20/1) |
| D16 | (chloro-pteridinone spiro-norbornane) | C18 | (M + H)⁺ = 265/267 (Cl) | 0.81 min (Method H) |
| D17 | (chloro-N-methyl-pteridinone spiro-cyclopentane) | C19 | (M + H)⁺ = 253/255 (Cl) | 0.86 min (Method H) |
| D18 | (chloro-trifluoroethyl-pteridinone spiro-cyclopropane) | C20 | (M + H)⁺ = 293/295 (Cl) | 0.65 min (Method H) |

Intermediate D18-1

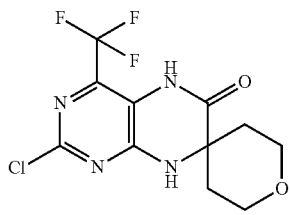

Intermediate C10 (0.52 g, 1.35 mmol) in methanol is hydrogenated ($H_2$ atmosphere, 50 psi) with raney nickel at 60° C. for 17 h. The reaction mixture is heated under reflux for 4 h. The mixture is evaporated to give the product.

MS (ESI$^+$): m/z=323/325 (Cl) [M+H]$^+$
HPLC (Method I): Rt=0.44 min

The following intermediates were prepared in an analogous manner to intermediate D18-1:

| Nr. | Structure Comment | Starting materials | Mass signal(s) | $R_f$ Value or $R_t$ |
|---|---|---|---|---|
| D18-2 | | C20-2 | $(M + H)^+ = 313/315$ (Cl) | 0.79 min (Method N) |
| D18-3 | | C15 | $(M + H)^+ = 227/229$ (Cl) | 0.16 min (Method O) |
| D18-4 | | C16 | $(M + H)^+ = 269/271$ (Cl) | 0.35 min (Method J) |
| D18-5 | | C17 | $(M + H)^+ = 225/227$ (Cl) | 0.69 min (Method H) |

Intermediate E1

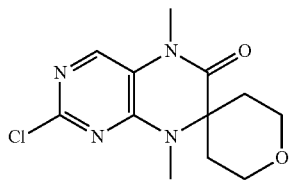 [SMILES: CN1C(=O)C2(CCOCC2)N(C)c2nc(Cl)ncc21]

Intermediate D2 (500 mg, 1.96 mmol) is mixed with N,N-dimethylformamide (15 mL) and sodium hydride (60% in oil, 196 mg, 4.91 mmol) is added. Methyl iodide (0.306 mL, 4.91 mmol) is added and the reaction mixture is stirred for 12 h at room temperature. The solvent is evaporated and the residue is extracted with ethyl acetate and water. The organic phase is dried over magnesium sulfate and concentrated in vacuo to give the product as an oil.

MS (ESI$^+$): m/z=283/285 (Cl) [M+H]$^+$
HPLC (Method A): Rt=0.96 min

The following intermediates were prepared in an analogous manner to intermediate E1:

Intermediate E2

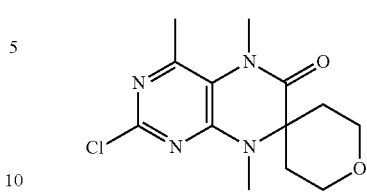

Intermediate D5 (28.0 mg, 0.10 mmol) is dissolved in DMF (2 mL). Potassium carbonate (27.4 mg, 0.20 mmol) and methyl iodide (4.40 μL, 0.12 mmol) are added and the resulting mixture is stirred at room temperature for 2 h. The solvent is evaporated and the residue is extracted with ethyl acetate and water. The organic phase is dried over magnesium sulfate and concentrated in vacuo to give the product as a solid.

MS (ESI$^+$): m/z=297/299 (Cl) [M+H]$^+$
HPLC (Method E): Rt=0.70 min

| Nr. | Structure Comment | Starting materials | Mass signal(s) | $R_f$ Value or $R_t$ |
|---|---|---|---|---|
| E1b | | D18-1 | (M + H)$^+$ = 351/353 (Cl) | 0.86 min (Method O) |
| E1c | | C11 | (M + H)$^+$ = 267/269 (Cl) | 1.02 min (Method L) |
| E1e | | D13 | (M + H)$^+$ = 253/255 (Cl) | Rf = 0.40 (TLC: silica gel, PE/EA = 1/1) |
| E1f | | D18 | (M + H)$^+$ = 321/323 (Cl) | 0.60 min (Method J) |

The following intermediates were prepared in an analogous manner to intermediate E2.

| Nr. | Structure | Starting materials / Comment | Mass signal(s) | $R_f$ Value or $R_t$ |
|---|---|---|---|---|
| E3 | 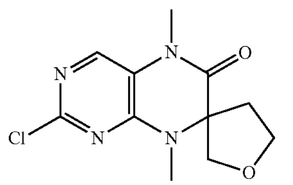 [SMILES: CN1C(=O)C2(CCOC2)N(C)c2nc(Cl)ncc21] | D4 and methyl iodide | $(M + H)^+ = 269/271$ (Cl) | 0.90 min (Method D) |
| E4 | 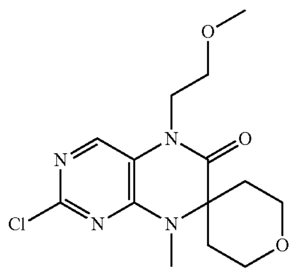 [SMILES: COCCN1C(=O)C2(CCOCC2)N(C)c2nc(Cl)ncc21] | D2 and 2-bromoethyl-methylether | $(M + H)^+ = 327/329$ (Cl) | 0.55 min (Method G) |
| | Purification with preparative HPLC, obtained as trifluoroacetate salt. | | | |
| E5 | 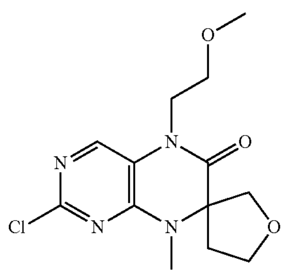 [SMILES: COCCN1C(=O)C2(CCOC2)N(C)c2nc(Cl)ncc21] | D4 and 2-bromoethyl-methylether | $(M + H)^+ = 313/315$ (Cl) | 1.10 min (Method E) |
| | Purification with preparative HPLC, obtained as trifluoroacetate salt. | | | |
| E6 | 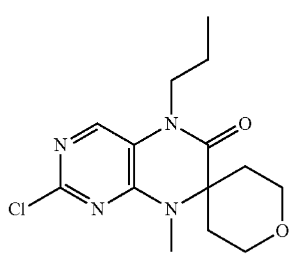 [SMILES: CCCN1C(=O)C2(CCOCC2)N(C)c2nc(Cl)ncc21] | D2 and 1-iodopropane | $(M + H)^+ = 311/313$ (Cl) | 0.77 min (Method E) |
| | Purification with preparative HPLC, obtained as trifluoroacetate salt. | | | |
| E7 | 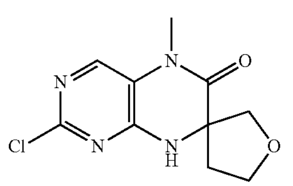 [SMILES: CN1C(=O)C2(CCOC2)Nc2nc(Cl)ncc21] | D3 and methyliodide | $(M + H)^+ = 255/257$ (Cl) | 0.52 min (Method E) |
| | Purification with preparative HPLC, obtained as trifluoroacetate salt | | | |

| Nr. | Structure | Starting materials Comment | Mass signal(s) | $R_f$-Value or $R_t$ |
|---|---|---|---|---|
| E8 | 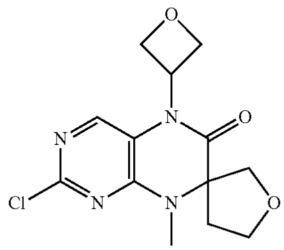 [SMILES: CN1c2nc(Cl)ncc2N(C2COC2)C(=O)C12CCOC2] | D4 and 3-iodooxetane | $(M + H)^+ = 311/313$ (Cl) | 0.94 min (Method B) |
| | Heated over night at 100° C.; Purification with preparative HPLC. | | | |
| E9 | 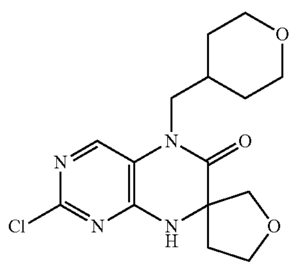 [SMILES: O=C1N(CC2CCOCC2)c2cnc(Cl)nc2NC12CCOC2] | D3 and 4-(iodomethyl)-tetrahydro-pyrane | $(M + H)^+ = 339/341$ (Cl) | 0.63 min (Method E) |
| | Purification with preparative HPLC. | | | |
| E10 | 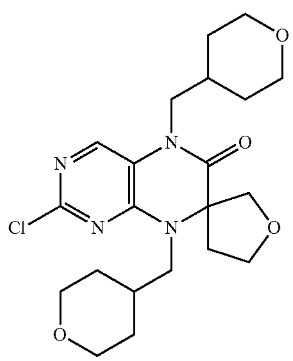 [SMILES: O=C1N(CC2CCOCC2)c2cnc(Cl)nc2N(CC2CCOCC2)C12CCOC2] | D3 and 4-(iodomethyl)-tetrahydro-pyrane | $(M + H)^+ = 437/439$ (Cl) | 0.80 min (Method E) |
| | Purification with preparative HPLC. | | | |
| E11 | 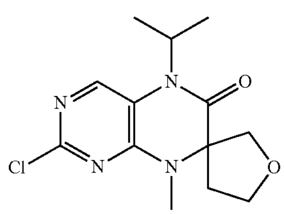 [SMILES: CC(C)N1C(=O)C2(CCOC2)N(C)c2nc(Cl)ncc21] | D4 and 2-iodopropane | $(M + H)^+ = 297/299$ (Cl) | 0.75 min (Method E) |
| | Heated in a pressure tube over night at 100° C.; Purification with preparative HPLC. | | | |
| E12 | 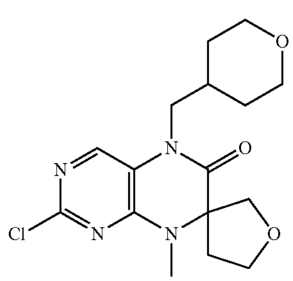 [SMILES: CN1c2nc(Cl)ncc2N(CC2CCOCC2)C(=O)C12CCOC2] | E9 and methyliodide | $(M + H)^+ = 353/355$ (Cl) | 0.74 min (Method E) |
| | Heated in a pressure tube over night at 100° C.; Purification with preparative HPLC. | | | |

-continued

| Nr. | Structure | Starting materials Comment | Mass signal(s) | $R_f$ Value or $R_t$ |
|---|---|---|---|---|
| E13 | 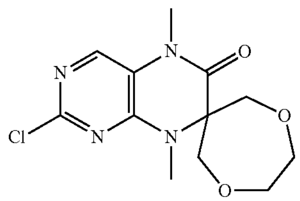 [SMILES: CN1C(=O)C2(COCCOC2)N(C)c2nc(Cl)ncc21] | D8 and methyliodide | $(M + H)^+ = 299/301$ (Cl) | 0.67 min (Method E) |
| E14 | 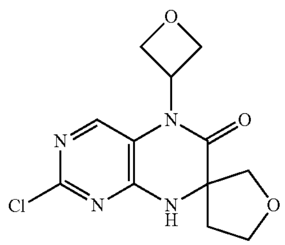 [SMILES: O=C1N(C2COC2)c2cnc(Cl)nc2NC12CCOC2] | D3 and 3-iodooxetane | $(M + H)^+ = 297/299$ (Cl) | 0.74 min (Method B) |
| | Heated over night at 100° C.; Purification with preparative HPLC. | | | |
| E15 | 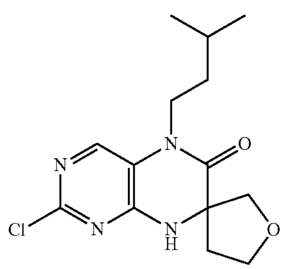 [SMILES: CC(C)CCN1C(=O)C2(CCOC2)Nc2nc(Cl)ncc21] | D3 and 1-bromo-3-methyl-butane | $(M + H)^+ = 311/313$ (Cl) | 0.83 min (Method E) |
| | Purification with preparative HPLC. | | | |
| E16 | 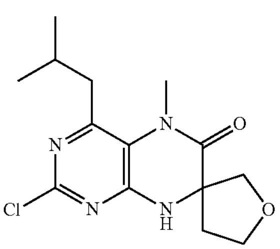 [SMILES: CC(C)Cc1nc(Cl)nc2c1N(C)C(=O)C1(CCOC1)N2] | D7 and methyliodide | $(M + H)^+ = 311/313$ (Cl) | 0.76 min (Method E) |
| | Purification with preparative HPLC. | | | |
| E17 | 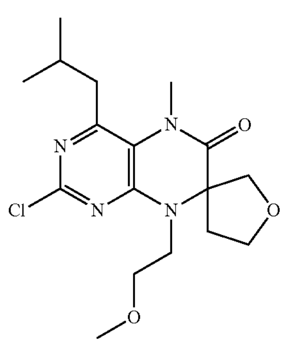 [SMILES: COCCN1c2nc(Cl)nc(CC(C)C)c2N(C)C(=O)C12CCOC2] | E16 and 2-bromoethyl-methylether | $(M + H)^+ = 369/371$ (Cl) | 0.90 min (Method E) |
| | Purification with preparative HPLC. | | | |

-continued

| Nr. | Structure | Starting materials Comment | Mass signal(s) | R_f Value or R_t |
|---|---|---|---|---|
| E18 | 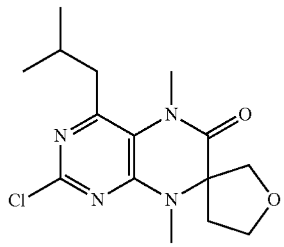 [SMILES: CC(C)Cc1nc(Cl)nc2c1N(C)C(=O)C1(CCOC1)N2C] | D7 and methyliodide | (M + H)⁺ = 325/327 (Cl) | 0.87 min (Method E) |
| | Purification with preparative HPLC. | | | |
| E19 | 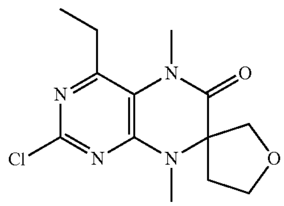 [SMILES: CCc1nc(Cl)nc2c1N(C)C(=O)C1(CCOC1)N2C] | D6 and methyliodide | (M + H)⁺ = 297/299 (Cl) | 0.74 min (Method E) |
| | Purification with preparative HPLC. | | | |
| E20 | 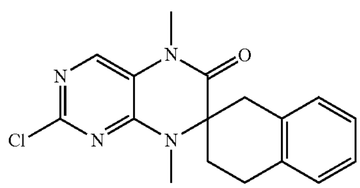 [SMILES: CN1C(=O)C2(CCc3ccccc3C2)N(C)c2nc(Cl)ncc21] | D9 and methyliodide | (M + H)⁺ = 329/331 (Cl) | 1.43 min (Method A) |
| | Purification with preparative HPLC. | | | |
| E20a | 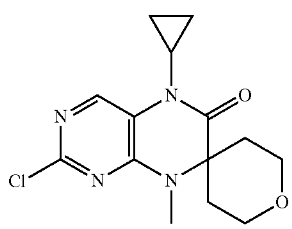 [SMILES: CN1c2nc(Cl)ncc2N(C2CC2)C(=O)C12CCOCC2] | E22 and methyliodide | (M + H)⁺ = 309/311 (Cl) | 0.52 min (Method J) |
| | Purification with preparative HPLC. | | | |
| E20b | 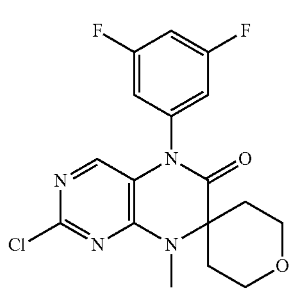 [SMILES: CN1c2nc(Cl)ncc2N(c2cc(F)cc(F)c2)C(=O)C12CCOCC2] | E23 and methyliodide | (M + H)⁺ = 381/383 (Cl) | 0.64 min (Method J) |
| | Purification with preparative HPLC. | | | |

-continued

| Nr. | Structure | Starting materials Comment | Mass signal(s) | $R_f$-Value or $R_t$ |
|---|---|---|---|---|
| E20c | 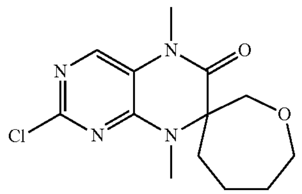 [SMILES: CN1C(=O)C2(CCCCOC2)N(C)c2nc(Cl)ncc21] | D11 and methyliodide | $(M + H)^+ = 297/299$ (Cl) | 1.02 min (Method H) |
| | Purification with preparative HPLC. | | | |
| E20e | 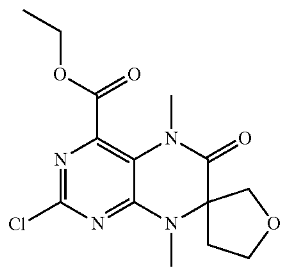 [SMILES: CCOC(=O)c1nc(Cl)nc2c1N(C)C(=O)C1(CCOC1)N2C] | D18-2 and methyliodide | $(M + H)^+ = 341/343$ (Cl) | 1.24 min (Method N) |
| | Purification with preparative HPLC. | | | |
| E20f | 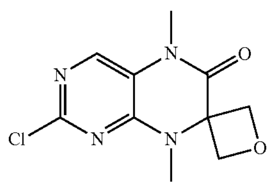 [SMILES: CN1C(=O)C2(COC2)N(C)c2nc(Cl)ncc21] | D18-3 and methyliodide | $(M + H)^+ = 255/257$ (Cl) | 0.66 min (Method H) |
| | Purification with preparative HPLC. | | | |
| E20g | 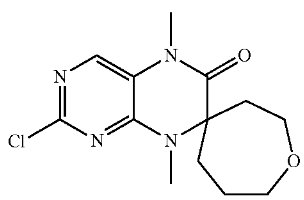 [SMILES: CN1C(=O)C2(CCCOCC2)N(C)c2nc(Cl)ncc21] | D18-4 and methyliodide | $(M + H)^+ = 297/299$ (Cl) | 0.44 min (Method I) |
| | Purification with preparative HPLC. | | | |
| E20h | 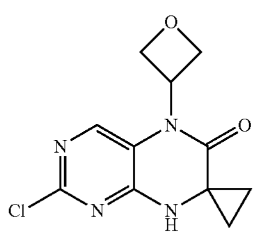 [SMILES: O=C1N(C2COC2)c2cnc(Cl)nc2NC12CC2] | D14 and 3-iodooxetane | $(M + H)^+ = 267/269$ (Cl) | 0.65 min (Method H) |
| | Heated over night at 100° C.; Purification with preparative HPLC. | | | |
| E20i | 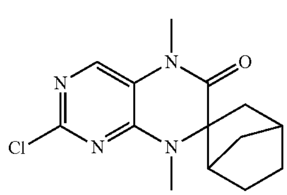 [SMILES: CN1C(=O)C2(CC3CCC2C3)N(C)c2nc(Cl)ncc21] | D16 and methyliodide | $(M + H)^+ = 293/295$ (Cl) | 0.64 min (Method J) |
| | Purification with preparative HPLC. | | | |

-continued

| Nr. | Structure | Starting materials Comment | Mass signal(s) | $R_f$-Value or $R_t$ |
|---|---|---|---|---|
| E20j | 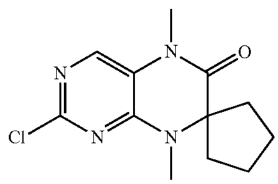 [SMILES: CN1C(=O)C2(CCCC2)N(C)c2nc(Cl)ncc21] | D17 and 3-methyliodide | $(M + H)^+ =$ 267/269 (Cl) | 0.57 min (Method J) |
| | Purification with preparative HPLC. | | | |

Intermediate E21

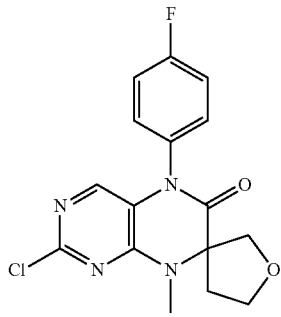 [SMILES: CN1c2nc(Cl)ncc2N(c2ccc(F)cc2)C(=O)C12CCOC2]

Intermediate D4 (35.0 mg, 0.14 mmol) is mixed with 1 mL dichloromethane. 57.7 mg (0.41 mmol) 4-fluorophenylboronic acid, 22.1 μL pyridine and 37.4 mg (0.21 mmol) copper (II)acetate are added and the resulting mixture is stirred at room temperature over night. The reaction mixture is filtered over celite and washed with DCM. The filtrate is extracted with sodium bicarbonate, phases are separated and the organic phase is concentrated. The resulting residue is treated with diisopropyl ether and filtered to yield the product.

MS (ESI$^+$): m/z=349/351 (Cl) [M+H]$^+$

HPLC (Method G): Rt=0.59 min

The following intermediates were prepared in an analogous manner to intermediate E21:

| Nr. | Comment | Structure | Starting materials | Mass signal(s) | $R_f$-Value or $R_t$ |
|---|---|---|---|---|---|
| E22 | | 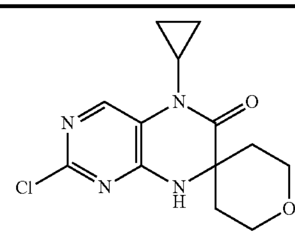 | D1 and cyclopropylboronic acid | $(M + H)^+ =$ 295/297 (Cl) | 0.73 min (Method H) |
| | Purification with preparative HPLC. | | | | |
| E23 | | 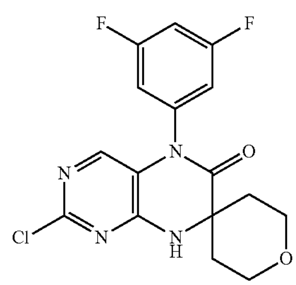 | D1 and 3,5-difluorophenylboronic acid | $(M + H)^+ =$ 367/369 (Cl) | 0.94 min (Method H) |
| | Purification with preparative HPLC. | | | | |

-continued

| Nr. Comment | Structure | Starting materials | Mass signal(s) | R$_f$ Value or R$_t$ |
|---|---|---|---|---|
| E23b | (structure) | D1 and 4-fluorophenylboronic acid | (M + H)$^+$ = 349/351 (Cl) | 0.51 min (Method J) |

Purification with preparative HPLC.

| E23c | (structure) | D3 and cyclopropylboronic acid | (M + H)$^+$ = 281/283 (Cl) | 0.35 min (Method I) |
|---|---|---|---|---|

Purification with preparative HPLC.

| E23d | (structure) | D18-5 and fluorophenylboronic acid | (M + H)$^+$ = 319/321 (Cl) | 0.54 min (Method I) |
|---|---|---|---|---|

Purification with preparative HPLC.

Intermediate E24-1

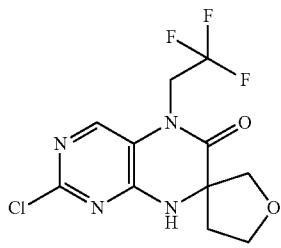 [SMILES: O=C1N(CC(F)(F)F)c2cnc(Cl)nc2NC12CCOC2]

To intermediate D3 (150 mg, 0.62 mmol) in 5 mL DMF potassium carbonate (215 mg, 1.56 mmol) and 2,2,2-trifluoroethyl trifluoromethanesulfonate (135 µL, 0.94 mmol) are added and the resulting mixture is stirred at room temperature for 1 h. To the reaction mixture water is added and then extracted with EA. The combined organic layers are washed with sat. NaCl solution dried and evaporated. The residue is purified by preparative HPLC (eluent A: water+0.15% TFA, eluent B: ACN) to give the product.

MS (ESI$^+$): m/z=323/325 (Cl) [M+H]$^+$

HPLC (Method I): Rt=0.43 min

The following intermediates were prepared in an analogous manner to intermediate E24-1:

| Nr. | Comment | Structure | Starting materials | Mass signal(s) | $R_f$-Value or $R_t$ |
|---|---|---|---|---|---|
| E24-1b | Purification with preparative HPLC. | 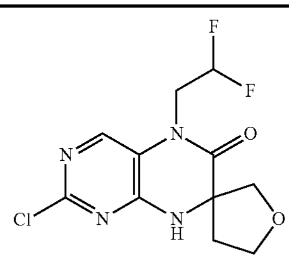 | D3 and 2,2-difluoroethyl-trifluoromethane-sulfonate | (M + H)$^+$ = 306/307 (Cl) | 0.39 min (Method J) |
| E24-1c | Purification with preparative HPLC. | 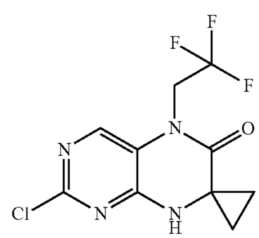 [SMILES: O=C1N(CC(F)(F)F)c2cnc(Cl)nc2NC12CC2] | D14 and 2,2,2-trifluoroethyl-trifluoromethane-sulfonate | (M + H)$^+$ = 293/295 (Cl) | 0.48 min (Method J) |
| E24-1d | Purification with preparative HPLC. | 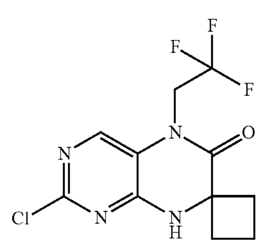 [SMILES: O=C1N(CC(F)(F)F)c2cnc(Cl)nc2NC12CCC2] | D15 and 2,2,2-trifluoroethyl-trifluoromethane-sulfonate | (M + H)$^+$ = 307/309 (Cl) | 0.49 min (Method I) |
| E24-1e | Purification with preparative HPLC. | 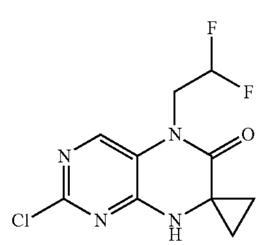 [SMILES: O=C1N(CC(F)F)c2cnc(Cl)nc2NC12CC2] | D14 and 2,2-difluoroethyl-trifluoromethane-sulfonate | (M + H)$^+$ = 275/277 (Cl) | 0.43 min (Method J) |

-continued

| Nr. Comment | Structure | Starting materials | Mass signal(s) | $R_f$-Value or $R_t$ |
|---|---|---|---|---|
| E24-1f | 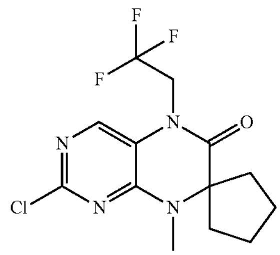 [SMILES: CN1c2nc(Cl)ncc2N(CC(F)(F)F)C(=O)C12CCCC2] | D17 and 2,2,2-trifluoroethyl-trifluoromethane-sulfonate | $(M + H)^+ =$ 335/337 (Cl) | 0.70 min (Method J) |

Purification with preparative HPLC.

Intermediate E24

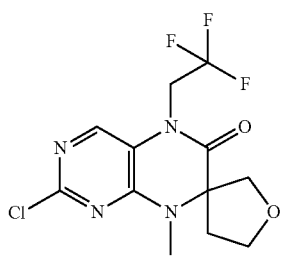 [SMILES: CN1c2nc(Cl)ncc2N(CC(F)(F)F)C(=O)C12CCOC2]

Intermediate E24 was prepared in analogy to intermediate E1 starting with E24-1 and methyliodide.

MS (ESI$^+$): m/z=337/339 (Cl) [M+H]$^+$

HPLC (Method I): Rt=0.54 min

The following intermediates were prepared in an analogous manner to intermediate E24:

| Nr. Comment | Structure | Starting materials | Mass signal(s) | $R_f$-Value or $R_t$ |
|---|---|---|---|---|
| E24b | 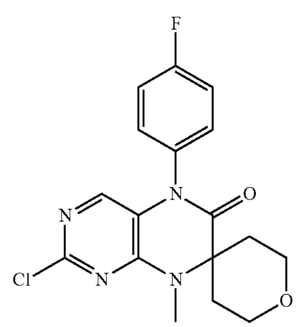 [SMILES: CN1c2nc(Cl)ncc2N(c2ccc(F)cc2)C(=O)C12CCOCC2] | E23b and methyliodide | $(M + H)^+ =$ 363/365 (Cl) | 0.59 min (Method J) |

Purification with preparative HPLC.

Intermediate E25-1

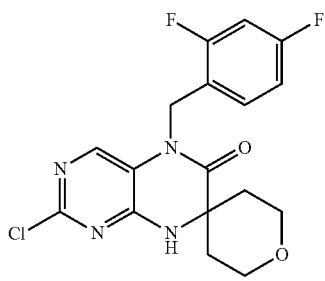 [SMILES: O=C1N(Cc2ccc(F)cc2F)c2cnc(Cl)nc2NC12CCOCC2]

To intermediate D1 (300 mg, 1.18 mmol) in 5 mL DMF and 5 mL THF potassium carbonate (326 mg, 2.36 mmol) and 1-bromomethyl-2,4-difluoro-benzene (488 mg, 2.36 mmol) are added and the resulting mixture is stirred at 60° C. for 1 h. To the reaction mixture water and DCM are added and the layers are separated. The organic layer is evaporated in vacuo. The residue is purified by preparative HPLC (eluent A: water+0.15% TFA, eluent B: ACN) to give the product.

MS (ESI$^+$): m/z=381/383 (Cl) [M+H]$^+$

HPLC (Method L): Rt=1.10 min

The following intermediates were prepared in an analogous manner to intermediate E25-1:

| Nr. Comment | Structure | Starting materials | Mass signal(s) | $R_f$-Value or $R_t$ |
|---|---|---|---|---|
| E25-1b Purification with preparative HPLC. | | D3 and 2-(1-bromoethyl) pyridine HBr | (M + H)$^+$ = 346/348 (Cl) | 0.65 min (Method L) |

Intermediate E25

Intermediate E25 was prepared in analogy to intermediate E2 starting with E25-1 and methyliodide.

MS (ESI$^+$): m/z=395/397 (Cl) [M+H]$^+$

HPLC (Method L): Rt=1.20 min

The following intermediates were prepared in an analogous manner to intermediate E25:

| Nr. | Comment | Structure | Starting materials | Mass signal(s) | $R_f$ Value or $R_t$ |
|---|---|---|---|---|---|
| E25b | Purification with preparative HPLC. | (pyridyl-CH(CH₃)- substituted pteridinone with spiro-tetrahydrofuran, Cl, N-Me) | E25-1b and methyliodide | $(M + H)^+$ = 360/362 (Cl) | 0.78 min (Method L) |
| E25c | Purification with preparative HPLC. | (cyclopropyl substituted pteridinone with spiro-tetrahydrofuran, Cl, N-Me) | E23c and methyliodide | $(M + H)^+$ = 295/297 (Cl) | 0.45 min (Method I) |
| E25d | Purification with preparative HPLC. | (CHF-CH₂F substituted pteridinone with spiro-tetrahydrofuran, Cl, N-Me) | E24-1b and methyliodide | $(M + H)^+$ = 320/321 (Cl) | 0.49 min (Method J) |
| E25e | Purification with preparative HPLC. | (CF₂-CH₂F substituted pteridinone with spiro-cyclopropyl, Cl, N-Me) | E24-1c and methyliodide | $(M + H)^+$ = 307/309 (Cl) | 0.59 min (Method J) |
| E25f | Purification with preparative HPLC. | (CF₂-CH₂F substituted pteridinone with spiro-cyclobutyl, Cl, N-Me) | E24-1d and methyliodide | $(M + H)^+$ = 321/323 (Cl) | 0.59 min (Method I) |

-continued

| Nr. | Comment | Structure | Starting materials | Mass signal(s) | $R_f$ Value or $R_t$ |
|---|---|---|---|---|---|
| E25g | Purification with preparative HPLC. | 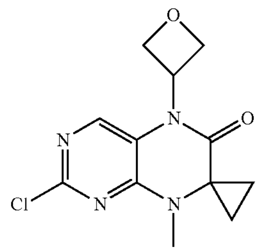 [SMILES: CN1c2nc(Cl)ncc2N(C2COC2)C(=O)C12CC2] | E20h and methyliodide | $(M + H)^+ =$ 281/283 (Cl) | 0.85 min (Method H) |
| E25h | Purification with preparative HPLC. | 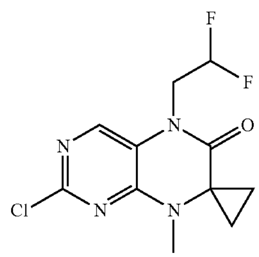 [SMILES: CN1c2nc(Cl)ncc2N(CC(F)F)C(=O)C12CC2] | E24-1e and methyliodide | $(M + H)^+ =$ 289/291 (Cl) | 0.53 min (Method J) |

Intermediate E28

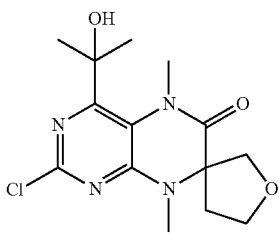 [SMILES: CN1C(=O)C2(CCOC2)N(C)c2nc(Cl)nc(C(C)(C)O)c21]

To intermediate E20e (115 mg, 0.337 mmol) in THF (15 mL) under argon atmosphere methylmagnesiumbromide (1.4 mol/L in THF/toluene, 1.446 mL, 2.025 mmol) is added under cooling and afterwards the reaction mixture is warmed to room temperature. 30 mL ammonia chloride solution (27%) is added under cooling and the mixture is extracted with EA. The combined organic layers are concentrated in vacuo and the residue is purified by preparative HPLC (eluent A: water+0.15° A) TFA, eluent B: ACN) to give the product.

MS (ESI$^+$): m/z=327/329 (Cl) [M+H]$^+$
HPLC (Method N): Rt=0.95 min.

Intermediate E29-1

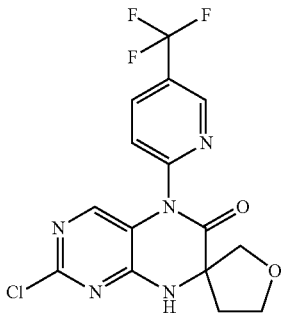 [SMILES: O=C1N(c2ccc(C(F)(F)F)cn2)c2cnc(Cl)nc2NC12CCOC2]

Intermediate D3 (300.0 mg, 1.247 mmol) is mixed with 16 mL DCM. Lithium trihydroxy(5-(trifluoromethyl)pyridin-2-yl)borate (401.8 mg, 1.870 mmol), pyridine (197 μL, 2.493 mmol), triethylamine (175 μL, 1.247 mmol) and copper(II) acetate (452.9 mg, 2.493 mmol) are added and the resulting mixture is stirred at 60° C. over night. The reaction mixture is filtered over celite and washed with DCM. The filtrate is extracted with sodium bicarbonate, phases are separated and the organic phase is concentrated. The residue is purified by preparative HPLC (eluent A: water+0.15% TFA, eluent B: ACN) to give the product.

MS (ESI$^+$): m/z=386/388 (Cl) [M+H]$^+$

HPLC (Method N): Rt=0.97 min

Intermediate E29

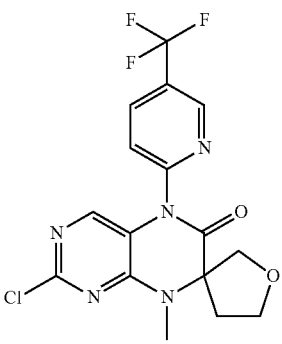 [SMILES: CN1c2nc(Cl)ncc2N(c2ccc(C(F)(F)F)cn2)C(=O)C12CCOC2]

Intermediate E29 was prepared in analogy to intermediate E2 starting with E29-1 and methyliodide.

MS (ESI⁺): m/z=400/402 (Cl) [M+H]⁺

Intermediate F1

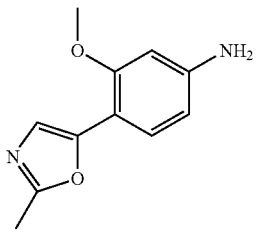

Intermediate F1 was prepared according to WO 2010/089292.

Intermediate F2

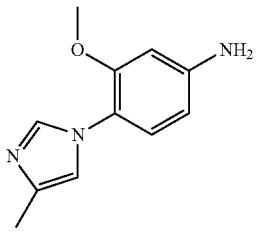

Intermediate F2 was prepared according to WO 2011/014535.

Intermediate F3

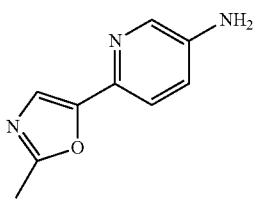

Intermediate F3 was prepared according to WO 2010/089292.

Intermediate F4

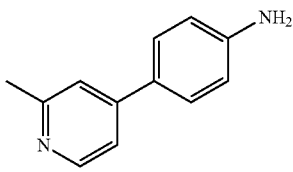

Intermediate F4 was prepared according to WO 2009/075874.

Intermediate F5

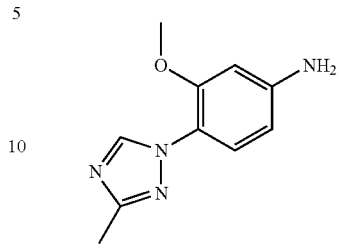

Intermediate F5 was prepared according to WO 2011/014535.

Intermediate F6

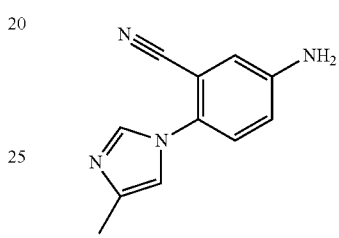

Intermediate F6 was prepared according to WO 2009/103652.

Intermediate F7

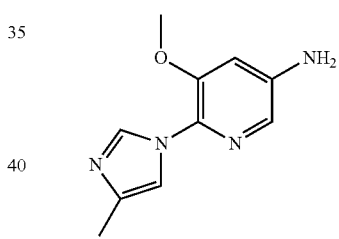

Intermediate F7 was prepared according to WO 2010/132015.

Intermediate F8-1

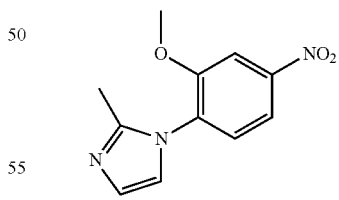

To 2-methylimidazole (500.0 mg, 6.090 mmol) in DMF (10 mL) potassium carbonate (1.683 g, 12.180 mmol) and 4-fluoro-3-methoxynitrobenze (1.042 g, 6.090 mmol) are added and the resulting mixture is stirred at 85° C. for 12 h in a pressure tube. Afterwards the solvent is removed in vacuo, sodium bicarbonate solution (9%) is added and extracted with EA. The combined organic layers are washed with sat. sodium chloride solution, dried, filtered and evaporated to get the product.

MS (ESI⁺): m/z=234 [M+H]⁺

Intermediate F8

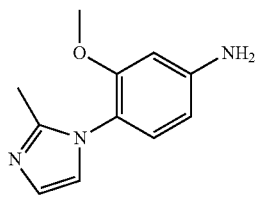

Intermediate F8-1 is hydrogenated (hydrogen atmosphere, 50 psi) in methanol (30 mL) with raney nickel at room temperature for 20 h. The reaction mixture is filtered and the filtrate is concentrated in vacuo to get the product.
MS (ESI$^+$): m/z=204 [M+H]$^+$
HPLC (Method H): Rt=0.64 min Example 1

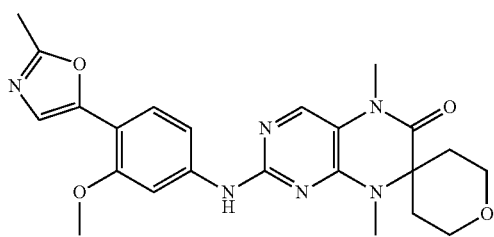 [SMILES: COc1cc(Nc2ncc3c(n2)N(C)C2(CCOCC2)C(=O)N3C)ccc1-c1cnc(C)o1]

Intermediate E1 (100 mg, 0.354 mmol) and intermediate F1 (144 mg, 0.707 mmol) are dissolved in dioxane (3 mL). The mixture is degassed with nitrogen for 5 min. Chloro(2-dicyclohexylphosphino-2',4',6'-tri-isopropyl-1,1'-biphenyl)[2-(2-aminoethyl)-phenyl]-palladium(II) (13.1 mg, 0.018 mmol) and cesium carbonate (230 mg, 0.707 mmol) are added subsequently. The reaction mixture is heated to 140° C. for 2 h using a microwave oven. DCM is added and the reaction mixture is filtered over celite and washed with DCM. The filtrate is concentrated in vacuo and the residue is purified by preparative HPLC (eluent A: water+0.1% conc. ammonia, eluent B: MeOH) to give the product as a solid.

MS (ESI$^+$): m/z=451 [M+H]$^+$

HPLC (Method A): Rt=1.07 min

In analogy to the preparation of example 1 the following compounds are obtained:

| Nr. | Structure | Educt 1 | Educt 2 | Mass signal(s) | R$_t$ |
|---|---|---|---|---|---|
| 2 | 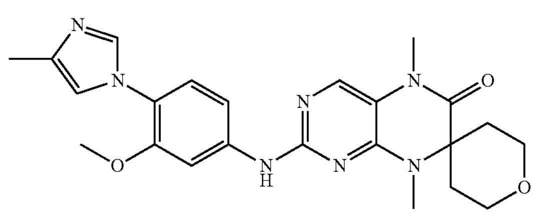 [SMILES: COc1cc(Nc2ncc3c(n2)N(C)C2(CCOCC2)C(=O)N3C)ccc1-n1cnc(C)c1] | E1 | F2 | (M + H)$^+$ = 450 | 0.82 min. (Method A) |
| 3 | 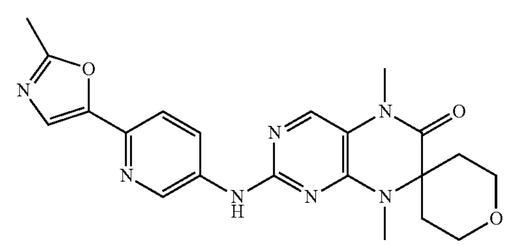 [SMILES: Cc1ncc(-c2ccc(Nc3ncc4c(n3)N(C)C3(CCOCC3)C(=O)N4C)cn2)o1] | E1 | F3 | (M + H)$^+$ = 422 | 0.94 min (Method A) |
| 4 | 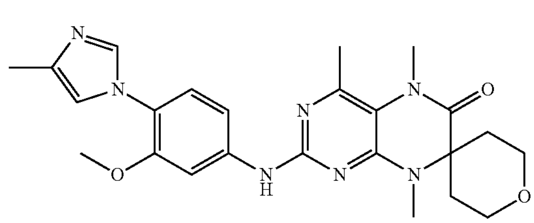 [SMILES: COc1cc(Nc2nc(C)c3c(n2)N(C)C2(CCOCC2)C(=O)N3C)ccc1-n1cnc(C)c1] | E2 | F2 | (M + H)$^+$ = 464 | 0.86 min (Method A) |

| Nr. | Structure | Educt 1 | Educt 2 | Mass signal(s) | $R_t$ |
|---|---|---|---|---|---|
| 5 | 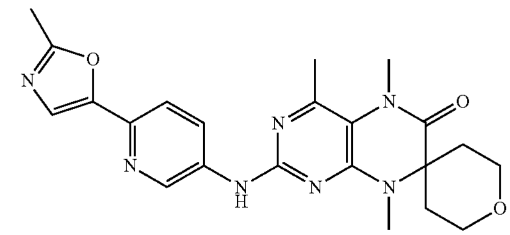 | E2 | F3 | $(M + H)^+$ = 436 | 0.94 min (Method A) |
| 6 | 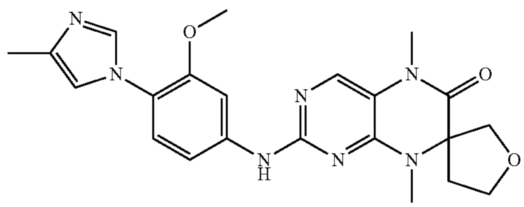 [SMILES: COc1cc(Nc2ncc3c(n2)N(C)C2(CCOC2)C(=O)N3C)ccc1-n1cnc(C)c1] | E3 | F2 | $(M + H)^+$ = 436 | 1.35 min (Method B) |
| 7 | 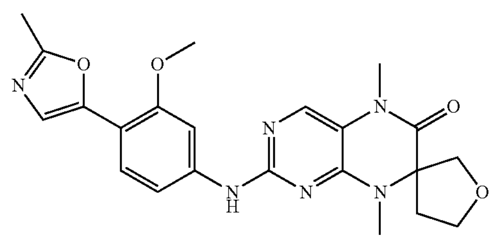 [SMILES: COc1cc(Nc2ncc3c(n2)N(C)C2(CCOC2)C(=O)N3C)ccc1-c1cnc(C)o1] | E3 | F1 | $(M + H)^+$ = 437 | 1.37 min (Method B) |
| 8 | 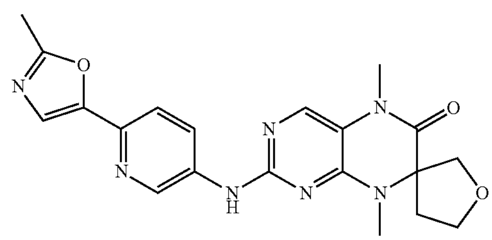 [SMILES: Cc1ncc(-c2ccc(Nc3ncc4c(n3)N(C)C3(CCOC3)C(=O)N4C)cn2)o1] | E3 | F3 | $(M + H)^+$ = 408 | 1.25 min (Method B) |
| 9 | 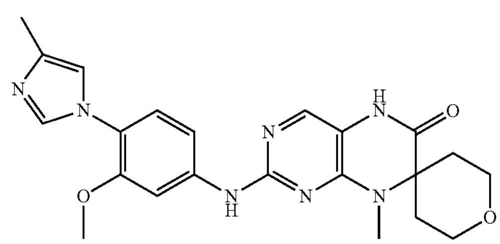 [SMILES: COc1cc(Nc2ncc3c(n2)N(C)C2(CCOCC2)C(=O)N3)ccc1-n1cnc(C)c1] | D2 | F2 | $(M + H)^+$ = 436 | 1.30 min (Method B) |
| 10 | 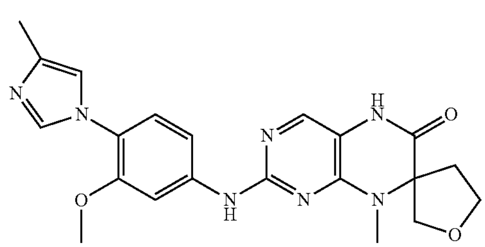 [SMILES: COc1cc(Nc2ncc3c(n2)N(C)C2(CCOC2)C(=O)N3)ccc1-n1cnc(C)c1] | D4 | F2 | $(M + H)^+$ = 422 | 1.28 min (Method B) |

-continued

| Nr. | Structure | Educt 1 | Educt 2 | Mass signal(s) | $R_f$ |
|---|---|---|---|---|---|
| 11 | 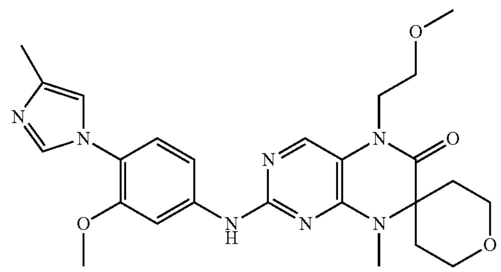 | E4 | F2 | $(M + H)^+ =$ 494 | 1.38 min (Method B) |
| 12 | 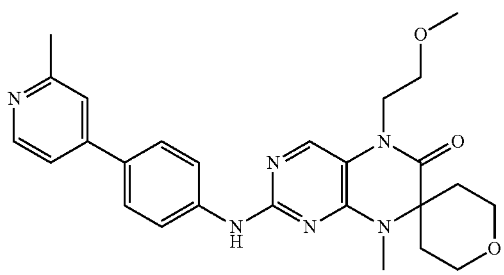 [SMILES: COCCN1C(=O)C2(CCOCC2)N(C)c2nc(Nc3ccc(-c4ccnc(C)c4)cc3)ncc21] | E4 | F4 | $(M + H)^+ =$ 475 | 1.41 min (Method B) |
| 13 | 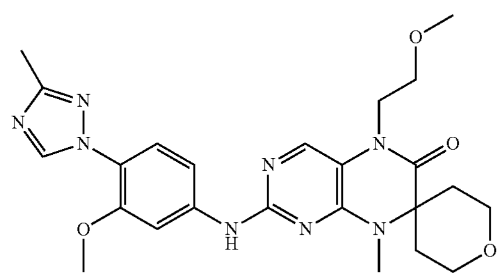 | E4 | F5 | $(M + H)^+ =$ 495 | 1.29 min (Method B) |
| 14 | 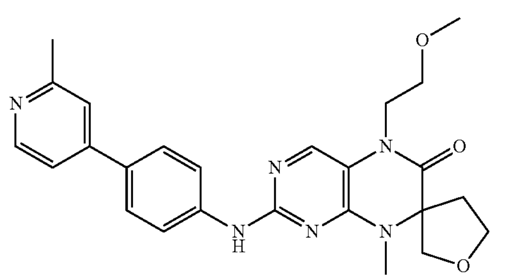 [SMILES: COCCN1C(=O)C2(CCOC2)N(C)c2nc(Nc3ccc(-c4ccnc(C)c4)cc3)ncc21] | E5 | F4 | $(M + H)^+ =$ 461 | 1.40 min (Method B) |
| 15 | 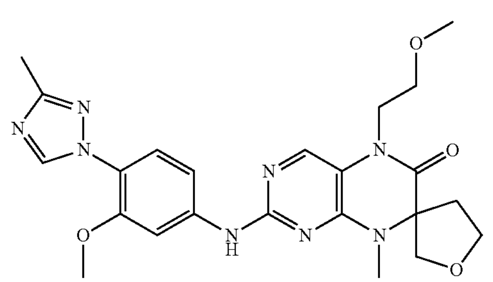 [SMILES: COCCN1C(=O)C2(CCOC2)N(C)c2nc(Nc3ccc(-n4cnc(C)n4)c(OC)c3)ncc21] | E5 | F5 | $(M + H)^+ =$ 481 | 1.27 min (Method B) |

-continued

| Nr. | Structure | Educt 1 | Educt 2 | Mass signal(s) | R_t |
|---|---|---|---|---|---|
| 16 | 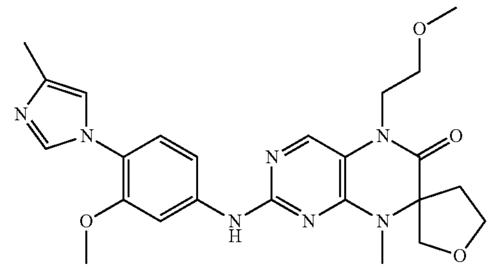 [SMILES: COCCN1C(=O)C2(CCOC2)N(C)c2nc(Nc3ccc(-n4cnc(C)c4)c(OC)c3)ncc21] | E5 | F2 | (M + H)⁺ = 480 | 1.35 min (Method B) |
| 17 | 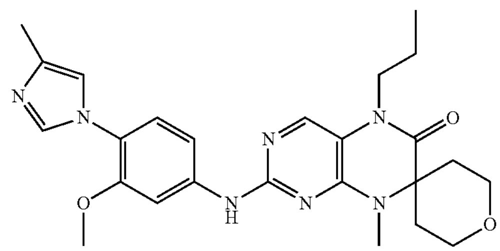 [SMILES: CCCN1C(=O)C2(CCOCC2)N(C)c2nc(Nc3ccc(-n4cnc(C)c4)c(OC)c3)ncc21] | E6 | F2 | (M + H)⁺ = 478 | 1.46 min (Method B) |
| 18 | 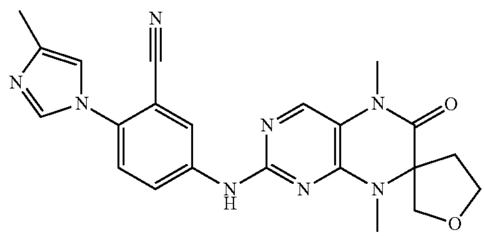 [SMILES: Cc1cn(-c2ccc(Nc3ncc4c(n3)N(C)C3(CCOC3)C(=O)N4C)cc2C#N)cn1] | E3 | F6 | (M + H)⁺ = 431 | 1.29 min (Method B) |
| 19 | 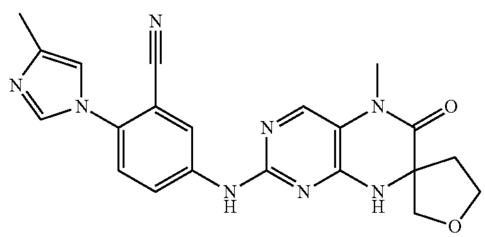 [SMILES: Cc1cn(-c2ccc(Nc3ncc4c(n3)NC3(CCOC3)C(=O)N4C)cc2C#N)cn1] | E7 | F6 | (M + H)⁺ = 417 | 1.21 min (Method B) |
| 20 | 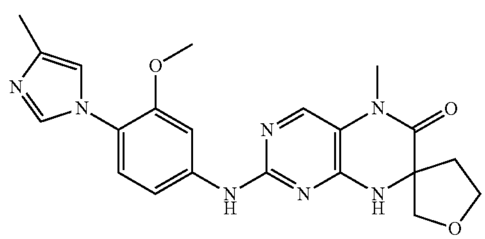 [SMILES: COc1cc(Nc2ncc3c(n2)NC2(CCOC2)C(=O)N3C)ccc1-n1cnc(C)c1] | E7 | F2 | (M + H)⁺ = 422 | 1.26 min (Method B) |
| 21 | 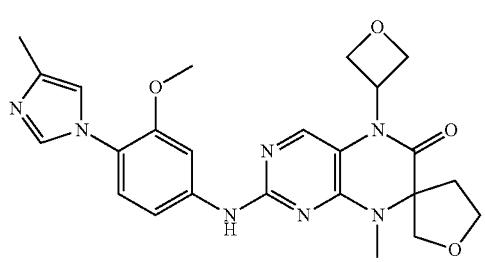 [SMILES: COc1cc(Nc2ncc3c(n2)N(C)C2(CCOC2)C(=O)N3C2COC2)ccc1-n1cnc(C)c1] | E8 | F2 | (M + H)⁺ = 478 | 1.24 min (Method B) |

-continued

| Nr. | Structure | Educt 1 | Educt 2 | Mass signal(s) | $R_t$ |
|---|---|---|---|---|---|
| 22 | 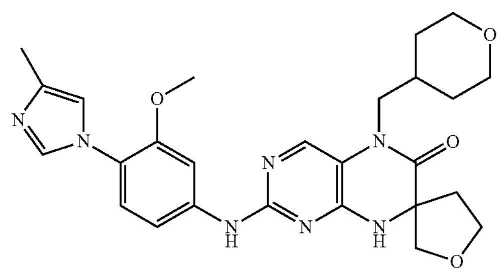 [SMILES: COc1cc(Nc2ncc3c(n2)NC2(CCOC2)C(=O)N3CC2CCOCC2)ccc1-n1cnc(C)c1] | E9 | F2 | $(M + H)^+ =$ 506 | 1.23 min (Method B) |
| 23 | 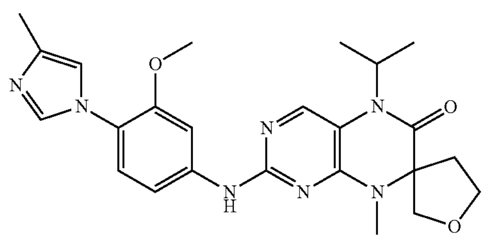 [SMILES: COc1cc(Nc2ncc3c(n2)N(C)C2(CCOC2)C(=O)N3C(C)C)ccc1-n1cnc(C)c1] | E11 | F2 | $(M + H)^+ =$ 464 | 1.35 min (Method B) |
| 24 | 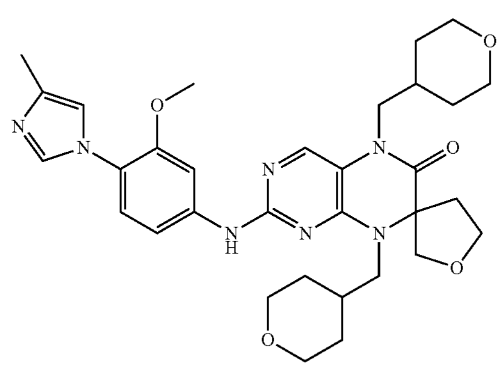 [SMILES: COc1cc(Nc2ncc3c(n2)N(CC2CCOCC2)C2(CCOC2)C(=O)N3CC2CCOCC2)ccc1-n1cnc(C)c1] | E10 | F2 | $(M + H)^+ =$ 604 | 1.30 min (Method B) |
| 25 | 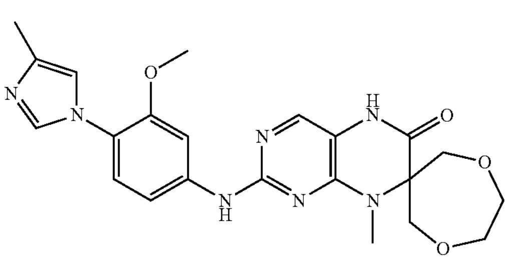 [SMILES: COc1cc(Nc2ncc3c(n2)N(C)C2(COCCOC2)C(=O)N3)ccc1-n1cnc(C)c1] | D8 | F2 | $(M + H)^+ =$ 452 | 1.19 min (Method B) |
| 26 | 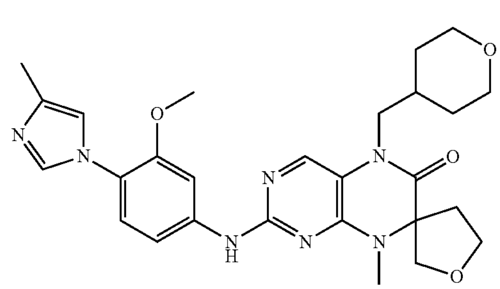 [SMILES: COc1cc(Nc2ncc3c(n2)N(C)C2(CCOC2)C(=O)N3CC2CCOCC2)ccc1-n1cnc(C)c1] | E12 | F2 | $(M + H)^+ =$ 520 | 1.24 min (Method B) |

-continued

| Nr. | Structure | Educt 1 | Educt 2 | Mass signal(s) | R_t |
|---|---|---|---|---|---|
| 27 | 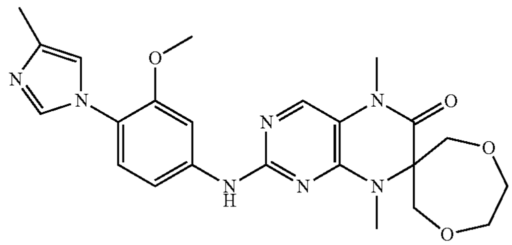 [SMILES: COc1cc(Nc2ncc3c(n2)N(C)C2(COCCOC2)C(=O)N3C)ccc1-n1cnc(C)c1] | E13 | F2 | $(M + H)^+ =$ 466 | 1.20 min (Method F) |
| 28 | 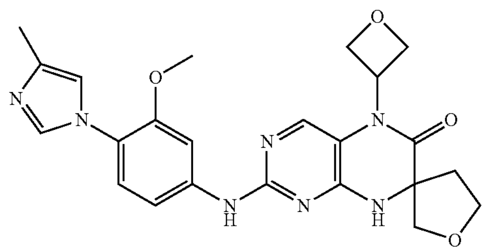 [SMILES: COc1cc(Nc2ncc3c(n2)NC2(CCOC2)C(=O)N3C2COC2)ccc1-n1cnc(C)c1] | E14 | F2 | $(M + H)^+ =$ 464 | 1.16 min (Method B) |
| 29 | 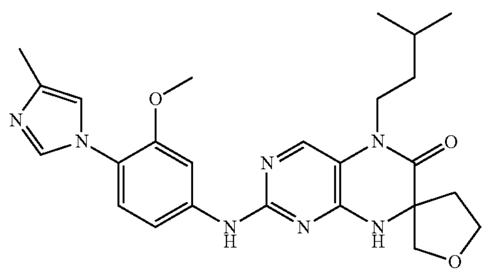 [SMILES: COc1cc(Nc2ncc3c(n2)NC2(CCOC2)C(=O)N3CCC(C)C)ccc1-n1cnc(C)c1] | E15 | F2 | $(M + H)^+ =$ 478 | 1.39 min (Method B) |
| 30 | 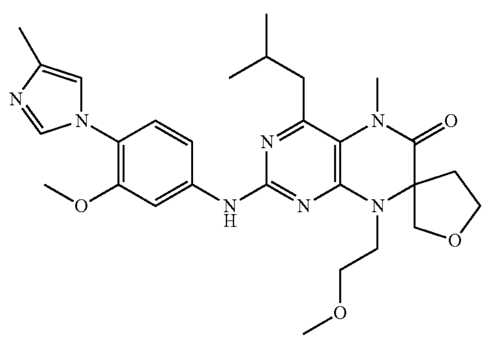 [SMILES: COCCN1c2nc(Nc3ccc(-n4cnc(C)c4)c(OC)c3)nc(CC(C)C)c2N(C)C(=O)C12CCOC2] | E17 | F2 | $(M + H)^+ =$ 536 | 1.44 min (Method B) |
| 31 | 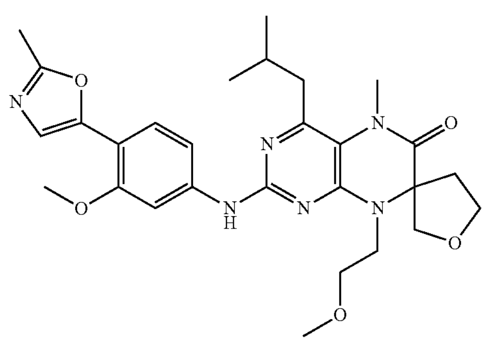 [SMILES: COCCN1c2nc(Nc3ccc(-c4cnc(C)o4)c(OC)c3)nc(CC(C)C)c2N(C)C(=O)C12CCOC2] | E17 | F1 | $(M + H)^+ =$ 537 | 1.47 min (Method B) |

-continued

| Nr. | Structure | Educt 1 | Educt 2 | Mass signal(s) | R_t |
|---|---|---|---|---|---|
| 32 | 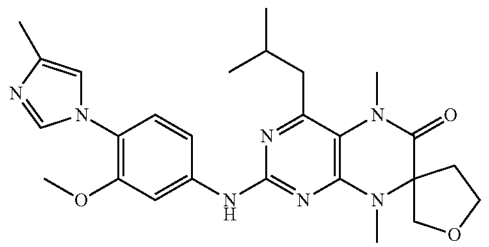 [SMILES: COc1cc(Nc2nc(CC(C)C)c3c(n2)N(C)C2(CCOC2)C(=O)N3C)ccc1-n1cnc(C)c1] | E18 | F2 | (M + H)⁺ = 492 | 1.43 min (Method B) |
| 33 | 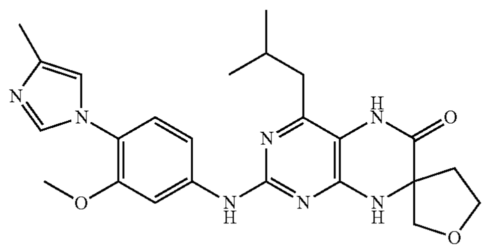 [SMILES: COc1cc(Nc2nc(CC(C)C)c3c(n2)NC2(CCOC2)C(=O)N3)ccc1-n1cnc(C)c1] | D7 | F2 | (M + H)⁺ = 464 | 1.40 min (Method B) |
| 34 | 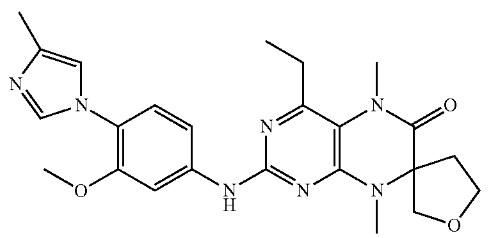 [SMILES: CCc1nc(Nc2ccc(-n3cnc(C)c3)c(OC)c2)nc2c1N(C)C(=O)C1(CCOC1)N2C] | E19 | F2 | (M + H)⁺ = 464 | 1.35 min (Method B) |
| 35 | 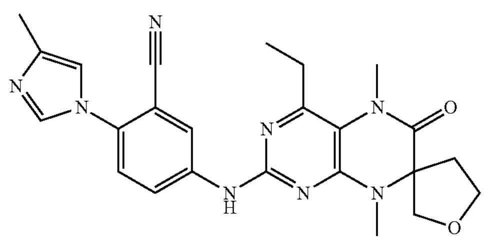 [SMILES: CCc1nc(Nc2ccc(-n3cnc(C)c3)c(C#N)c2)nc2c1N(C)C(=O)C1(CCOC1)N2C] | E19 | F6 | (M + H)⁺ = 459 | 1.30 min (Method B) |
| 36 | 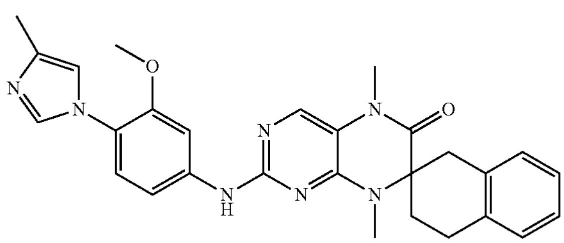 [SMILES: COc1cc(Nc2ncc3c(n2)N(C)C2(CCc4ccccc4C2)C(=O)N3C)ccc1-n1cnc(C)c1] | E20 | F2 | (M + H)⁺ = 496 | 1.12 min (Method A) |
| 37 | 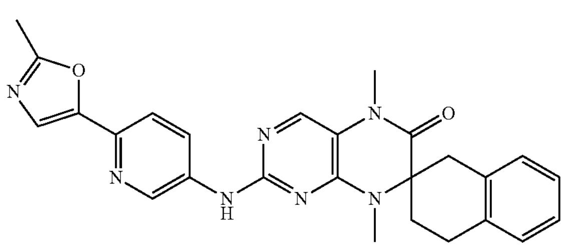 [SMILES: Cc1ncc(-c2ccc(Nc3ncc4c(n3)N(C)C3(CCc5ccccc5C3)C(=O)N4C)cn2)o1] | E20 | F3 | (M + H)⁺ = 468 | 1.25 min (Method A) |

-continued

| Nr. | Structure | Educt 1 | Educt 2 | Mass signal(s) | R_t |
|---|---|---|---|---|---|
| 37a | 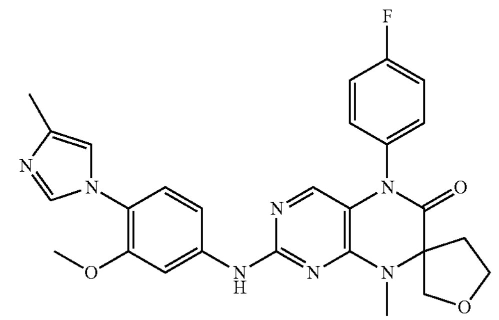 [SMILES: COc1cc(Nc2ncc3c(n2)N(C)C2(CCOC2)C(=O)N3c2ccc(F)cc2)ccc1-n1cnc(C)c1] | E21 | F2 | (M + H)⁺ = 516 | 1.28 min (Method F) |
| 37b | 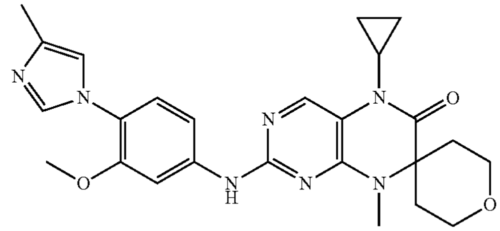 [SMILES: COc1cc(Nc2ncc3c(n2)N(C)C2(CCOCC2)C(=O)N3C2CC2)ccc1-n1cnc(C)c1] | E20a | F2 | (M + H)⁺ = 476 | 0.98 min (Method H) |
| 37c | 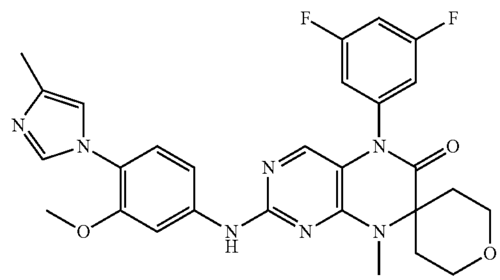 [SMILES: COc1cc(Nc2ncc3c(n2)N(C)C2(CCOCC2)C(=O)N3c2cc(F)cc(F)c2)ccc1-n1cnc(C)c1] | E20b | F2 | (M + H)⁺ = 548 | 0.43 min (Method I) |
| 37d | 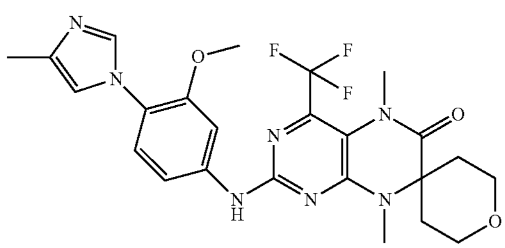 [SMILES: COc1cc(Nc2nc3c(c(C(F)(F)F)n2)N(C)C(=O)C2(CCOCC2)N3C)ccc1-n1cnc(C)c1] | E1b | F2 | (M + H)⁺ = 518 | 0.50 min (Method J) |
| 37e | 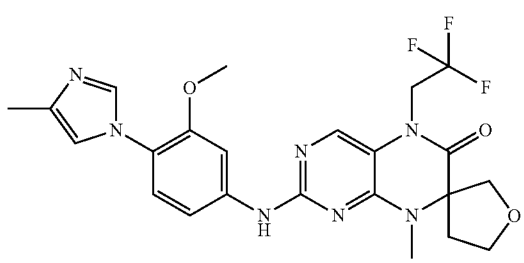 [SMILES: COc1cc(Nc2ncc3c(n2)N(C)C2(CCOC2)C(=O)N3CC(F)(F)F)ccc1-n1cnc(C)c1] | E24 | F2 | (M + H)⁺ = 504 | 0.39 min (Method I) |

-continued

| Nr. | Structure | Educt 1 | Educt 2 | Mass signal(s) | $R_t$ |
|---|---|---|---|---|---|
| 37f | 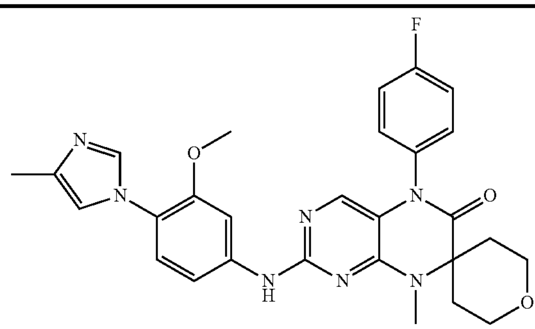 | E24b | F2 | $(M + H)^+ =$ 530 | 0.42 min (Method I) |
| 37g | 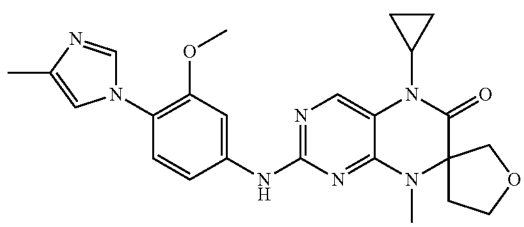 [SMILES: COc1cc(Nc2ncc3c(n2)N(C)C2(CCOC2)C(=O)N3C2CC2)ccc1-n1cnc(C)c1] | E25c | F2 | $(M + H)^+ =$ 462 | 0.79 min (Method O) |
| 37h | 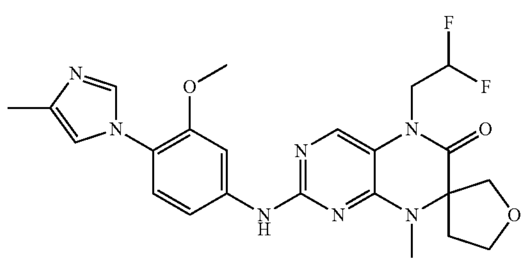 [SMILES: COc1cc(Nc2ncc3c(n2)N(C)C2(CCOC2)C(=O)N3CC(F)F)ccc1-n1cnc(C)c1] | E25d | F2 | $(M + H)^+ =$ 486 | 0.99 min (Method H) |
| 37i | 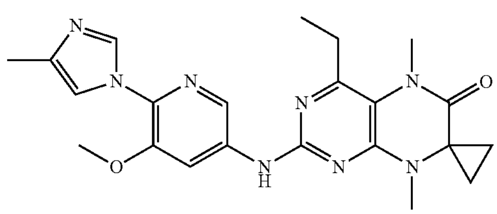 [SMILES: CCc1nc(Nc2cnc(-n3cnc(C)c3)c(OC)c2)nc2c1N(C)C(=O)C1(CC1)N2C] | E1c | F7 | $(M + H)^+ =$ 435 | 0.78 min (Method L) |
| 37j | 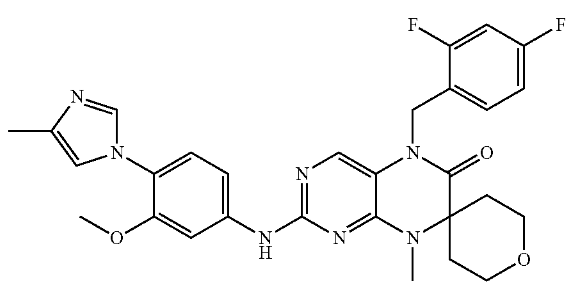 [SMILES: COc1cc(Nc2ncc3c(n2)N(C)C2(CCOCC2)C(=O)N3Cc2ccc(F)cc2F)ccc1-n1cnc(C)c1] | E25 | F2 | $(M + H)^+ =$ 562 | 0.49 min (Method P) |
| 37k | 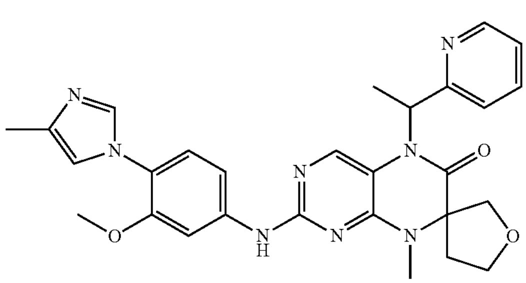 [SMILES: COc1cc(Nc2ncc3c(n2)N(C)C2(CCOC2)C(=O)N3C(C)c2ccccn2)ccc1-n1cnc(C)c1] | E25b | F2 | $(M + H)^+ =$ 527 | 1.02 min (Method H) |

Example 38

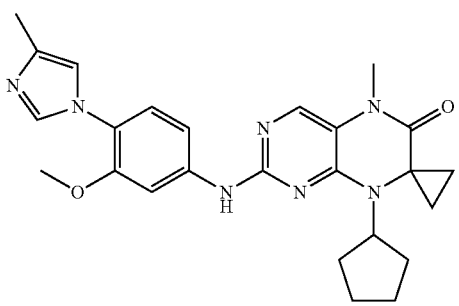 [SMILES: COc1cc(Nc2ncc3c(n2)N(C2CCCC2)C2(CC2)C(=O)N3C)ccc1-n1cnc(C)c1]

2'-Chloro-8'-cyclopentyl-5'-methyl-5'H-spiro[cyclopropane-1,7'-pteridin]-6'(8'H)-one (100 mg, 0.342 mmol, prepared according to WO 2004-076454) and intermediate F2 (76.4 mg, 0.376 mmol) are mixed with 4-methyl-2-pentanol (1 mL) and stirred for 10 min. at 55° C. p-Toluenesulfonic acid (12% in acetic acid, 1.15 mL, 0.854 mmol) is added and the reaction mixture is stirred for 48 h at 70° C. The mixture is concentrated in vacuo and the residue is purified by preparative HPLC (eluent A: water+0.1% conc. ammonia, eluent B: MeOH) to give the product as a solid.

MS (ESI⁺): m/z=460 [M+H]⁺

HPLC (Method C): Rt=0.60 min

Example 39

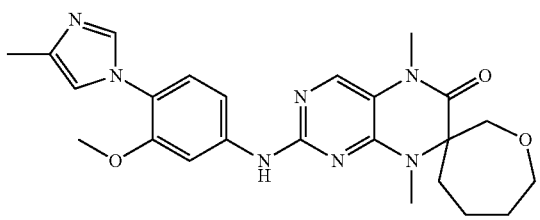 [SMILES: COc1cc(Nc2ncc3c(n2)N(C)C2(CCCCOC2)C(=O)N3C)ccc1-n1cnc(C)c1]

Intermediate E20c (40.0 mg, 0.135 mmol) and intermediate F2 (35.6 mg, 0.175 mmol) are dissolved in dioxane (4.5 mL). The mixture is degassed with nitrogen for 5 min. Dicyclohexyl-(2',4',6'-triisopropyl-biphenyl-2-yl)-phosphane (6.42 mg, 0.013 mmol), palladium(II)acetate (3.03 mg, 0.013 mmol) and cesium carbonate (184 mg, 0.566 mmol) are added subsequently. The reaction mixture is heated to 140° C. for 45 min using a microwave oven. DCM is added and the reaction mixture is filtered over celite and washed with DCM. The filtrate is concentrated in vacuo and the residue is purified by preparative HPLC (eluent A: water+0.1% conc. ammonia, eluent B: MeOH) to give the product as a solid.

MS (ESI⁺): m/z=464 [M+H]⁺

HPLC (Method H): Rt=1.10 min

In analogy to the preparation of example 39 the following compounds are obtained:

| Nr. | Structure | Educt 1 | Educt 2 | Mass signal(s) | $R_t$ |
|---|---|---|---|---|---|
| 40 | 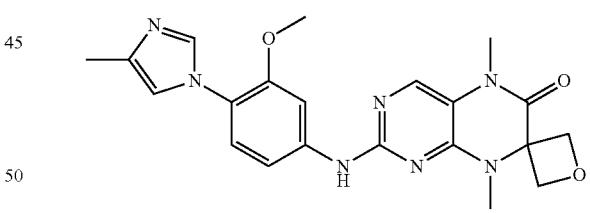 | E28 | F1 | (M + H)⁺ = 495 | 1.09 min. (Method H) |

Example 41

Intermediate E20f (24.0 mg, 0.094 mmol) and intermediate F2 (24.9 mg, 0.123 mmol) are dissolved in dioxane (4.5 mL). The mixture is degassed with nitrogen for 5 min. XPhos (4.49 mg, 0.009 mmol), palladium(II)acetate (2.12 mg, 0.009 mmol) and cesium carbonate (35.5 mg, 0.283 mmol) are added subsequently. The reaction mixture is heated to 140° C. for 45 min using a microwave oven. The reaction mixture is filtered over celite, washed with DCM and concentrated in vacuo. The residue is purified by preparative HPLC (eluent A: water+0.1% conc. ammonia, eluent B: MeOH) to give the product as a solid.

MS (ESI⁺): m/z=422 [M+H]⁺

HPLC (Method H): Rt=0.89 min

In analogy to the preparation of example 42 the following compounds are obtained:

| Nr. | Structure | Educt 1 | Educt 2 | Mass signal(s) | $R_t$ |
|---|---|---|---|---|---|
| 42 | 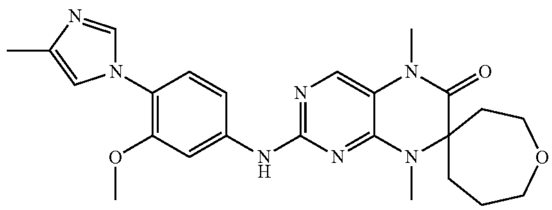 [SMILES: COc1cc(Nc2ncc3c(n2)N(C)C2(CCCOCC2)C(=O)N3C)ccc1-n1cnc(C)c1] | E20g | F2 | $(M + H)^+ =$ 464 | 0.96 min. (Method H) |
| 43 | 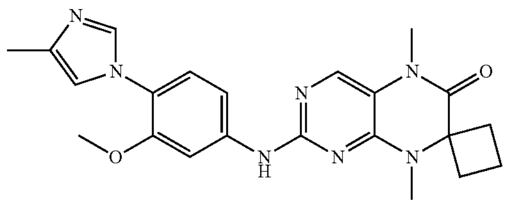 [SMILES: COc1cc(Nc2ncc3c(n2)N(C)C2(CCC2)C(=O)N3C)ccc1-n1cnc(C)c1] | E1e | F2 | $(M + H)^+ =$ 420 | 1.03 min. (Method H) |
| 44 | 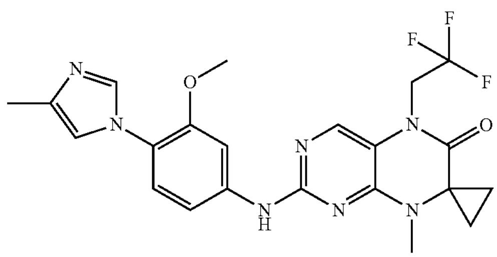 [SMILES: COc1cc(Nc2ncc3c(n2)N(C)C2(CC2)C(=O)N3CC(F)(F)F)ccc1-n1cnc(C)c1] | E25e | F2 | $(M + H)^+ =$ 474 | 1.09 min. (Method H) |
| 45 | 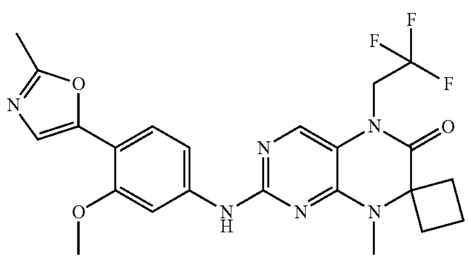 [SMILES: COc1cc(Nc2ncc3c(n2)N(C)C2(CCC2)C(=O)N3CC(F)(F)F)ccc1-c1cnc(C)o1] | E25f | F1 | $(M + H)^+ =$ 489 | 1.22 min. (Method H) |
| 46 | 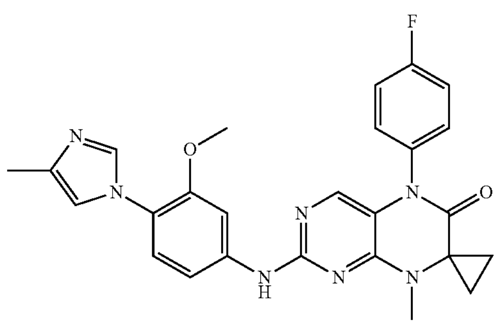 [SMILES: COc1cc(Nc2ncc3c(n2)N(C)C2(CC2)C(=O)N3c2ccc(F)cc2)ccc1-n1cnc(C)c1] | E23d | F2 | $(M + H)^+ =$ 486 | 1.10 min. (Method H) |
| 47 | 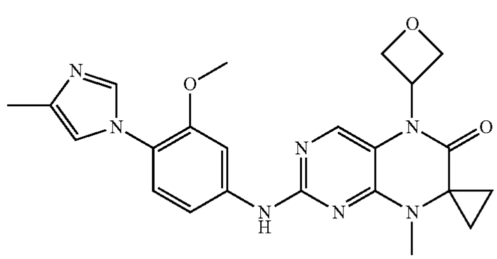 [SMILES: COc1cc(Nc2ncc3c(n2)N(C)C2(CC2)C(=O)N3C2COC2)ccc1-n1cnc(C)c1] | E25g | F2 | $(M + H)^+ =$ 448 | 0.92 min. (Method H) |

| Nr. | Structure | Educt 1 | Educt 2 | Mass signal(s) | $R_t$ |
|---|---|---|---|---|---|
| 48 | 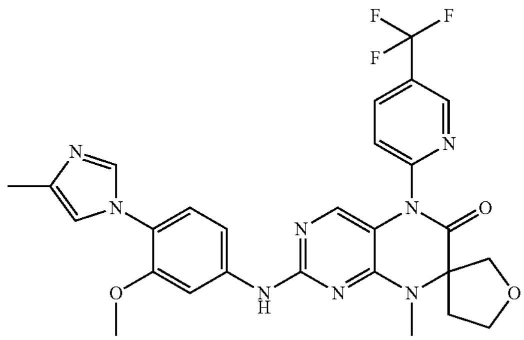 [SMILES: COc1cc(Nc2ncc3c(n2)N(C)C2(CCOC2)C(=O)N3c2ccc(C(F)(F)F)cn2)ccc1-n1cnc(C)c1] | E29 | F2 | $(M + H)^+ =$ 567 | 1.09 min. (Method H) |
| 49 | 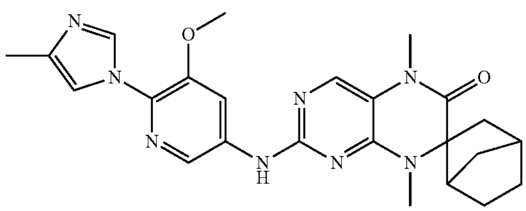 [SMILES: COc1cc(Nc2ncc3c(n2)N(C)C2(CC4CCC2C4)C(=O)N3C)cnc1-n1cnc(C)c1] | E20i | F7 | $(M + H)^+ =$ 461 | 1.09 min. (Method H) |
| 50 | 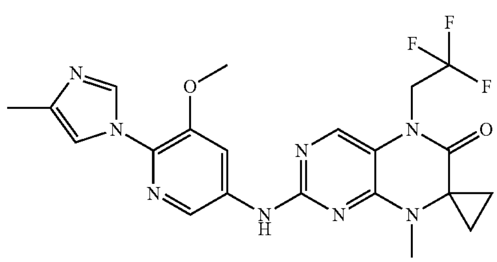 | E25e | F7 | $(M + H)^+ =$ 475 | 1.06 min. (Method H) |
| 51 | 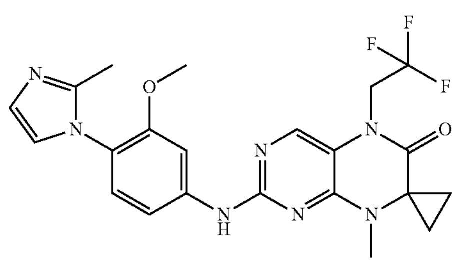 [SMILES: COc1cc(Nc2ncc3c(n2)N(C)C2(CC2)C(=O)N3CC(F)(F)F)ccc1-n1ccnc1C] | E25e | F8 | $(M + H)^+ =$ 474 | 1.06 min. (Method H) |
| 52 | 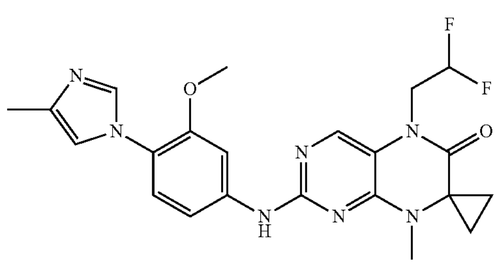 [SMILES: COc1cc(Nc2ncc3c(n2)N(C)C2(CC2)C(=O)N3CC(F)F)ccc1-n1cnc(C)c1] | E25h | F2 | $(M + H)^+ =$ 456 | 1.03 min. (Method H) |
| 53 | 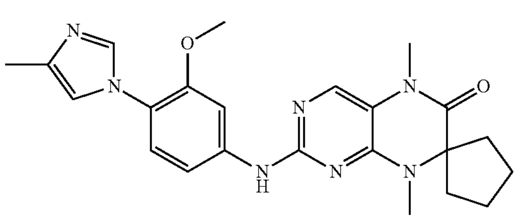 [SMILES: COc1cc(Nc2ncc3c(n2)N(C)C2(CCCC2)C(=O)N3C)ccc1-n1cnc(C)c1] | E20j | F2 | $(M + H)^+ =$ 434 | 1.08 min. (Method H) |

| Nr. | Structure | Educt 1 | Educt 2 | Mass signal(s) | $R_t$ |
|---|---|---|---|---|---|
| 54 | 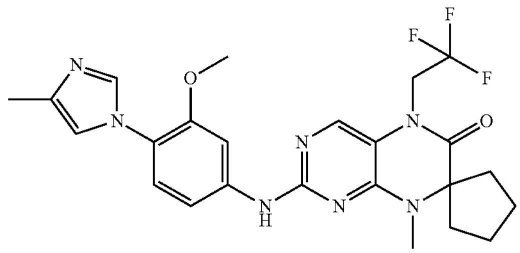 [SMILES: COc1cc(Nc2ncc3c(n2)N(C)C2(CCCC2)C(=O)N3CC(F)(F)F)ccc1-n1cnc(C)c1] | E24-1f | F2 | $(M + H)^+ =$ 502 | 1.21 min. (Method H) |
| 55 | 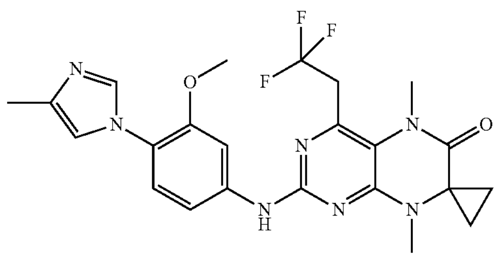 [SMILES: COc1cc(Nc2nc(CC(F)(F)F)c3c(n2)N(C)C2(CC2)C(=O)N3C)ccc1-n1cnc(C)c1] | E1f | F2 | $(M + H)^+ =$ 488 | 0.45 min. (Method J) |

The invention claimed is:

1. A compound of the formula I

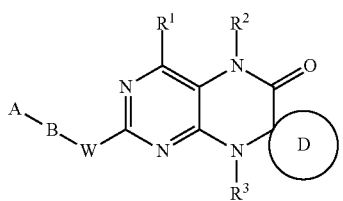

wherein

A is selected from the group $A^a$ consisting of
a heteroaryl group with 5 or 6 ring atoms containing one to three heteroatoms independently selected from N, O, S,
wherein above mentioned heteroaryl groups may optionally be substituted with 1 or 2 substituents independently selected from the group consisting of halogen, cyano, $C_{1-6}$-alkyl-, HO—$C_{1-6}$-alkyl- which is optionally fluorinated with 1 to 13 fluorine atoms, $C_{3-6}$-cycloalkyl-, $C_{1-4}$-alkyl-O—$C_{1-3}$-alkyl-, $C_{1-4}$-alkyl-O— which is optionally fluorinated with 1 to 9 fluorine atoms and $(C_{1-4}$-alkyl$)_3$Si—;

B is selected from the group $B^a$ consisting of

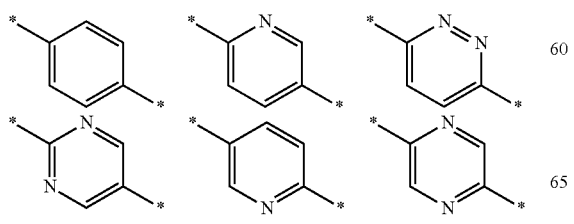

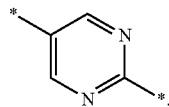

wherein above mentioned phenyl-, pyridinyl-, pyrimidinyl-, pyridazinyl and pyrazinyl groups may optionally be substituted with 1 or 2 substituents independently selected from the group consisting of HO—, halogen, cyano, $C_{1-6}$-alkyl- which is optionally fluorinated with 1 to 13 fluorine atoms, $C_{3-6}$-cycloalkyl-O— and $C_{1-6}$-alkyl-O— which is optionally fluorinated with 1 to 13 fluorine atoms;

D is selected from the group $D^a$ consisting of
a 4- to 12-membered mono-, bicyclic or bridged heterocyclyl group, or a 3- to 12-membered mono- or bicyclic carbocyclyl group,
wherein above mentioned group $D^a$ may optionally be substituted with 1 to 4 substituents independently selected from the group consisting of halogen, cyano, $C_{1-6}$-alkyl- which is optionally fluorinated with 1 to 13 fluorine atoms, $C_{3-6}$-cycloalkyl-, heterocyclyl, aryl, aryl-$C_{1-3}$-alkyl-, heteroaryl, heteroaryl-$C_{1-3}$-alkyl-, HC(O)—, $C_{1-6}$-alkyl-C(O)—, $C_{3-6}$-cycloalkyl-C(O)—, aryl-C(O)—, $C_{1-4}$-alkyl-O—C(O)—, $(C_{1-4}$-alkyl$)_2$N—C(O)—, HO—, oxo, $C_{1-6}$-alkyl-O— which is optionally fluorinated with 1 to 13 fluorine atoms, $C_{3-6}$-cycloalkyl-O—, heterocyclyl-O—, aryl-O—, heteroaryl-O—, $H_2N$—, $(C_{1-4}$-alkyl$)_2N$—, azetidinyl, pyrrolidinyl and $(C_{1-4}$-alkyl$)(C_{1-3}$-alkyl-C(O))N—,
wherein above mentioned aryl-C(O)—, aryl-O—, aryl, aryl-$C_{1-3}$-alkyl-, heteroaryl, heteroaryl-$C_{1-3}$-alkyl- and heteroaryl-O— groups may optionally be substituted with 1 to 3 substituents independently selected from the group consisting of HO—, $C_{1-4}$-alkyl-O—, $F_3CO$—, $F_3C$—, $F_2HCO$—, $FH_2CO$—, heterocyclyl-O—, cyano, halogen, $F_5S$—, $(C_{1-4}$-alkyl$)_3Si$—, nitro, $H_2N$—, $(C_{1-4}$-alkyl$)_2N$—, $(H_2N)$—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl- which is optionally fluorinated with 1 to 13 fluorine atoms;

W is selected from the group $W^a$ consisting of —$(R^7)N$— and —O—;

$R^1$ is selected from the group $R^{1a}$ consisting of
H, $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl-, $R^4R^5N$—$C_{1-3}$-alkyl-, $R^4O$—, $R^4S(O)_m$— with m=0, 1, 2,
  wherein above mentioned $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl- and $R^4R^5N$—$C_{1-3}$-alkyl- groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $F_5S$—, $(C_{1-4}$-alkyl$)_3Si$—, nitro, $H_2N$—, $(C_{1-4}$-alkyl$)_2N$—, $(H_2N)$—C(O)—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl-, and
  wherein above mentioned $C_{1-4}$-alkyl-O—, $C_{3-6}$-cycloalkyl-O—, heterocyclyl-O—, $(C_{1-4}$-alkyl$)_2$ N—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2$ N—C(O)—, $C_{1-4}$-alkyl-O—$C_{1-4}$-alkyl- and $C_{1-6}$-alkyl- groups may optionally be substituted with 1 to 13 fluorine atoms;

$R^2$ is selected from the group $R^{2a}$ consisting of
H, $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl-, $R^4R^5N$—, $R^4R^5N$—$C_{1-3}$-alkyl-, $R^4R^5N$—C(O)— and $R^4O$—,
  wherein above mentioned $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl and heteroaryl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $F_5S$—, $(C_{1-4}$-alkyl$)_3Si$—, nitro, $H_2N$—, $(C_{1-4}$-alkyl$)_2N$—, $(H_2N)$—C(O)—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2$ N—C(O)—, $C_{1-4}$-alkyl-O—$C_{1-4}$-alkyl-, $C_{3-5}$-cycloalkyl- and $C_{1-6}$-alkyl-, and
  wherein above mentioned $C_{1-4}$-alkyl-O—, $C_{3-6}$-cycloalkyl-O—, heterocyclyl-O—, $(C_{1-4}$-alkyl$)_2$ N—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2$ N—C(O)—, $C_{1-4}$-alkyl-O—$C_{1-4}$-alkyl-, $C_{3-5}$-cycloalkyl- and $C_{1-6}$-alkyl- may optionally be substituted with 1 to 13 fluorine atoms;

$R^3$ is selected from the group $R^{3a}$ consisting of
H, $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl-, $R^4R^5N$—, $R^4R^5N$—$C_{1-3}$-alkyl-, and $R^4O$—,
  wherein above mentioned $C_{1-8}$-alkyl-, $C_{2-8}$-alkenyl-, $C_{2-8}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl and heteroaryl-$C_{1-3}$-alkyl-groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $F_5S$—, $(C_{1-4}$-alkyl$)_3$ Si—, nitro, $H_2N$—, $(C_{1-4}$-alkyl$)_2N$—, $(H_2N)$—C(O)—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2$ N—C(O)—, $C_{1-4}$-alkyl-O—$C_{1-4}$-alkyl- and $C_{1-6}$-alkyl-, and
  wherein above mentioned $C_{1-4}$-alkyl-O—, $C_{3-6}$-cycloalkyl-O—, heterocyclyl-O—, $(C_{1-4}$-alkyl$)_2$ N—, $(C_{1-4}$-alkyl)-C(O)—, $(C_{1-4}$-alkyl)-O—C(O)—, $(C_{1-4}$-alkyl)-HN—C(O)—, $(C_{1-4}$-alkyl$)_2$ N—C(O)—, $C_{1-4}$-alkyl-O—$C_{1-4}$-alkyl- and $C_{1-6}$-alkyl- groups may optionally be substituted with 1 to 13 fluorine atoms;

$R^4$, $R^5$ are selected independently of each other from the group $R^{4a}/R^{5a}$ consisting of
H, $C_{1-6}$-alkyl-, carbocyclyl, carbocyclyl-$C_{1-3}$-alkyl-, carbocyclyl-O—$C_{2-4}$-alkyl-, heterocyclyl, heterocyclyl-$C_{1-6}$-alkyl-, heterocyclyl-O—$C_{2-4}$-alkyl-, aryl, aryl-$C_{1-3}$-alkyl-, aryl-O—$C_{2-3}$-alkyl-, heteroaryl, heteroaryl-$C_{1-3}$-alkyl- and heteroaryl-O—$C_{2-3}$-alkyl-,
  wherein above mentioned $C_{1-6}$-alkyl-, carbocyclyl, carbocyclyl-$C_{1-3}$-alkyl-, carbocyclyl-O—$C_{2-4}$-alkyl-, heterocyclyl, heterocyclyl-$C_{1-6}$-alkyl- or heterocyclyl-O—$C_{2-4}$-alkyl- groups may optionally be substituted with 1 to 3 substituents independently selected from the group consisting of halogen, cyano, HO—, oxo, $C_{1-4}$-alkyl-O— which is optionally fluorinated with 1 to 9 fluorine atoms, $C_{1-4}$-alkyl-O—C(O)—, HO—$C_{1-4}$-alkyl-, $C_{1-4}$-alkyl-O—$C_{1-4}$-alkyl-, heterocyclyl, $(C_{1-4}$-alkyl$)_2$ N—, $(C_{1-3}$-alkyl$)_2N$—C(O)—, and $C_{1-6}$-alkyl- which is optionally fluorinated with 1 to 13 fluorine atoms,
  wherein above mentioned aryl-, aryl-$C_{1-3}$-alkyl-, aryl-O—$C_{2-3}$-alkyl-, heteroaryl-, heteroaryl-$C_{1-3}$-alkyl- and heteroaryl-O—$C_{2-3}$-alkyl- groups may optionally be substituted with 1 to 3 substituents independently selected from the group consisting of HO—, $C_{1-4}$-alkyl-O—, $F_3CO$—, $F_2HCO$—, $FH_2CO$—, heterocyclyl-O—, cyano, halogen, $F_5S$—, $(C_{1-4}$-alkyl$)_3Si$—, nitro, $(R^6)_2N$—, $(H_2N)$—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl- which is optionally fluorinated with 1 to 13 fluorine atoms, or $R^{4a}$ and $R^{5a}$ form together with the nitrogen atom to which they are attached a 4-12-membered mono-, bicyclic or bridged ring system optionally containing one or two double bonds and/or one aromatic ring and optionally containing one or two additional heteroatoms selected from the group consisting of —O—, —S—, —S(O)—, —S(O)$_2$—, —N($R^6$)—,
  wherein 2 geminal hydrogen atoms of the 4-12-membered mono- or bicyclic ring system may be replaced by a —$(CH_2)_{1-5}$— group and
  wherein one —$(CH_2)$— group of the —$(CH_2)_{1-5}$— group may be replaced by —O— or —N($R^6$)— and wherein above mentioned 4-12-membered mono-, bicyclic or bridged ring system may optionally be substituted with 1 or 2 substituents independently selected from the group consisting of halogen, cyano, aryl, heteroaryl, aryl-$C_{1-3}$-alkyl-, $C_{1-6}$-alkyl- which is optionally fluorinated with 1 to 13 fluorine atoms, heterocyclyl, HO—, oxo, $C_{1-6}$-alkyl-O—, $C_{3-6}$-cycloalkyl-O—, $C_{1-4}$-alkyl-O—C(O)—, HO—$C_{1-4}$-alkyl-, $C_{1-4}$-alkyl-O—$C_{1-4}$-alkyl-, $C_{3-6}$-cycloalkyl-O—$C_{1-4}$-alkyl-, heterocyclyl-O—, heterocyclyl-O—$C_{1-4}$-alkyl-, aryl-O—, heteroaryl-O— and $(R^6)_2N$—, wherein the directly above mentioned aryl, aryl-$C_{1-3}$-alkyl-, aryl-O—, heteroaryl-O—, and heteroaryl groups may optionally be substituted with 1 to 3 substituents independently selected from the group consisting of HO—, $C_{1-4}$-alkyl-O—, $F_3CO$—, $F_2HCO$—, $FH_2CO$—, heterocyclyl-O—, cyano, halogen, $F_5S$—, $(C_{1-4}$-alkyl$)_3Si$—, nitro, amino, $(C_{1-4}$-alkyl$)_2N$—, $(H_2N)$—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl- which is optionally fluorinated with 1 to 13 fluorine atoms;

$R^6$ is selected independently of each other from the group $R^{6a}$ consisting of H, $C_{1-6}$-alkyl-, $C_{3-6}$-cycloalkyl, heterocyclyl, heteroaryl, HC(O)—, $C_{1-6}$-alkyl-C(O)—, $C_{3-6}$-cycloalkyl-C(O)—, aryl-C(O)—, $C_{1-4}$-alkyl-O—C(O)— and $(C_{1-4}$-alkyl$)_2N$—C(O)—, wherein above mentioned $C_{1-6}$-alkyl-, $C_{3-6}$-cycloalkyl-, $C_{1-6}$-alkyl-C(O)— and $C_{3-6}$-cycloalkyl-C(O)— groups may optionally be substituted with 1-13 fluorine atoms, wherein the above mentioned aryl-C(O)— and heteroaryl group may optionally be substituted with 1 to 3 substituents independently selected from the group consisting of HO—, $C_{1-4}$-alkyl-O—, $F_3CO$—, $F_2HCO$—, $FH_2CO$—, heterocyclyl-O—, cyano, halogen, $F_5S$—, $(C_{1-4}$-alkyl$)_3Si$—, nitro, amino, $(C_{1-4}$-alkyl$)_2N$—, $(H_2N)$—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl- which is optionally fluorinated with 1 to 13 fluorine atoms;

$R^7$ is selected from the group $R^{7a}$ consisting of

H and $C_{1-5}$-alkyl- which is optionally fluorinated with 1 to 13 fluorine atoms, or a salt thereof.

2. A compound according to claim 1, wherein

A is selected from the group $A^b$ consisting of

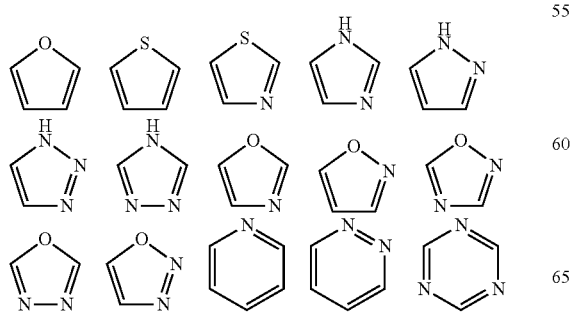

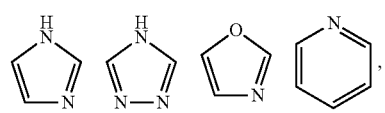

wherein above mentioned groups may optionally be substituted with 1 or 2 substituents independently selected from the group consisting of halogen, cyano, and $C_{1-6}$-alkyl- which is optionally fluorinated with 1 to 13 fluorine atoms.

3. A compound according to claim 1, wherein

A is selected from the group $A^e$ consisting of

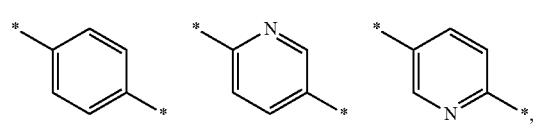

wherein above mentioned groups may optionally be substituted with 1 or 2 substituents independently selected from the group consisting of halogen and $C_{1-3}$-alkyl- which is optionally fluorinated with 1 to 7 fluorine atoms.

4. A compound according to claim 1, wherein

B is selected from the group $B^b$ consisting of wherein above mentioned phenyl- and pyridinyl-groups may optionally be substituted with 1 or 2 substituents independently selected from the group consisting of HO—, halogen, cyano, $C_{1-6}$-alkyl- which is optionally fluorinated with 1 to 13 fluorine atoms, $C_{3-6}$-cycloalkyl-O— and $C_{1-6}$-alkyl-O— which is optionally fluorinated with 1 to 13 fluorine atoms.

5. A compound according to claim 1, wherein

D is selected from the group $D^b$ consisting of

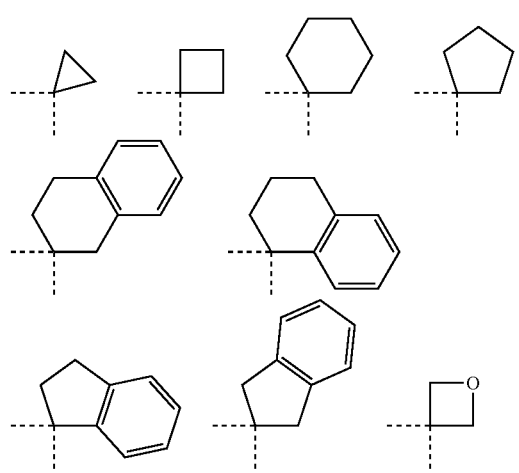

-continued

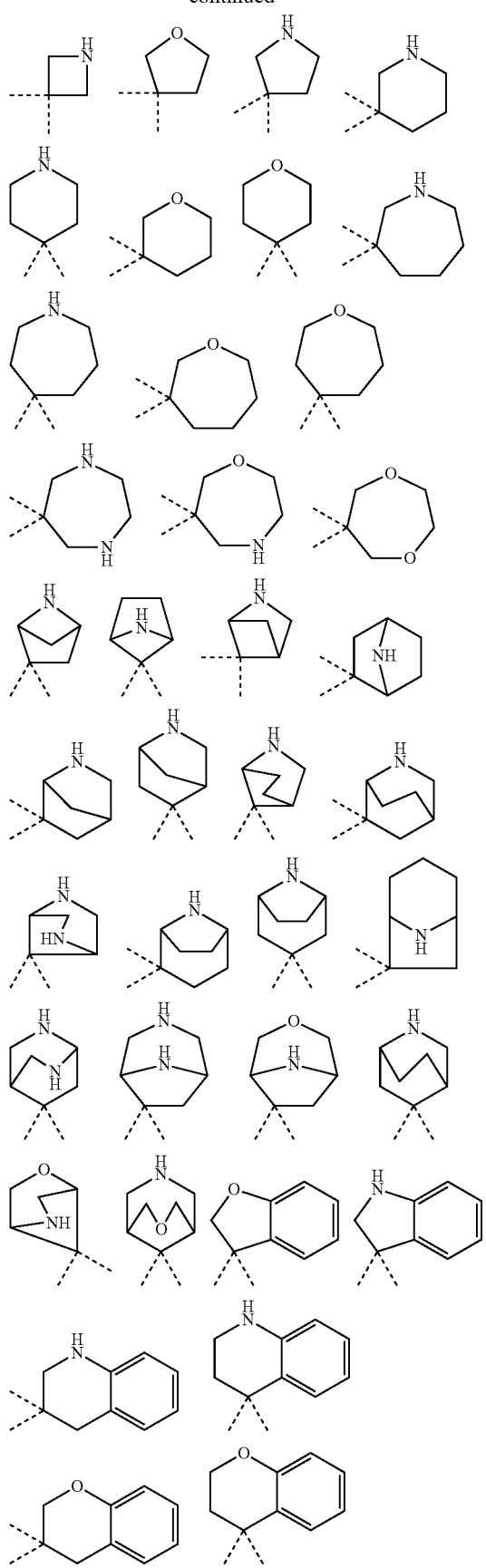
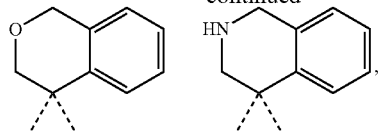

wherein above mentioned ring system $D^b$ may optionally be substituted with 1 to 4 substituents independently selected from the group consisting of halogen, cyano, $C_{1-6}$-alkyl- which is optionally fluorinated with 1 to 13 fluorine atoms, $C_{3-6}$-cycloalkyl-, heterocyclyl, aryl, aryl-$C_{1-3}$-alkyl-, heteroaryl, heteroaryl-$C_{1-3}$-alkyl-, HC(O)—, $C_{1-6}$-alkyl-C(O)—, $C_{3-6}$-cycloalkyl-C(O)—, aryl-C(O)—, $C_{1-4}$-alkyl-O—C(O)—, $(C_{1-4}$-alkyl)$_2$N—C(O)—, HO—, oxo, $C_{1-6}$-alkyl-O— which is optionally fluorinated with 1 to 13 fluorine atoms, $C_{3-6}$-cycloalkyl-O—, heterocyclyl-O—, aryl-O—, heteroaryl-O—, $H_2N$—, $(C_{1-4}$-alkyl)$_2$N—, azetidinyl, pyrrolidinyl and $(C_{1-4}$-alkyl)($C_{1-3}$-alkyl-C(O))N—, and wherein above mentioned aryl-C(O)—, aryl-O—, aryl, aryl-$C_{1-3}$-alkyl-, heteroaryl, heteroaryl-$C_{1-3}$-alkyl- and heteroaryl-O— groups may optionally be substituted with 1 to 3 substituents independently selected from the group consisting of HO—, $C_{1-4}$-alkyl-O—, $F_3CO$—, $F_3C$—, $F_2HCO$—, $FH_2CO$—, heterocyclyl-O—, cyano, halogen, $F_5S$—, $(C_{1-4}$-alkyl)$_3$Si—, nitro, $H_2N$—, $(C_{1-4}$-alkyl)$_2$N—, $(H_2N)$—C(O)—, $(C_{1-4}$-alkyl)-HN—C(O)—, $(C_{1-4}$-alkyl)$_2$N—C(O)—, $C_{1-4}$-alkyl-O—$C_{1-4}$-alkyl- and $C_{1-6}$-alkyl- which is optionally fluorinated with 1 to 13 fluorine atoms.

6. A compound according to claim 1, wherein D is selected from the group $D^e$ consisting of

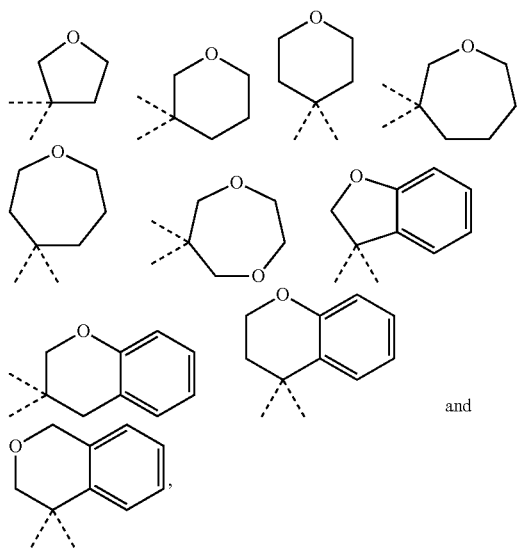

and wherein above mentioned rings $D^e$ may optionally be substituted with 1 to 4 substituents independently selected from the group consisting of halogen, cyano, $C_{1-6}$-alkyl- which is optionally fluorinated with 1 to 13 fluorine atoms, $C_{3-6}$-cycloalkyl-, phenyl- wherein above mentioned phenyl may optionally be substituted with 1 to 3 substituents independently selected from the group consisting of $C_{1-4}$-alkyl-O—, $F_3CO$—, $F_2HCO$—, $FH_2CO$—, cyano, halogen, $F_5S$— and $C_{1-6}$-alkyl- which is optionally fluorinated with 1 to 13 fluorine atoms.

7. A compound according to claim 1, wherein W is selected from the group $W^b$ consisting of —$(R^7)N$—.

8. A compound according to claim 1, wherein $R^1$ is selected from the group $R^{1b}$ consisting of
H, $C_{1-8}$-alkyl-, carbocyclyl, carbocyclyl-$C_{1-3}$-alkyl-, C-linked heterocyclyl, heterocyclyl-$C_{1-3}$-alkyl-, heteroaryl, heteroaryl-$C_{1-3}$-alkyl-, $R^4R^5N$—$C_{1-3}$-alkyl-, $R^4O$—, and $R^4S(O)_m$— with m=0, 1, 2
  wherein above mentioned $C_{1-8}$-alkyl-, carbocyclyl, carbocyclyl-$C_{1-3}$-alkyl-, C-linked heterocyclyl, heterocyclyl-$C_{1-3}$-alkyl-, heteroaryl, heteroaryl-$C_{1-3}$-alkyl- and $R^4R^5N$—$C_{1-3}$-alkyl- groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $H_2N$—, $(C_{1-4}$-alkyl$)_2N$—, $(C_{1-4}$-alkyl$)$-C(O)—, $(C_{1-4}$-alkyl$)$-O—C(O)—, $(C_{1-4}$-alkyl$)$-HN—C(O)—, $(C_{1-4}$-alkyl$)_2N$—C(O)—, $C_{1-4}$-alkyl-O—$C_{1-4}$-alkyl- and $C_{1-6}$-alkyl-, and
  wherein above mentioned $C_{1-4}$-alkyl-O—, $C_{3-6}$-cycloalkyl-O—, heterocyclyl-O—, $(C_{1-4}$-alkyl$)_2$ N—, $(C_{1-4}$-alkyl$)$-C(O)—, $(C_{1-4}$-alkyl$)$-O—C(O)—, $(C_{1-4}$-alkyl$)$-HN—C(O)—, $(C_{1-4}$-alkyl$)_2$ N—C(O)—, $C_{1-4}$-alkyl-O—$C_{1-4}$-alkyl- and $C_{1-6}$-alkyl- may optionally be substituted with 1 to 13 fluorine atoms.

9. A compound according to claim 1, wherein $R^2$ is selected from the group $R^{2b}$ consisting of
H, $C_{1-8}$-alkyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl- and $R^4R^5N$—$C_{2-3}$-alkyl-,
  wherein above mentioned $C_{1-8}$-alkyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl and heteroaryl-$C_{1-3}$-alkyl- groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $H_2N$—, $(C_{1-4}$-alkyl$)_2N$—, $(H_2N)$—C(O)—, $(C_{1-4}$-alkyl$)$-C(O)—, $(C_{1-4}$-alkyl$)$-O—C(O)—, $(C_{1-4}$-alkyl$)$-HN—C(O)—, $(C_{1-4}$-alkyl$)_2N$—C(O)—, $C_{1-4}$-alkyl-O—$C_{1-4}$-alkyl-, $C_{3-5}$-cycloalkyl- and $C_{1-6}$-alkyl-, and
  wherein above mentioned $C_{1-4}$-alkyl-O—, $C_{3-6}$-cycloalkyl-O—, heterocyclyl-O—, $(C_{1-4}$-alkyl$)_2$ N—, $(C_{1-4}$-alkyl$)$-C(O)—, $(C_{1-4}$-alkyl$)$-O—C(O)—, $(C_{1-4}$-alkyl$)$-HN—C(O)—, $(C_{1-4}$-alkyl$)_2$ N—C(O)—, $C_{1-4}$-alkyl-O—$C_{1-4}$-alkyl-, $C_{3-6}$-cycloalkyl- and $C_{1-6}$-alkyl- groups may optionally be substituted with 1 to 13 fluorine atoms.

10. A compound according to claim 1, wherein $R^3$ is selected from the group $R^{3b}$ consisting of
H, $C_{1-8}$-alkyl-, carbocyclyl, carbocyclyl-$C_{1-3}$-alkyl-, C-linked heterocyclyl, heterocyclyl-$C_{1-3}$-alkyl-, aryl-$C_{1-3}$-alkyl-, heteroaryl-$C_{1-3}$-alkyl- and $R^4R^5N$—$C_{2-3}$-alkyl-,
  wherein above mentioned $C_{1-8}$-alkyl-, carbocyclyl, carbocyclyl-$C_{1-3}$-alkyl-, C-linked heterocyclyl, heterocyclyl-$C_{1-3}$-alkyl-, aryl-$C_{1-3}$-alkyl-, and heteroaryl-$C_{1-3}$-alkyl- groups may optionally be substituted with 1 to 3 substituents independently selected from the group consisting of HO—, oxo, $C_{1-4}$-alkyl-O—, $C_{3-6}$-cycloalkyl-O—, heterocyclyl-O—, cyano, halogen, $H_2N$—, $(C_{1-4}$-alkyl$)_2$ N—, $(H_2N)$—C(O)—, $(C_{1-4}$-alkyl$)$-C(O)—, $(C_{1-4}$-alkyl$)$-O—C(O)—, $(C_{1-4}$-alkyl$)$-HN—C(O)—, $(C_{1-4}$-alkyl$)_2N$—C(O)—, $C_{1-4}$-alkyl-O—$C_{1-4}$-alkyl- and $C_{1-6}$-alkyl-, and
  wherein above mentioned $C_{1-4}$-alkyl-O—, $C_{3-6}$-cycloalkyl-O—, heterocyclyl-O—, $(C_{1-4}$-alkyl$)_2$ N—, $(C_{1-4}$-alkyl$)$-C(O)—, $(C_{1-4}$-alkyl$)$-O—C(O)—, $(C_{1-4}$-alkyl$)$-HN—C(O)—, $(C_{1-4}$-alkyl$)_2$ N—C(O)—, $C_{1-4}$-alkyl-O—$C_{1-4}$-alkyl- and $C_{1-6}$-alkyl- groups may optionally be substituted with 1 to 13 fluorine atoms.

11. A compound according to claim 1, wherein $R^4$, $R^5$ are selected independently of each other from the group $R^{4b}/R^{5b}$ consisting of
H, $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, heterocyclyl, heterocyclyl-$C_{1-6}$-alkyl-, aryl, aryl-$C_{1-3}$-alkyl-, aryl-O—$C_{2-3}$-alkyl-, heteroaryl and heteroaryl-$C_{1-3}$-alkyl-,
  wherein above mentioned $C_{1-6}$-alkyl-, $C_{3-7}$-cycloalkyl-, $C_{3-7}$-cycloalkyl-$C_{1-3}$-alkyl-, $C_{3-7}$-cycloalkyl-O—$C_{2-4}$-alkyl-, heterocyclyl or heterocyclyl-$C_{1-6}$-alkyl- groups may optionally be substituted with 1 to 3 substituents independently selected from the group consisting of fluoro, HO—, oxo, $C_{1-4}$-alkyl-O— which is optionally fluorinated with 1 to 9 fluorine atoms, HO—$C_{1-4}$-alkyl-, $C_{1-4}$-alkyl-O—$C_{1-4}$-alkyl-, heterocyclyl, $(C_{1-3}$-alkyl$)_2N$—C(O)—, and $C_{1-6}$-alkyl- which is optionally fluorinated with 1 to 13 fluorine atoms,
  wherein above mentioned aryl-, aryl-$C_{1-3}$-alkyl-, aryl-O—$C_{2-3}$-alkyl-, heteroaryl- and heteroaryl-$C_{1-3}$-alkyl- groups may optionally be substituted with 1 to 3 substituents independently selected from the group consisting of $C_{1-4}$-alkyl-O—, $F_3CO$—, $F_2HCO$—, $FH_2CO$—, cyano, halogen, $(C_{1-4}$-alkyl$)_2N$—C(O)—, and $C_{1-6}$-alkyl- which is optionally fluorinated with 1 to 13 fluorine atoms, or
$R^{4b}$ and $R^{5b}$ form together with the nitrogen atom to which they are attached a 4-12-membered mono-, bicyclic or bridged ring system optionally containing one double bond and/or one aromatic ring and optionally containing one additional heteroatom selected from the group consisting of —O—, —N($R^6$)—,
  wherein 2 geminal hydrogen atoms of the 4-12-membered mono- or bicyclic ring may be replaced by a —$(CH_2)_{1-5}$— group and
  wherein one —$(CH_2)$— group of the —$(CH_2)_{1-5}$— group may be replaced by —O— or —N($R^6$)— and
  wherein above mentioned 4-12-membered mono-, bicyclic or bridged ring system may optionally be substituted with 1 or 2 substituents independently selected from the group consisting of fluoro, aryl, heteroaryl, $C_{1-6}$-alkyl- which is optionally fluorinated with 1 to 13 fluorine atoms, heterocyclyl, HO—, oxo, $C_{1-6}$-alkyl-O—, $C_{3-6}$-cycloalkyl-O—, HO—$C_{1-4}$-alkyl-, $C_{1-4}$-alkyl-O—$C_{1-4}$-alkyl-, heterocyclyl-O— and $(R^6)_2N$—, wherein the directly above mentioned aryl and heteroaryl groups may optionally be substituted with 1 to 3 substituents independently selected from the group consisting of $C_{1-4}$-alkyl-O—, $F_3CO$—, $F_2HCO$—, $FH_2CO$—, cyano, halogen, $(C_{1-4}\text{-alkyl})_2N$—C(O)— and $C_{1-6}$-alkyl- which is optionally fluorinated with 1 to 13 fluorine atoms.

12. A compound according to claim 1, wherein
$R^4$, $R^5$ are selected independently of each other from the group $R^{4e}/R^{5e}$ consisting of
H, $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl-, tetrahydropyranyl-$C_{1-3}$-alkyl-,
wherein above mentioned $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl-, tetrahydropyranyl-$C_{1-3}$-alkyl-groups may optionally be substituted with 1 to 3 substituents independently selected from the group consisting of fluoro, HO—, oxo, $C_{1-4}$-alkyl-O—, HO—$C_{1-4}$-alkyl-, $C_{1-4}$-alkyl-O—$C_{1-4}$-alkyl- and $C_{1-3}$-alkyl- which is optionally fluorinated with 1 to 7 fluorine atoms,
or
$R^{4e}$ and $R^{5e}$ form together with the nitrogen atom to which they are attached a ring system selected from the group consisting of

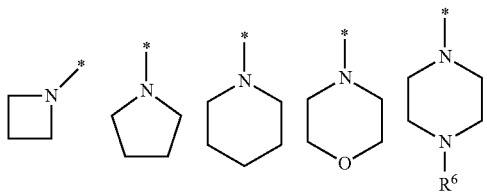

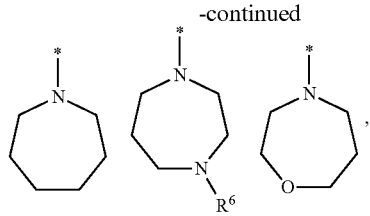

wherein above mentioned monocyclic rings may optionally be substituted with 1 or 2 substituents independently selected from the group consisting of fluoro, $C_{1-3}$-alkyl- which is optionally fluorinated with 1 to 7 fluorine atoms, HO—, oxo, $C_{1-6}$-alkyl-O—, $C_{3-6}$-cycloalkyl-O—, HO—$C_{1-4}$-alkyl- and $C_{1-4}$-alkyl-O—$C_{1-4}$-alkyl-.

13. A compound according to claim 1, wherein
$R^6$ is selected independently of each other from the group $R^{6b}$ consisting of
H, $C_{1-6}$-alkyl-, $C_{3-6}$-cycloalkyl, oxetanyl, tetrahydrofuryl, tetrahydropyranyl, pyridinyl, pyrimidinyl, pyridazinyl, pyrazinyl, triazinyl, thiazolyl, oxadiazolyl, oxazolyl, HC(O)—, $C_{1-6}$-alkyl-C(O)—, $C_{3-6}$-cycloalkyl-C(O)—, phenyl-C(O)—, $C_{1-4}$-alkyl-O—C(O)— and $(C_{1-4}\text{-alkyl})_2N$—C(O)—,
wherein above mentioned $C_{1-6}$-alkyl-, $C_{3-6}$-cycloalkyl-, $C_{1-6}$-alkyl-C(O)— and $C_{3-6}$-cycloalkyl-C(O)— groups may optionally be substituted with 1-13 fluorine atoms,
wherein the aforementioned phenyl-C(O)—, pyridinyl, pyrimidinyl, pyridazinyl, pyrazinyl, triazinyl, thiazolyl oxadiazolyl and oxazolyl groups may optionally be substituted with 1 to 3 substituents independently selected from the group consisting of $C_{1-4}$-alkyl-O—, $F_3C$—, $F_3CO$—, $F_2HCO$—, $FH_2CO$—, cyano, halogen, and $C_{1-3}$-alkyl-.

14. A compound according to claim 1, wherein
$R^7$ is selected from the group $R^{7b}$ consisting of
H.

15. A pharmaceutically acceptable salt of a compound according to any one of claims 1-14.

16. A pharmaceutical composition comprising a compound according to claim 1 and a pharmaceutically acceptable carrier.

* * * * *